_US007615555B2_

United States Patent
Faull et al.

(10) Patent No.: US 7,615,555 B2
(45) Date of Patent: Nov. 10, 2009

(54) PIPERIDINE DERIVATIVES AS MODULATORS OF CHEMOKINE RECEPTOR CCR5

(75) Inventors: Alan Faull, Macclesfield (GB); Howard Tucker, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 248 days.

(21) Appl. No.: 11/587,330

(22) PCT Filed: Apr. 20, 2005

(86) PCT No.: PCT/SE2005/000574

§ 371 (c)(1), (2), (4) Date: Oct. 20, 2006

(87) PCT Pub. No.: WO2005/101989

PCT Pub. Date: Nov. 3, 2005

(65) Prior Publication Data

US 2007/0167442 A1  Jul. 19, 2007

(30) Foreign Application Priority Data

Apr. 23, 2004  (SE) .................................. 0401057
Jan. 10, 2005  (SE) .................................. 0500057

(51) Int. Cl.
| | |
|---|---|
| A61K 31/4545 | (2006.01) |
| A61K 31/437 | (2006.01) |
| A61K 31/496 | (2006.01) |
| C07D 401/14 | (2006.01) |
| C07D 403/14 | (2006.01) |
| C07D 413/14 | (2006.01) |
| C07D 487/04 | (2006.01) |
| A61K 31/46 | (2006.01) |
| C07D 405/14 | (2006.01) |
| C07D 451/04 | (2006.01) |

(52) U.S. Cl. .............................. 514/253.04; 514/253.09; 514/303; 514/316; 514/383; 514/394; 544/360; 544/364; 546/113; 546/187; 548/262.2; 548/305.1

(58) Field of Classification Search ........................ None
See application file for complete search history.

(56) References Cited

U.S. PATENT DOCUMENTS

| | | | |
|---|---|---|---|
| 6,288,084 B1 | 9/2001 | Luly et al. ................... 514/318 |
| 7,192,973 B2 | 3/2007 | Tucker | |
| 2007/0161646 A1 | 7/2007 | Tucker | |
| 2007/0259914 A1 | 11/2007 | Tucker | |
| 2008/0021038 A1 | 1/2008 | Tucker et al. | |
| 2008/0139612 A1 | 6/2008 | Faull et al. | |
| 2008/0139613 A1 | 6/2008 | Brown et al. | |

FOREIGN PATENT DOCUMENTS

| | | |
|---|---|---|
| EP | 0 903 349 | 3/1999 |
| EP | 1 013 276 | 6/2000 |
| WO | WO 92/02502 | 2/1992 |
| WO | WO 99/04794 | 2/1999 |
| WO | WO 99/25686 | 5/1999 |
| WO | WO 99/38514 | 8/1999 |
| WO | WO 01/14333 | 3/2001 |
| WO | WO 01/87839 | 11/2001 |
| WO | WO 01/90106 | 11/2001 |
| WO | WO 03/042205 | 5/2003 |
| WO | WO 2004/054974 | 7/2004 |
| WO | WO 2004/056773 | 7/2004 |
| WO | WO 2004/056808 | 7/2004 |
| WO | WO 2004/056809 | 7/2004 |
| WO | WO 2006/001751 | 1/2006 |
| WO | WO 2006/001752 | 1/2006 |

OTHER PUBLICATIONS

Wang et al. Rheumatology,vol. 43, p. 569-573 (2004).*
Cook, Reviews in Neurological Diseases, vol. 1, p. 37-40 (2004).*
Owen, Pulmonary Pharmacology & Therapeutics vol. 14, p. 193-202 (2001).*
Fischereder et al. The Lancet vol. 357, p. 1758-1761 (2001).*
Vincenti, American Journal of Transplantation vol. 2, p. 898-903 (2002) (Abstract).*

* cited by examiner

*Primary Examiner*—Emily Bernhardt
(74) *Attorney, Agent, or Firm*—Morgan Lewis & Bockius LLP

(57) ABSTRACT

Compounds of formula (I): compositions comprising them, processes for preparing them and their use in medical therapy (for example modulating CCR5 receptor activity in a warm blooded animal).

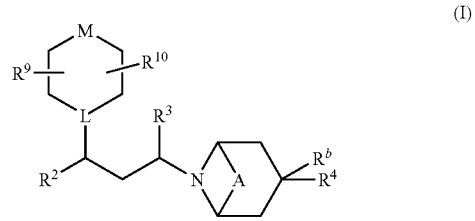

(I)

10 Claims, No Drawings

PIPERIDINE DERIVATIVES AS MODULATORS OF CHEMOKINE RECEPTOR CCR5

The present invention relates to heterocyclic derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in WO01/87839, WO01/66525, WO00/08013, WO99/38514 and WO99/04794.

Chemokines are chemotactic cytokines that are released by a wide variety of cells to attract macrophages, T cells, eosinophils, basophils and neutrophils to sites of inflammation and also play a rôle in the maturation of cells of the immune system. Chemokines play an important rôole in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. The chemokine superfamily can be divided into two main groups exhibiting characteristic structural motifs, the Cys-X-Cys (C-X-C, or α) and Cys-Cys (C-C, or β) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C-C chemokines include potent chemoattractants of monocytes and lymphocytes but not neutrophils such as human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

The CCR5 receptor is expressed on T-lymphocytes, monocytes, macrophages, dendritic cells, microglia and other cell types. These detect and respond to several chemokines, principally "regulated on activation normal T-cell expressed and secreted" (RANTES), macrophage inflammatory proteins (MIP) MIP-1α and MIP-1β and monocyte chemoattractant protein-2 (MCP-2).

This results in the recruitment of cells of the immune system to sites of disease. In many diseases it is the cells expressing CCR5 which contribute, directly or indirectly, to tissue damage. Consequently, inhibiting the recruitment of these cells is beneficial in a wide range of diseases.

CCR5 is also a co-receptor for HIV-1 and other viruses, allowing these viruses to enter cells. Blocking the receptor with a CCR5 antagonist or inducing receptor internalisation with a CCR5 agonist protects cells from viral infection.

The present invention provides a piperidine or tropane compound of formula (I):

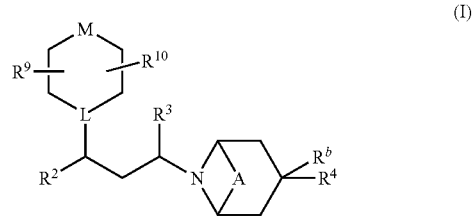

wherein:
A is absent or is $(CH_2)_2$;
L is CH or N;
M is $NR^1$, O, S, S(O) or $S(O)_2$;
$R^1$ is hydrogen, $C_{1-6}$ alkyl [optionally substituted by phenyl {which itself optionally substituted by halo, $C_{1-4}$ alkyl, $C_{1-4}$ alkoxy, cyano, nitro, $CF_3$, $OCF_3$, $(C_{1-4}$ alkyl)$C(O)NH$, $S(O)_2NH_2$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, $(C_{1-4}$ alkyl)$C(O)NH$, $S(O)_2NH_2$, $C_{1-4}$ alkylthio, $S(O)(C_{1-4}$ alkyl) or $S(O)_2(C_{1-4}$ alkyl)}], phenyl {optionally substituted by halo, $C_{1-4}$ alkyl, $C_{1-4}$ alkoxy, cyano, nitro, $CF_3$, $OCF_3$, $(C_{1-4}$ alkyl)$C(O)NH$, $S(O)_2NH_2$, $C_{1-4}$ alkylthio, $S(O)(C_{1-4}$ alkyl) or $S(O)_2(C_{1-4}$ alkyl)}, heteroaryl {optionally substituted by halo, $C_{1-4}$ alkyl, $C_{1-4}$ alkoxy, cyano, nitro, $CF_3$, $(C_{1-4}$ alkyl)$C(O)NH$, $S(O)_2NH_2$, $C_{1-4}$ alkylthio, $S(O)(C_{1-4}$ alkyl) or $S(O)_2(C_{1-4}$ alkyl)}, $S(O)_2R^5$, $S(O)_2NR^6R^7$, $C(O)R^8$, $C(O)_2(C_{1-6}$ alkyl) (such as tert-butoxycarbonyl), $C(O)_2(phenyl(C_{1-2}$ alkyl)) (such as benzyloxycarbonyl) or $C(O)NHR^{11}$;
$R^2$ is phenyl (optionally substituted by halo, CN or $C_{1-4}$ haloalkyl), thienyl or halothienyl;
$R^3$ is hydrogen or methyl;
$R^b$ is hydrogen or $C_{1-3}$ alkyl;
$R^4$ is a five or six membered heterocycle containing at least one carbon atom, one to four nitrogen atoms and, optionally, one oxygen or sulphur atom,
a ring carbon of said heterocycle $R^4$ being optionally substituted by oxo, $C_{1-6}$ alkyl [which is optionally substituted by halogen, CN, OH, $C_{1-4}$ alkoxy, $S(C_{1-4}$ alkyl), $S(O)(C_{1-4}$ alkyl), $S(O)_2(C_{1-4}$ alkyl) or heterocyclyl {itself optionally substituted by $C_{1-6}$ alkyl [which is optionally substituted by oxo, halogen, OH, $C_{1-4}$ alkoxy, $OCF_3$, $C(O)(C_{1-4}$ alkoxy), CN, $C(O)NH_2$, $C(O)NH(C_{1-4}$ alkyl), $C(O)N(C_{1-4}$ alkyl)$_2$, $NH_2$, $NH(C_{1-4}$ alkyl) or $N(C_{1-4}$ alkyl)$_2$], $C(O)(C_{1-4}$ alkyl) [wherein the alkyl is optionally substituted by $C_{1-4}$ alkoxy or fluoro], benzyl [which is optionally substituted by halogen, $C_{1-4}$ alkyl, $C_{1-4}$ alkoxy, $CF_3$, $OCF_3$, cyano, nitro, $S(C_{1-4}$ alkyl), $S(O)(C_{1-4}$ alkyl) or $S(O)_2(C_{1-4}$ alkyl)], $C(O)(C_{1-4}$ alkoxy), $C(O)NH_2$, $C(O)NH(C_{1-4}$ alkyl), $C(O)N(C_{1-4}$ alkyl)$_2$ or $S(O)_2(C_{1-4}$ alkyl) [wherein the alkyl is optionally substituted by fluoro]}], $C_{2-6}$ alkenyl, $C_{3-6}$ cycloalkyl, CN, $C(O)NH_2$, $C(O)NH(phenylC_{1-2}$ alkyl), phenyl [which is optionally substituted by halogen, $C_{1-4}$ alkyl, $C_{1-4}$ alkoxy, $CF_3$, $OCF_3$, cyano, nitro, $S(C_{1-4}$ alkyl), $S(O)(C_{1-4}$ alkyl) or $S(O)_2(C_{1-4}$ alkyl)] or benzyl [which is optionally substituted by halogen, $C_{1-4}$ alkyl, $C_{1-4}$ alkoxy, $CF_3$, $OCF_3$, cyano, nitro, $S(C_{1-4}$ alkyl), $S(O)(C_{1-4}$ alkyl) or $S(O)_2(C_{1-4}$ alkyl)];
where possible, a ring nitrogen of said heterocycle $R^4$ being optionally substituted by $C_{1-6}$ alkyl [optionally substituted by oxo, halogen, OH, $C_{1-4}$ alkoxy, $OCF_3$, $NH_2$, NH($C_{1-4}$ alkyl), N($C_{1-4}$ alkyl)$_2$, S($C_{1-4}$ alkyl), S(O)($C_{1-4}$ alkyl), S(O)$_2$($C_{1-4}$ alkyl), C(O)($C_{1-4}$ alkoxy), CONH$_2$, CONH($C_{1-4}$ alkyl), CON($C_{1-4}$ alkyl)$_2$, cyano, aryl {optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)}, heteroaryl {optionally substituted by oxo, halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)}, heterocyclyl {optionally substituted by $C_{1-4}$ alkyl, aryl [optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)], SO$_2$NH($C_{1-4}$ alkyl), SO$_2$N($C_{1-4}$ alkyl)$_2$, CONH($C_{1-4}$ alkyl), CON($C_{1-4}$ alkyl)$_2$, CO($C_{1-4}$ alkyl), CO(aryl) [optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)], SO$_2$(aryl) [optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)]}], $C_{3-6}$ cycloalkyl, CO($C_{1-4}$ alkyl) [optionally substituted by halogen], CO(aryl) [optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)], SO$_2$(aryl) [optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)], SO$_2$($C_{1-4}$ alkyl) [optionally substituted by fluorine], COO($C_{1-6}$ alkyl), aryl [optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)?($C_{1-4}$ alkyl)], heteroaryl [optionally substituted by oxo, halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)], CONH($C_{1-4}$ alkyl), CONH(aryl) [optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)], SO$_2$NH($C_{1-4}$ alkyl) or SO$_2$N($C_{1-4}$ alkyl)$_2$;

provided that when a ring nitrogen of said heterocycle R$^4$ is substituted by an alkyl group, said alkyl does not carry an oxo, halogen, OH, $C_{1-4}$ alkoxy, OCF$_3$, NH$_2$, NH($C_{1-4}$ alkyl), N($C_{1-4}$ alkyl)$_2$, S($C_{1-4}$ alkyl), S(O)($C_{1-4}$ alkyl) or S(O)$_2$($C_{1-4}$ alkyl) substituent on the carbon attached to the ring nitrogen of said heterocycle R$^4$;

the five or six membered heterocycle R$^4$ being optionally fused to a cyclohexane, piperidine, benzene, pyridine, pyridazine, pyrimidine or pyrazine ring; the ring carbon atoms of said fused cyclohexane, piperidine, benzene, pyridine, pyridazine, pyrimidine or pyrazine ring being optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl); and the nitrogen of said fused piperidine ring being optionally substituted by $C_{1-4}$ alkyl [which is optionally substituted by oxo, halogen, OH, $C_{1-4}$ alkoxy, OCF$_3$, C(O)($C_{1-4}$ alkoxy), CN, C(O)NH$_2$, C(O)NH($C_{1-4}$ alkyl), C(O)N($C_{1-4}$ alkyl)$_2$, NH$_2$, NH($C_{1-4}$ alkyl) or N($C_{1-4}$ alkyl)$_2$], C(O)($C_{1-4}$ alkyl) [wherein the alkyl is optionally substituted by $C_{1-4}$ alkoxy or halogen], benzyl [which is optionally substituted by halogen, $C_{1-4}$ alkyl, $C_{1-4}$ alkoxy, CF$_3$, OCF$_3$, cyano, nitro, S($C_{1-4}$ alkyl), S(O)($C_{1-4}$ alkyl) or S(O)$_2$($C_{1-4}$ alkyl)], C(O)($C_{1-4}$ alkoxy), C(O)NH$_2$, C(O)NH($C_{1-4}$ alkyl), C(O)N($C_{1-4}$ alkyl)$_2$ or S(O)$_2$($C_{1-4}$ alkyl) [wherein the alkyl is optionally substituted by fluoro];

R$^5$ is $C_{1-6}$ alkyl [optionally substituted by halo (such as fluoro), $C_{1-4}$ alkoxy, phenyl {which itself optionally substituted by halo, $C_{1-4}$ alkyl, $C_{1-4}$ alkoxy, cyano, nitro, CF$_3$, OCF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)} or heteroaryl {which itself optionally substituted by halo, $C_{1-4}$ alkyl, $C_{1-4}$ alkoxy, cyano, nitro, CF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)}], $C_{3-7}$ cycloalkyl (optionally substituted by halo or $C_{1-6}$ alkyl), pyranyl, phenyl {optionally substituted by halo, $C_{1-4}$ alkyl, $C_{1-4}$ alkoxy, cyano, nitro, CF$_3$, OCF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)}, heteroaryl {optionally substituted by halo, $C_{1-4}$ alkyl, $C_{1-4}$ alkoxy, cyano, nitro, CF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)} or a 5- or 6-membered nitrogen containing heterocyclic ring {optionally substituted by S(O)$_2$($C_{1-4}$ alkyl) or C(O)($C_{1-4}$ alkyl)};

R$^8$ and R$^{11}$ are, independently, hydrogen, $C_{1-6}$ alkyl [optionally substituted by halo (such as fluoro), $C_{1-4}$ alkoxy, phenyl {which itself optionally substituted by halo, $C_{1-4}$ alkyl, $C_{1-4}$ alkoxy, cyano, nitro, CF$_3$, OCF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)} or heteroaryl {which itself optionally substituted by halo, $C_{1-4}$ alkyl, $C_{1-4}$ alkoxy, cyano, nitro, CF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)}], $C_{3-7}$ cycloalkyl (optionally substituted by halo or $C_{1-6}$ alkyl), pyranyl, phenyl {optionally substituted by halo, $C_{1-4}$ alkyl, $C_{1-4}$ alkoxy, cyano, nitro, CF$_3$, OCF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)}, heteroaryl {optionally substituted by halo, $C_{1-4}$ alkyl, $C_{1-4}$ alkoxy, cyano, nitro, CF$_3$, ($C_{1-4}$ alkyl)C(O)NH, S(O)$_2$NH$_2$, $C_{1-4}$ alkylthio, S(O)($C_{1-4}$ alkyl) or S(O)$_2$($C_{1-4}$ alkyl)} or a 5- or 6-membered nitrogen containing heterocyclic ring {optionally substituted by S(O)$_2$($C_{1-4}$ alkyl) or C(O)($C_{1-4}$ alkyl)};

R$^6$ and R$^7$ are, independently, hydrogen or $C_{1-4}$ alkyl; or together R$^6$ and R$^7$ join to form a 5- or 6-membered ring which is optionally substituted with $C_{1-4}$ alkyl or phenyl (wherein the phenyl ring is optionally substituted by halo, cyano, nitro, hydroxy, $C_{1-4}$ alkyl, $C_{1-4}$ alkoxy, S(O)$_m$$C_{1-4}$ alkyl, S(O)$_2$NH$_2$, S(O)$_2$NH($C_{1-4}$ alkyl), S(O)$_2$N($C_{1-4}$ alkyl)$_2$, NHS(O)$_2$($C_{1-4}$ alkyl), NH$_2$, NH($C_{1-4}$ alkyl), N($C_{1-4}$ alkyl)$_2$, NHC(O)NH$_2$, C(O)NH$_2$, C(O)NH($C_{1-4}$ alkyl), NHC(O)($C_{1-4}$ alkyl), CO$_2$H, CO$_2$($C_{1-4}$ alkyl), C(O)($C_{1-4}$ alkyl), CF$_3$, CHF$_2$, CH$_2$F, CH$_2$CF$_3$ or OCF$_3$);

R$^9$ and R$^{10}$ are, independently, hydrogen or $C_{1-6}$ alkyl;

or a pharmaceutically acceptable salt thereof.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts (adducts) such as a hydrochloride, hydrobromide, phosphate, acetate, fumarate, maleate, tartrate, citrate, oxalate, methanesulphonate, p-toluenesulphonate or formate. Acid addition salt is, for example hydrochloride or formate.

The compounds of the invention may exist as a solvate (such as a hydrate) and the present invention covers all such solvates.

Halogen is, for example, chloro, fluoro or bromo; such as chloro or fluoro.

Alkyl groups and moieties are straight or branched chain and are, for example, methyl (sometimes abbreviated to Me), ethyl, n-propyl, iso-propyl, n-butyl, sec-butyl or tert-butyl.

Alkyl substituted by halogen is, for example, CF$_3$, CHF$_2$, CH$_2$F, CH$_2$CF$_3$ or C$_2$F$_5$.

Cycloalkyl is for example, cyclopropyl, cyclopentyl or cyclohexyl.

N-Linked heterocyclyl is a nitrogen-linked, non-aromatic 3, 4, 5 or 6 membered ring optionally comprising one further heteroatom (selected from the group comprising nitrogen, oxygen and sulphur). It is, for example, aziridinyl, azetidinyl, pyrrolidinyl, piperidinyl, piperazinyl, morpholinyl or thiomorpholinyl.

A 5- or 6-membered nitrogen containing heterocyclic ring contains, for example, only one nitrogen atom, all other ring atoms being carbon. It is, for example, pyrrolidinyl or piperidinyl.

Heteroaryl is an aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Heteroaryl is, for example, furyl, thienyl (also known as thiophenyl), pyrrolyl, thiazolyl, isothiazolyl, pyrazolyl, oxazolyl, isoxazolyl, imidazolyl, [1,2,4]-triazolyl, pyridinyl, pyrimidinyl, indolyl, benzo[b]furyl (also known as benzfuryl), benz[b]thienyl (also known as benzthienyl or benzthiophenyl), indazolyl, benzimidazolyl, benztriazolyl, benzoxazolyl, benzthiazolyl, 1,2,3-benzothiadiazolyl, an imidazopyridinyl (such as imidazo[1,2a]pyridinyl), thieno[3,2-b]pyridin-6-yl, 1,2,3-benzoxadiazolyl (also known as benzo[1,2,3]thiadiazolyl), 2,1,3-benzothiadiazolyl, benzofurazan (also known as 2,1,3-benzoxadiazolyl), quinoxalinyl, a pyrazolopyridine (for example 1H-pyrazolo[3,4-b]pyridinyl), quinolinyl, isoquinolinyl, a naphthyridinyl (for example [1,6]naphthyridinyl or [1,8]naphthyridinyl), a benzothiazinyl or dibenzothiophenyl (also known as dibenzothienyl); or an N-oxide thereof, or an S-oxide or S-dioxide thereof. Heteroaryl is, for example, pyridyl, pyrimidinyl, indolyl or benzimidazolyl.

The five membered heterocycle of $R^4$ is, for example, pyrazolyl, imidazolyl, 1,3-dihydro-2H-imidazol-2-one, imidazolidin-2-one, 1,2,4-triazolyl, 1,2,3-triazolyl, tetrazolyl, oxazolyl, isoxazolyl, 1,2,4-oxadiazolyl, 1,3,4-oxadiazolyl or thiazolyl (such as pyrazolyl, imidazolyl, 1,2,4-triazolyl, 1,2,3-triazolyl, tetrazolyl, oxazolyl, isoxazolyl, 1,2,4-oxadiazolyl, 1,3,4-oxadiazolyl or thiazolyl). The six membered heterocycle of $R^4$ is, for example, piperidinyl or piperazinyl. When the five or six membered heterocycle of $R^4$ is fused to a benzene or pyridine ring the resulting bicyclic is, for example, benzimidazolyl, 1,3-dihydro-2H-benzimidazolyl, benztriazolyl, an imidazopyridinyl (such as imidazo[4,5c]pyridinyl), [such as benzimidazolyl, benztriazolyl or an imidazopyridinyl (such as imidazo[4,5c]pyridinyl)]. When the five or six membered ring heterocycle of $R^4$ (for example the five membered ring heterocycle of $R^4$) is fused to a saturated cycloalkyl or piperidine the resulting bicyclic is, for example, 4,5,6,7-tetrahydro-1H-benzimidazole, 4,5,6,7-tetrahydro-3H-imidazo[4,5-c]pyridine or 4,5,6,7-tetrahydro-1H-imidazo[4,5-c]pyridine. Additionally, when the five or six membered ring heterocycle of $R^4$ (for example the five membered ring heterocycle of $R^4$) is fused to a saturated cycloalkyl or piperidine the resulting bicyclic is, for example, 1,4,6,7-tetrahydro-5H-imidazo[4,5c]pyridinyl ($C_{1-4}$ Alkyl)phenyl is, for example, benzyl, 2-phenylethyl or 1-phenyleth-1-yl. ($C_{1-4}$ Alkyl)heteroaryl is, for example, pyridylmethyl or pyrimidinylmethyl. NHC(O)Heteroaryl is, for example, NHC(O)pyridyl. NHC(O)($C_{1-4}$Alkyl)phenyl is, for example, NHC(O)benzyl. NHC(O)($C_{1-4}$Alkyl)heteroaryl is, for example, NHC(O)CH$_2$pyridyl. NHS(O)$_2$Heteroaryl is, for example, NHS(O)$_2$pyridyl. NHS(O)$_2$($C_{1-4}$ Alkyl)phenyl is, for example, NHS(O)$_2$benzyl. NHS(O)$_2$($C_{1-4}$ Alkyl)heteroaryl is, for example, NHS(O)$_2$CH$_2$pyridyl. NHC(O)NH-heteroaryl is, for example, NHC(O)NHpyridyl. NHC(O)NH($C_{1-4}$Alkyl)phenyl is, for example, NHC(O)NHbenzyl. NHC(O)NH($C_{1-4}$ Alkyl)heteroaryl is, for example, NHC(O)NHCH$_2$pyridyl.

In one particular aspect the present invention provides a compound wherein $R^b$ is hydrogen; and $R^4$ is a five membered heterocycle containing at least one carbon atom, one to four nitrogen atoms and, optionally, one oxygen or sulphur atom, said heterocycle being optionally substituted by oxo, $C_{1-6}$ alkyl, H$_2$NC(O), (phenylC$_{1-2}$ alkyl)HNC(O) or benzyl [which is optionally substituted by halogen, $C_{1-4}$ alkyl, $C_{1-4}$ alkoxy, CF$_3$, OCF$_3$, S(C$_{1-4}$ alkyl), S(O)(C$_{1-4}$ alkyl) or S(O)$_2$(C$_{1-4}$alkyl)]; the five membered heterocycle being optionally fused to a cyclohexane, piperidine, benzene, pyridine, pyridazine, pyrimidine or pyrazine ring; the ring carbon atoms of said fused cyclohexane, piperidine, benzene, pyridine, pyridazine, pyrimidine or pyrazine ring being optionally substituted by halogen, cyano, $C_{1-4}$ alkyl, $C_{1-4}$ alkoxy, CF$_3$, OCF$_3$, S(C$_{1-4}$ alkyl), S(O)(C$_{1-4}$ alkyl) or S(O)$_2$(C$_{1-4}$ alkyl); and the nitrogen of the fused piperidine ring being optionally substituted by $C_{1-4}$ alkyl {which is optionally substituted by oxo, halogen, OH, $C_{1-4}$ alkoxy, OCF$_3$, C(O)O(C$_{1-4}$ alkyl), CN, C(O)NH$_2$, C(O)NH(C$_{1-4}$ alkyl), C(O)N(C$_{1-4}$ alkyl)$_2$, NH$_2$, NH(C$_{1-4}$ alkyl) or N(C$_{1-4}$ alkyl)$_2$}, C(O)(C$_{1-4}$ alkyl) {wherein the alkyl is optionally substituted by $C_{1-4}$ alkoxy or fluoro}, C(O)O(C$_{1-4}$ alkyl), C(O)NH$_2$, C(O)NH (C$_{1-4}$ alkyl), C(O)N(C$_{1-4}$ alkyl)$_2$ or S(O)$_2$(C$_{1-4}$ alkyl) {wherein the alkyl is optionally substituted by fluoro}; and A, M, L, $R^2$, $R^3$, $R^9$ and $R^{10}$ are as defined above.

In another aspect the invention provides a compound wherein $R^4$ is a five or six membered heterocycle containing at least one carbon atom, one to four nitrogen atoms and, optionally, one oxygen or sulphur atom, a ring carbon of said heterocycle $R^4$ being optionally substituted by oxo, $C_{1-6}$ alkyl [which is optionally substituted by halogen, CN, OH, $C_{1-4}$ alkoxy, S(C$_{1-4}$ alkyl), S(O)(C$_{1-4}$ alkyl), S(O)$_2$(C$_{1-4}$ alkyl) or heterocyclyl {itself optionally substituted by $C_{1-6}$ alkyl [which is optionally substituted by oxo, halogen, OH, $C_{1-4}$ alkoxy, OCF$_3$, C(O)(C$_{1-4}$ alkoxy), CN, C(O)NH$_2$, C(O)NH(C$_{1-4}$ alkyl), C(O)N(C$_{1-4}$ alkyl)$_2$, NH$_2$, NH(C$_{1-4}$ alkyl) or N(C$_{1-4}$ alkyl)$_2$], C(O)(C$_{1-4}$ alkyl) [wherein the alkyl is optionally substituted by $C_{1-4}$ alkoxy or fluoro], benzyl [which is optionally substituted by halogen, $C_{1-4}$ alkyl, $C_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)], C(O)(C$_{1-4}$ alkoxy), C(O)NH$_2$, C(O)NH(C$_{1-4}$ alkyl), C(O)N(C$_{1-4}$ alkyl)$_2$ or S(O)$_2$(C$_{1-4}$ alkyl) [wherein the alkyl is optionally substituted by fluoro]}], $C_{2-6}$ alkenyl, CN, C(O)NH$_2$, C(O)NH(phenylC$_{1-2}$ alkyl), phenyl [which is optionally substituted by halogen, $C_{1-4}$ alkyl, $C_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)] or benzyl [which is optionally substituted by halogen, $C_{1-4}$ alkyl, $C_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)];

where possible, a ring nitrogen of said heterocycle $R^4$ being optionally substituted by $C_{1-6}$ alkyl [optionally substituted by oxo, halogen, OH, $C_{1-4}$ alkoxy, OCF$_3$, NH$_2$, NH(C$_{1-4}$ alkyl), N(C$_{1-4}$ alkyl)$_2$, S(C$_{1-4}$ alkyl), S(O)(C$_{1-4}$ alkyl), S(O)$_2$(C$_{1-4}$ alkyl), C(O)(C$_{1-4}$ alkoxy), CONH$_2$, CONH(C$_{1-4}$ alkyl), CON(C$_{1-4}$ alkyl)$_2$, cyano, aryl {optionally substituted by halogen, $C_{1-4}$ alkyl, $C_{1-4}$ alkoxy, CF$_3$, OCF$_3$, cyano, nitro, S(C$_{1-4}$ alkyl), S(O) (C$_{1-4}$ alkyl) or S(O)$_2$(C$_{1-4}$ alkyl)}, heteroaryl {optionally substituted by oxo, halogen, $C_{1-4}$ alkyl, $C_{1-4}$ alkoxy, CF$_3$, OCF$_3$, cyano, nitro, S(C$_{1-4}$ alkyl), S(O)(C$_{1-4}$ alkyl)

or S(O)$_2$(C$_{1-4}$ alkyl)}, heterocyclyl {optionally substituted by C$_{1-4}$ alkyl, aryl [optionally substituted by halogen, C$_{1-4}$ alkyl, C$_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)], SO$_2$NH(C$_{1-4}$ alkyl), SO$_2$N(C$_{1-4}$ alkyl)$_2$, CONH(C$_{1-4}$ alkyl), CON(C$_{1-4}$ alkyl)$_2$, CO(C$_{1-4}$ alkyl), CO(aryl) [optionally substituted by halogen, C$_{1-4}$ alkyl, C$_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)], SO$_2$(aryl) [optionally substituted by halogen, C$_{1-4}$ alkyl, C$_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)]}], CO(C$_{1-4}$ alkyl) [optionally substituted by halogen], CO(aryl) [optionally substituted by halogen, C$_{1-4}$ alkyl, C$_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)], SO$_2$(aryl) [optionally substituted by halogen, C$_{1-4}$ alkyl, C$_{1-4}$ alkoxy, CF$_3$, OCF$_3$, cyano, nitro, S(C$_{1-4}$ alkyl), S(O) (C$_{1-4}$ alkyl) or S(O)$_2$(C$_{1-4}$ alkyl)], SO$_2$(C$_{1-4}$ alkyl) [optionally substituted by fluorine], COO(C$_{1-6}$ alkyl), aryl [optionally substituted by halogen, C$_{1-4}$ alkyl, C$_{1-4}$ alkoxy, CF$_3$, OCF$_3$, cyano, nitro, S(C$_{1-4}$ alkyl), S(O) (C$_{1-4}$ alkyl) or S(O)$_2$(C$_{1-4}$ alkyl)], heteroaryl [optionally substituted by oxo, halogen, C$_{1-4}$ alkyl, C$_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)], CONH(C$_{1-4}$ alkyl), CONH(aryl) [optionally substituted by halogen, C$_{1-4}$ alkyl, C$_{1-4}$ alkoxy, CF$_3$, OCF$_3$, cyano, nitro, S(C$_{1-4}$ alkyl), S(O) (C$_{1-4}$ alkyl) or S(O)$_2$(C$_{1-4}$ alkyl)], SO$_2$NH(C$_{1-4}$ alkyl) or SO$_2$N(C$_{1-4}$ alkyl)$_2$;

provided that when a ring nitrogen of said heterocycle R$^4$ is substituted by an alkyl group, said alkyl does not carry an oxo, halogen, OH, C$_{1-4}$ alkoxy, OCF$_3$, NH$_2$, NH(C$_{1-4}$ alkyl), N(C$_{1-4}$ alkyl)$_2$, S(C$_{1-4}$ alkyl), S(O)(C$_{1-4}$ alkyl) or S(O)$_2$(C$_{1-4}$ alkyl) substituent on the carbon attached to the ring nitrogen of said heterocycle R$^4$;

the five or six membered heterocycle R$^4$ being optionally fused to a cyclohexane, piperidine, benzene, pyridine, pyridazine, pyrimidine or pyrazine ring; the ring carbon atoms of said fused cyclohexane, piperidine, benzene, pyridine, pyridazine, pyrimidine or pyrazine ring being optionally substituted by halogen, C$_{1-4}$ alkyl, C$_{1-4}$ alkoxy, CF$_3$, OCF$_3$, cyano, nitro, S(C$_{1-4}$ alkyl), S(O)(C$_{1-4}$ alkyl) or S(O)$_2$ (C$_{1-4}$ alkyl); and the nitrogen of said fused piperidine ring being optionally substituted by C$_{1-4}$ alkyl [which is optionally substituted by oxo, halogen, OH, C$_{1-4}$ alkoxy, OCF$_3$, C(O) (C$_{1-4}$ alkoxy), CN, C(O)NH$_2$, C(O)NH(C$_{1-4}$ alkyl), C(O)N (C$_{1-4}$ alkyl)$_2$, NH$_2$, NH(C$_{1-4}$ alkyl) or N(C$_{1-4}$ alkyl)$_2$], C(O) (C$_{1-4}$ alkyl) [wherein the alkyl is optionally substituted by C$_{1-4}$ alkoxy or halogen], benzyl [which is optionally, substituted by halogen, C$_{1-4}$ alkyl, C$_{1-4}$ alkoxy, CF$_3$, OCF$_3$, cyano, nitro, S(C$_{1-4}$ alkyl), S(O)(C$_{1-4}$ alkyl) or S(O)$_2$(C$_{1-4}$ alkyl)], C(O)(C$_{1-4}$ alkoxy), C(O)NH$_2$, C(O)NH(C$_{1-4}$ alkyl), C(O)N (C$_{1-4}$ alkyl)$_2$ or S(O)$_2$(C$_{1-4}$ alkyl) [wherein the alkyl is optionally substituted by fluoro]; and A, M, L, R$^b$, R$^2$, R$^3$, R$^9$ and R$^{10}$ are as defined above.

In yet another aspect the present invention provides a compound wherein L is CH.

In a further aspect the present invention provides a compound wherein M is O.

In a still further aspect the invention provides a compound wherein M is NR$^1$.

In another aspect the present invention provides a compound wherein A is absent.

In yet another aspect the present invention provides a compound wherein A is CH$_2$CH$_2$.

In a further aspect the invention provides a compound wherein R$^1$ is C$_{1-6}$ alkyl, phenyl {optionally substituted by halo, C$_{1-4}$ alkyl, C$_{1-4}$ alkoxy, cyano, nitro, CF$_3$, OCF$_3$, (C$_{1-4}$ alkyl)C(O)NH, S(O)$_2$NH$_2$, C$_{1-4}$ alkylthio, S(O)(C$_{1-4}$ alkyl) or S(O)$_2$(C$_{1-4}$ alkyl)}, S(O)$_2$R$^5$ or C(O)R$^8$; wherein R$^5$ and R$^8$ are C$_{1-6}$ alkyl, CF$_3$, C$_{3-7}$ cycloalkyl (optionally substituted by halo or C$_{1-6}$ alkyl), phenyl {optionally substituted by halo, C$_{1-4}$ alkyl, C$_{1-4}$ alkoxy, cyano, nitro, CF$_3$, OCF$_3$, (C$_{1-4}$ alkyl) C(O)NH, S(O)$_2$NH$_2$, C$_{1-4}$ alkylthio, S(O)(C$_{1-4}$ alkyl) or S(O)$_2$(C$_{1-4}$ alkyl)} or a 5- or 6-membered nitrogen containing heterocyclic ring {optionally substituted by S(O)$_2$(C$_{1-4}$ alkyl) or C(O)(C$_{1-4}$ alkyl)}.

In another aspect the invention provides a compound wherein R$^1$ is S(O)$_2$R$^5$ or C(O)R$^8$; wherein R$^5$ and R$^8$ are C$_{1-6}$ alkyl, CF$_3$, C$_{3-7}$ cycloalkyl (optionally substituted by halo or C$_{1-6}$ alkyl), phenyl {optionally substituted by halo, C$_{1-4}$ alkyl, C$_{1-4}$ alkoxy, cyano, nitro, CF$_3$, OCF$_3$, (C$_{1-4}$ alkyl)C(O)NH, S(O)$_2$NH$_2$, C$_{1-4}$ alkylthio, S(O)(C$_{1-4}$ alkyl) or S(O)$_2$(C$_{1-4}$ alkyl)} or a 5- or 6-membered nitrogen containing heterocyclic ring {optionally substituted by S(O)$_2$(C$_{1-4}$ alkyl) or C(O) (C$_{1-4}$ alkyl)}.

In yet another aspect the invention provides a compound wherein R$^1$ is S(O)$_2$R$^5$; wherein R$^5$ is C$_{1-6}$ alkyl, CF$_3$, C$_{3-7}$ cycloalkyl (optionally substituted by halo or C$_{1-6}$ alkyl), phenyl {optionally substituted by halo, C$_{1-4}$ alkyl, C$_{1-4}$ alkoxy, cyano, nitro, CF$_3$, OCF$_3$, (C$_{1-4}$ alkyl)C(O)NH, S(O)$_2$NH$_2$, C$_{1-4}$ alkylthio, S(O)(C$_{1-4}$ alkyl) or S(O)$_2$(C$_{1-4}$ alkyl)} or a 5- or 6-membered nitrogen containing heterocyclic ring {optionally substituted by S(O)$_2$(C$_{1-4}$ alkyl) or C(O)(C$_{1-4}$ alkyl)}.

In a still further aspect the invention provides a compound wherein R$^2$ is phenyl optionally substituted by chloro, fluoro or CF$_3$ (for example phenyl, mono-chlorophenyl, mono-fluorophenyl or di-fluorophenyl; such as phenyl 3-fluorophenyl or 3,5-difluorophenyl), thienyl or halothienyl (for example mono-chlorothienyl; such as 4-chlorothien-2-yl or 5-chlorothien-2-yl). In another aspect R$^2$ is phenyl, mono-chlorophenyl, mono-fluorophenyl or di-fluorophenyl (such as phenyl, 3-fluorophenyl or 3,5-difluorophenyl) or thienyl. In yet another aspect R$^2$ is 3-fluorophenyl or 3,5-difluorophenyl.

In another aspect R$^3$ is hydrogen.

In yet another aspect of the invention R$^9$ and R$^{10}$ are both hydrogen.

In a further aspect the invention provides a compound wherein R$^b$ is hydrogen.

In yet another aspect R$^4$ is 1,2,4-triazolyl, thiazolyl, 1,2,4-oxadiazolyl, imidazolyl, 1,3-dihydro-2H-imidazolyl, 1,2,3-triazolyl or piperidinyl substituted as described above. In a further aspect R$^4$ is 1,2,4-triazolyl, thiazolyl, 1,2,4-oxadiazolyl, piperidinyl, benzimidazolyl, 1,3-dihydro-2H-benzimidazolyl, benzotriazolyl or an imidazopyridinyl (such as imidazo[4,5c]pyridinyl, 1,4,6,7-tetrahydro-5H-imidazo[4,5-c] pyridinyl or 4,5,6,7-tetrahydro-3H-imidazo[4,5-c]pyridinyl), each of which is unsubstituted or substituted by one or two of the same or different C$_{1-6}$ alkyl (for example C$_{1-4}$ alkyl; such as methyl), CF$_3$, OH (which may tautomerise to the keto form), oxo (which may tautomerise to the hydroxy form), C$_{1-4}$ alkyl substituted by heterocyclyl (which is itself optionally substituted by S(O)$_2$(C$_{1-4}$ alkyl)), S(O)$_2$(C$_{1-4}$ alkyl), (C$_{1-4}$ alkyl)C(O), (C$_{1-4}$ haloalkyl)C(O), (C$_{1-4}$ alkoxy)C(O), C(O)NH$_2$, C(O)NH(phenyl(C$_{1-2}$ alkyl)) or phenyl(C$_{1-2}$ alkyl); wherein the phenyl of the foregoing phenyl(C$_{1-2}$ alkyl) groups is optionally substituted by halo, C$_{1-4}$ alkyl, C$_{1-4}$ alkoxy, cyano or S(O)$_2$(C$_{1-4}$ alkyl).

In a further aspect R$^4$ is 1,2,4-triazolyl, thiazolyl, 1,2,4-oxadiazolyl, imidazolyl or 1,2,3-triazolyl substituted as described above. In a further aspect R$^4$ is 1,2,4-triazolyl, thiazolyl, 1,2,4-oxadiazolyl, benzimidazolyl, benzotriazolyl or an imidazopyridinyl (such as imidazo[4,5c]pyridinyl), each of which is unsubstituted or substituted by one or two of the same or different $C_{1-6}$ alkyl (for example $C_{1-4}$ alkyl; such as methyl), $CF_3$, OH (which may tautomerise to the keto form), $S(O)_2(C_{1-4}$ alkyl), $C(O)NH_2$, $C(O)NH(phenyl(C_{1-2}$ alkyl)) or phenyl($C_{1-2}$ alkyl); wherein the phenyl of the foregoing phenyl($C_{1-2}$ alkyl) groups is optionally substituted by halo, $C_{1-4}$ alkyl, $C_{1-4}$ alkoxy, cyano or $S(O)_2(C_{1-4}$ alkyl).

In a still further aspect $R^4$ is 1,2,4-triazolyl, thiazolyl, 1,2,4-oxadiazolyl, imidazolyl, 1,3-dihydro-2H-imidazolyl, 1,2,3-triazolyl or piperidinyl substituted as described above. In a further aspect $R^4$ is 1,2,4-triazolyl, thiazolyl, 1,2,4-oxadiazolyl, piperidinyl, benzimidazolyl, 1,3-dihydro-2H-benzimidazolyl, benzotriazolyl or an imidazopyridinyl (such as imidazo[4,5c]pyridinyl, 1,4,6,7-tetrahydro-5H-imidazo[4,5-c]pyridinyl or 4,5,6,7-tetrahydro-3H-imidazo[4,5-c]pyridinyl), each of which is unsubstituted or substituted by one or two of the same or different $C_{1-6}$ alkyl (for example $C_{1-4}$ alkyl; such as methyl), $C_{3-6}$ cycloalkyl, $C_{1-4}$ haloalkyl (for example $CF_3$ or $CHF_2$), OH (which may tautomerise to the keto form), oxo (which may tautomerise to the hydroxy form), $C_{1-4}$ alkyl substituted by heterocyclyl (which is itself optionally substituted by $S(O)_2(C_{1-4}$ alkyl)), $S(O)_2(C_{1-4}$ alkyl), $(C_{1-4}$ alkyl)C(O), $(C_{1-4}$ haloalkyl)C(O), $(C_{1-4}$ alkoxy)C(O), $C(O)NH_2$, $C(O)NH(C_{1-4}$ alkyl), $C(O)NH(phenyl(C_{1-2}$ alkyl)) or phenyl($C_{1-2}$ alkyl); wherein the phenyl of the foregoing phenyl($C_{1-2}$ alkyl) groups is optionally substituted by halo, $C_{1-4}$ alkyl, $C_{1-4}$ alkoxy, cyano or $S(O)_2(C_{1-4}$ alkyl).

In another aspect $R^4$ is 1,2,4-triazolyl, thiazolyl, 1,2,4-oxadiazolyl, imidazolyl or 1,2,3-triazolyl substituted as described above. In a further aspect $R^4$ is 1,2,4-triazolyl, thiazolyl, 1,2,4-oxadiazolyl, benzimidazolyl, benzotriazolyl or an imidazopyridinyl (such as imidazo[4,5c]pyridinyl), each of which is unsubstituted or substituted by one or two of the same or different $C_{1-6}$ alkyl (for example $C_{1-4}$ alkyl; such as methyl), $C_{3-6}$ cycloalkyl, $C_{1-4}$ haloalkyl (for example $CF_3$ or $CHF_2$), OH (which may tautomerise to the keto form), oxo (which may tautomerise to the hydroxy form), $S(O)_2(C_{1-4}$ alkyl), $(C_{1-4}$ alkyl)C(O), $C(O)NH_2$, $C(O)NH(C_{1-4}$ alkyl), $C(O)NH(phenyl(C_{1-2}$ alkyl)) or phenyl($C_{1-2}$ alkyl); wherein the phenyl of the foregoing phenyl($C_{1-2}$ alkyl) groups is optionally substituted by halo, $C_{1-4}$ alkyl, $C_{1-4}$ alkoxy, cyano or $S(O)_2(C_{1-4}$ alkyl).

In a further aspect the present invention provides a compound or formula (Ia):

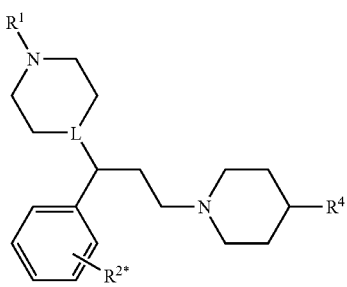

(Ia)

wherein L, $R^1$ and $R^4$ are as defined above; and $R^{2*}$ is 0, 1 or 2 of the same or different moieties selected from the group comprising: halo (such as chloro or fluoro) or $C_{1-4}$ haloalkyl (such as $CF_3$).

In a still further aspect the present invention provides a compound or formula (Ib):

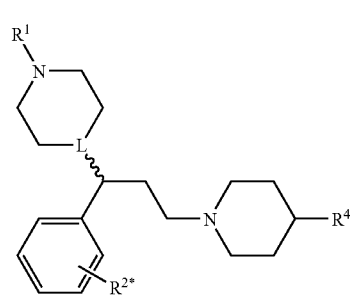

(Ib)

wherein L, $R^1$, $R^{2*}$ and $R^4$ are as defined above.

In another aspect the present invention provides a compound or formula (Ic):

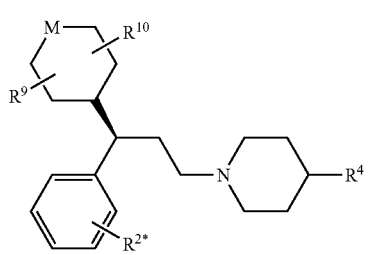

(Ic)

wherein M, $R^{2*}$, $R^4$, $R^9$ and $R^{10}$ are as defined above. In a further aspect M is oxygen.

In yet another aspect the present invention provides a compound or formula (Id):

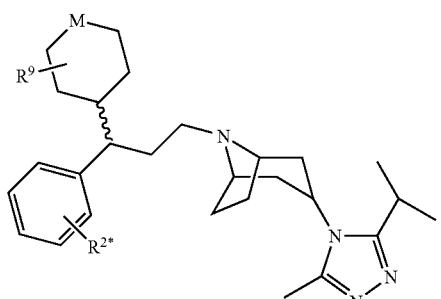

(Id)

wherein M, $R^{2*}$ and $R^9$ are as defined above. In another aspect $R^9$ is hydrogen.

In yet another aspect the present invention provides a compound or formula (Ie):

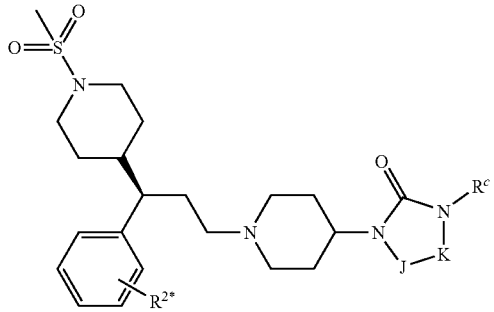

wherein $R^{2*}$ is as defined above; $R^c$ is $C_{1-6}$ alkyl [which is optionally substituted by halogen, CN, OH, $C_{1-4}$ alkoxy, $S(C_{1-4}$ alkyl), $S(O)(C_{1-4}$ alkyl), $S(O)_2(C_{1-4}$ alkyl) or heterocyclyl (itself optionally substituted by $C_{1-6}$ alkyl or $S(O)_2(C_{1-4}$ alkyl))]; and J-K is $CH_2$—$CH_2$, CH=CH or CH=C ($C_{1-4}$ alkyl); provided that when $R^c$ is an alkyl group substituted by a halogen, OH, $C_{1-4}$ alkoxy, $S(C_{1-4}$ alkyl), $S(O)(C_{1-4}$ alkyl) or $S(O)_2(C_{1-4}$ alkyl) substituent, said substituent is not bonded to the carbon of the alkyl group that is also bonded to the ring nitrogen of (Ie). When $R^c$ is heterocyclyl it is, for example, piperidinyl.

In yet another aspect the present invention provides a compound or formula (If):

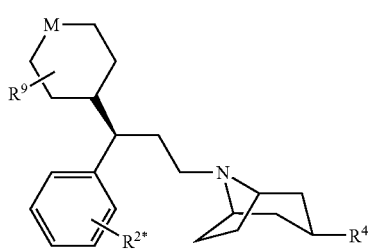

wherein $R^{2*}$, $R^4$ and $R^9$ are as defined above.

In yet another aspect the present invention provides a compound or formula (Ig):

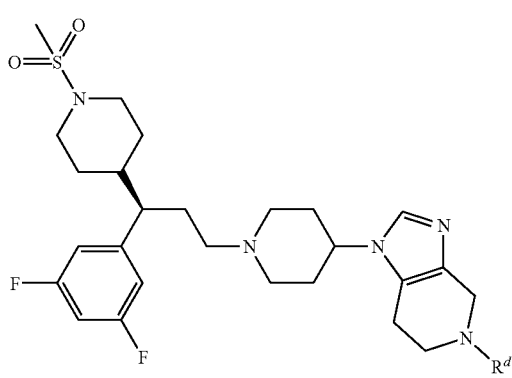

wherein $R^d$ is $C_{1-4}$ alkyl {which is optionally substituted by oxo, halogen, OR, $C_{1-4}$ alkoxy, $OCF_3$, $C(O)O(C_{1-4}$ alkyl), CN, $C(O)NH_2$, $C(O)NH(C_{1-4}$ alkyl), $C(O)N(C_{1-4}$ alkyl)$_2$, phenyl (itself optionally substituted by $S(O)_2(C_{1-4}$ alkyl)), $NH_2$, $NH(C_{1-4}$ alkyl) or $N(C_{1-4}$ alkyl)$_2$}, $C(O)(C_{1-4}$ alkyl) {wherein the alkyl is optionally substituted by $C_{1-4}$ alkoxy or fluoro}, $C(O)O(C_{1-4}$ alkyl), $C(O)NH_2$, $C(O)NH(C_{1-4}$ alkyl), $C(O)N(C_{1-4}$ alkyl)$_2$ or $S(O)_2(C_{1-4}$ alkyl) {wherein the alkyl is optionally substituted by fluoro}; provided that when $R^d$ is an alkyl group substituted by a oxo, halogen, OH, $C_{1-4}$ alkoxy, $OCF_3$, $NH_2$, $NH(C_{1-4}$ alkyl) or $N(C_{1-4}$ alkyl)$_2$ substituent, said substituent is not bonded to the carbon of the alkyl group that is also bonded to the ring nitrogen of (Ig).

In a further aspect of the invention $R^d$ is $C_{1-4}$ alkyl {which is optionally substituted by oxo, halogen, OH, $C_{1-4}$ alkoxy, $OCF_3$, $C(O)O(C_{1-4}$ alkyl), CN, $C(O)NH_2$, $C(O)NH(C_{1-4}$ alkyl), $C(O)N(C_{1-4}$ alkyl)$_2$, $NH_2$, $NH(C_{1-4}$ alkyl) or $N(C_{1-4}$ alkyl)$_2$}, $C(O)(C_{1-4}$ alkyl) {wherein the alkyl is optionally substituted by $C_{1-4}$ alkoxy or fluoro}, $C(O)O(C_{1-4}$ alkyl), $C(O)NH_2$, $C(O)NH(C_{1-4}$ alkyl), $C(O)N(C_{1-4}$ alkyl)$_2$ or $S(O)_2(C_{1-4}$ alkyl) {wherein the alkyl is optionally substituted by fluoro}; provided that when $R^d$ is an alkyl group substituted by a oxo, halogen, OH, $C_{1-4}$ alkoxy, $OCF_3$, $NH_2$, $NH(C_{1-4}$ alkyl) or $N(C_{1-4}$ alkyl)$_2$ substituent, said substituent is not bonded to the carbon of the alkyl group that is also bonded to the ring nitrogen of (Ig).

In yet another aspect the present invention provides a compound or formula (Ih):

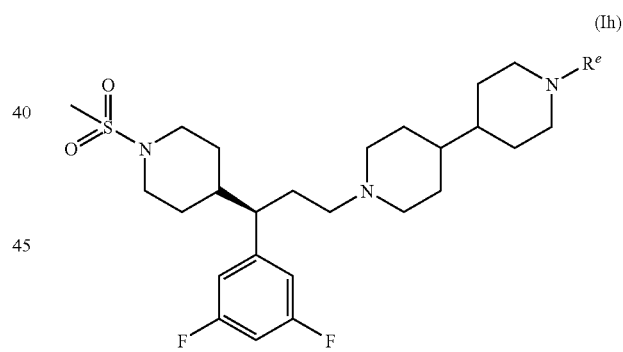

wherein $R^e$ is $C_{1-4}$ alkyl {which is optionally substituted by oxo, halogen, OH, $C_{1-4}$ alkoxy, $OCF_3$, $C(O)O(C_{1-4}$ alkyl), CN, $C(O)NH_2$, $C(O)NH(C_{1-4}$ alkyl), $C(O)N(C_{1-4}$ alkyl)$_2$, $NH_2$, $NH(C_{1-4}$ alkyl) or $N(C_{1-4}$ alkyl)$_2$}, $C(O)(C_{1-4}$ alkyl) {wherein the alkyl is optionally substituted by $C_{1-4}$ alkoxy or fluoro}, $C(O)O(C_{1-4}$ alkyl), $C(O)NH_2$, $C(O)NH(C_{1-4}$ alkyl), $C(O)N(C_{1-4}$ alkyl)$_2$ or $S(O)_2(C_{1-4}$ alkyl) {wherein the alkyl is optionally substituted by fluoro}; provided that when $R^e$ is an alkyl group substituted by a oxo, halogen, OH, $C_{1-4}$ alkoxy, $OCF_3$, $NH_2$, $NH(C_{1-4}$ alkyl) or $N(C_{1-4}$ alkyl)$_2$ substituent, said substituent is not bonded to the carbon of the alkyl group that is also bonded to the ring nitrogen of (Ih).

In yet another aspect the present invention provides a compound or formula (Ii):

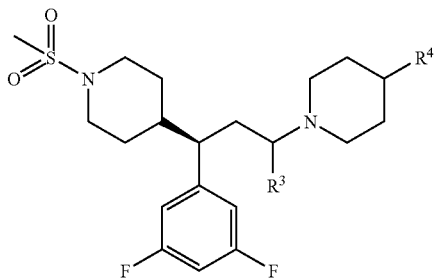

(Ii)

wherein R³ and R⁴ are as defined above.

In yet another aspect the present invention provides a compound or formula (Ij):

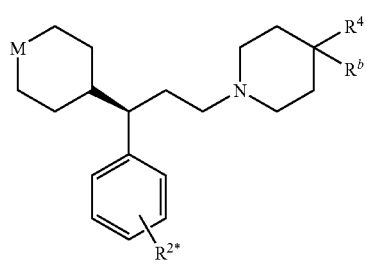

(Ij)

wherein R²*, R^b and R⁴ are as defined above.

In yet another aspect the present invention provides a compound or formula (Ik):

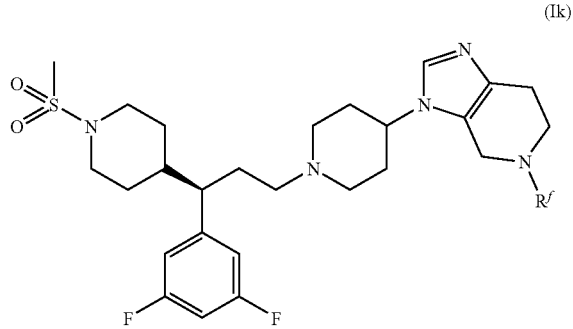

(Ik)

wherein R^f is $C_{1-4}$ alkyl {which is optionally substituted by oxo, halogen, OH, $C_{1-4}$ alkoxy, $OCF_3$, $C(O)O(C_{1-4}$ alkyl), CN, $C(O)NH_2$, $C(O)NH(C_{1-4}$ alkyl), $C(O)N(C_{1-4}$ alkyl)$_2$, $NH_2$, $NH(C_{1-4}$ alkyl) or $N(C_{1-4}$ alkyl)$_2$}, $C(O)(C_{1-4}$ alkyl) {wherein the alkyl is optionally substituted by $C_{1-4}$ alkoxy or fluoro}, $C(O)O(C_{1-4}$ alkyl), $C(O)NH_2$, $C(O)NH(C_{1-4}$ alkyl), $C(O)N(C_{1-4}$ alkyl)$_2$ or $S(O)_2(C_{1-4}$ alkyl) {wherein the alkyl is optionally substituted by fluoro}; provided that when R^f is an alkyl group substituted by a oxo, halogen, OH, $C_{1-4}$ alkoxy, $OCF_3$, $NH_2$, $NH(C_{1-4}$ alkyl) or $N(C_{1-4}$ alkyl)$_2$ substituent, said substituent is not bonded to the carbon of the alkyl group that is also bonded to the ring nitrogen of (Ik).

In a further aspect the present invention provides a compound wherein R⁴ is triazolyl (for example 1,2,4-triazolyl) optionally substituted by $C_{1-4}$ alkyl (such as methyl, ethyl, n-propyl or iso-propyl) or $C_{1-4}$ alkyl substituted by halogen (such as $CF_3$, $CHF_2$, $CH_2F$, $CH_2CF_3$ or $C_2F_5$).

In a still further aspect the present invention provides a compound wherein R⁴ is:

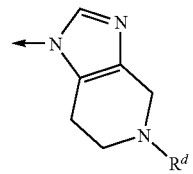

wherein R^d is as defined above. For example R^d is $C_{1-4}$ alkyl, $C(O)(C_{1-4}$ alkyl) {wherein the alkyl is optionally substituted by $C_{1-4}$ alkoxy or fluoro}, $C(O)O(C_{1-4}$ alkyl), or $S(O)_2(C_{1-4}$ alkyl) {wherein the alkyl is optionally substituted by fluoro}.

In a further aspect the present invention provides a compound of formula (I) wherein A is absent or $(CH_2)_2$; L is CH or N; M is $NR^1$, O or $S(O)_2$; R¹ is phenyl (optionally substituted by halogen), $S(O)_2R^5$ or $C(O)R^8$; R² is phenyl (optionally substituted by halogen or $CF_3$); R³ is hydrogen or $C_{1-4}$ alkyl; R⁴ is 1,2,4-triazolyl, 1,2,4-oxadiazolyl, imidazolyl, 1,2,3-triazolyl, 1,3-dihydro-2H-imidazolyl, imidazolidinyl or piperidinyl ring {optionally substituted by oxo, $C_{1-6}$ alkyl [itself optionally substituted by piperidinyl optionally substituted by $S(O)_2(C_{1-4}$ alkyl)], $CF_3$, $H_2NC(O)$, $S(O)_2(C_{1-4}$ alkyl), $C(O)(C_{1-4}$ fluoroalkyl), $C(O)(C_{1-4}$ alkoxy), (phenyl$C_{1-2}$ alkyl)HNC(O), benzyl [which is optionally substituted by $S(O)_2(C_{1-4}$ alkyl)] or phenyl [which is optionally substituted by $S(O)_2(C_{1-4}$ alkyl)]}, optionally fused to a benzene, pyridine or piperidine ring {any of said fused rings being optionally substituted by $C_{1-4}$ alkyl, $CF_3$ or $S(O)_2(C_{1-4}$ alkyl), $C(O)(C_{1-4}$ alkyl), $C(O)(C_{1-4}$ fluoroalkyl), $C(O)(C_{1-4}$ alkoxy) or benzyl [which is optionally substituted by $S(O)_2(C_{1-4}$ alkyl)]}; R⁵ and R⁸ are $C_{1-4}$ alkyl, phenyl (optionally substituted by halogen), $C_{1-4}$ fluoroalkyl, $C_{3-6}$ cycloalkyl (optionally substituted by halogen) or piperidinyl (optionally substituted by $S(O)_2(C_{1-4}$ alkyl), $C(O)(C_{1-4}$ alkyl) or benzyloxycarbonyl); and R⁹ and R¹⁰ are, independently, hydrogen or $C_{1-4}$ alkyl; R^b is hydrogen or $C_{1-4}$ alkyl.

In a still further aspect the present invention provides a compound of formula (I) wherein A is absent or $(CH_2)_2$; L is CH or N; M is $NR^1$ or O; R¹ is phenyl (optionally substituted by halogen), $S(O)_2R^5$ or $C(O)R^8$; R² is phenyl (optionally substituted by halogen or $CF_3$); R³ is hydrogen; R⁴ is 1,2,4-triazolyl, 1,2,4-oxadiazolyl, imidazolyl, 1,2,3-triazolyl or 1,3-dihydro-2H-imidazolyl ring {optionally substituted by oxo, $C_{1-6}$ alkyl, $H_2NC(O)$, (phenyl$C_{1-2}$ alkyl)HNC(O) or benzyl [which is optionally substituted by $S(O)_2(C_{1-4}$ alkyl)]}, optionally fused to a benzene or pyridine ring {either of which is optionally substituted by $CF_3$ or $S(O)_2(C_{1-4}$ alkyl)}; R⁵ and R⁸ are $C_{1-4}$ alkyl, phenyl (optionally substituted by halogen), $CF_3$, $C_{3-6}$ cycloalkyl (optionally substituted by halogen) or piperidinyl (optionally substituted by $S(O)_2(C_{1-4}$ alkyl), $C(O)(C_{1-4}$ alkyl) or benzyloxycarbonyl); and R⁹ and R¹⁰ are, independently, hydrogen or $C_{1-4}$ alkyl.

The compounds listed in Tables I, II, III IV, V, VI, VII, VIII, IX, X and XI illustrate the invention. In another aspect the present invention provides each individual compound recited in Table I, II, III, IV, V, VI, VII, VIII, IX, X and XI.

TABLE I

Table I comprises compounds of formula (Ia):

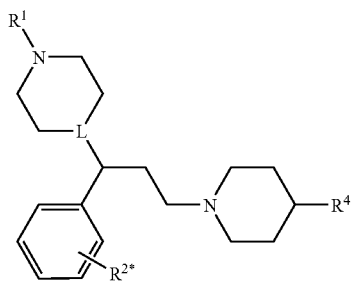

(Ia)

| Compound No | L | R²* | R¹ | R⁴ | LCMS MH⁺ |
|---|---|---|---|---|---|
| 1 | N | H | ethanesulphonyl | 5-methanesulphonylbenzimidazolyl | 574 |
| 2 | N | H | benzoyl | 5-methanesulphonylbenzimidazolyl | 586 |
| 3 | N | H | 4-chlorobenzyl | 5-methanesulphonylbenzimidazolyl | 620 |
| 4 | N | H | methanesulphonyl | 5-methanesulphonylbenzimidazolyl | 560 |
| 5 | CH | H | methanesulphonyl | 3-isopropyl-5-methyl-[1,2,4]triazol-4-yl | 488 |
| 6 | CH | H | 4-chlorobenzoyl | 3-isopropyl-5-methyl-[1,2,4]triazol-4-yl | 548 |
| 7 | CH | H | ethanesulphonyl | 3-isopropyl-5-methyl-[1,2,4]triazol-4-yl | 502 |
| 8 | N | H | 4-fluorophenyl | 5-methanesulphonylbenzimidazolyl | 576 |
| 9 | CH | H | methanesulphonyl | 4-[N-benzylaminocarbonyl]thiazol-2-yl | 581 |
| 10 | CH | H | methanesulphonyl | 4-[aminocarbonyl]thiazol-2-yl | 491 |
| 11 | CH | H | methanesulphonyl | 3-[4-methanesulphonylbenzyl]-[1,2,4]oxadiazol-5-yl | 601 |
| 12 | CH | H | methanesulphonyl | 3-Benzyl-[1,2,4]oxadiazol-5-yl | 523 |
| 13 | N | 3,5-F₂ | methanesulphonyl | 5-methanesulphonylbenzimidazolyl | 596 |
| 14 | N | H | benzenesulphonyl | 5-methanesulphonylbenzimidazolyl | 622 |

TABLE II

Table II comprises compounds of formula (Ib):

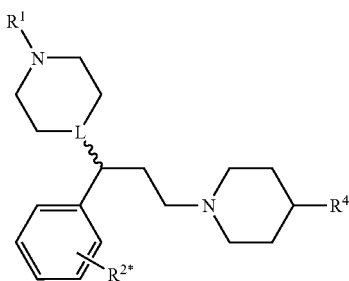

(Ib)

| Compound No | L | R²* | R¹ | Stereo chem | R⁴ | LCMS MH⁺ |
|---|---|---|---|---|---|---|
| 1 | N | H | benzenesulphonyl | S | 3-isopropyl-5-methyl-[1,2,4]triazol-4-yl | 551 |
| 2 | CH | H | methanesulphonyl | S or R | 3-isopropyl-5-methyl-[1,2,4]triazol-4-yl | 488 |
| 3 | CH | H | methanesulphonyl | R or S | 3-isopropyl-5-methyl-[1,2,4]triazol-4-yl | 488 |
| 4 | N | H | benzenesulphonyl | S | 4-[N-benzylaminocarbonyl]thiazol-2-yl | 644 |
| 5 | CH | 3,5-difluoro | methanesulphonyl | R | 5-methanesulphonylbenzimidazolyl | 595 |
| 6 | CH | 3-trifluoromethyl | methanesulphonyl | R | 5-methanesulphonylbenzimidazolyl | 627 |
| 7 | CH | H | methanesulphonyl | R | 5-methanesulphonylbenzimidazolyl | 559 |
| 8 | CH | H | 4,4-difluorocyclohexyl-CO | R | 3-isopropyl-5-methyl-[1,2,4]triazol-4-yl | 556 |
| 9 | CH | H | 4-piperidinylSO₂ | R | 3-isopropyl-5-methyl-[1,2,4]triazol-4-yl | 557 |
| 10 | CH | H | (N-MeSO₂-piperidin-4-yl)-SO₂ | R | 3-isopropyl-5-methyl-[1,2,4]triazol-4-yl | 635 |
| 11 | CH | H | N-acetylpiperidin-4-ylSO₂ | R | 3-isopropyl-5-methyl-[1,2,4]triazol-4-yl | 599 |
| 12 | CH | H | [piperidin-4-yl]CO | R | 3-isopropyl-5-methyl-[1,2,4]triazol-4-yl | 521 |
| 13 | CH | H | N-benzyloxycarbonyl-piperidin-4-ylCO | R | 3-isopropyl-5-methyl-[1,2,4]triazol-4-yl | 655 |
| 14 | CH | H | N-MeSO₂piperidin-4-ylCO | R | 3-isopropyl-5-methyl-[1,2,4]triazol-4-yl | 599 |
| 15 | CH | H | N-acetylpiperidin-4-ylCO | R | 3-isopropyl-5-methyl-[1,2,4]triazol-4-yl | 563 |
| 16 | N | H | benzenesulphonyl | S | 4-[aminocarbonyl]thiazol-2-yl | 554 |
| 17 | CH | 3,5-difluoro | methanesulphonyl | R | 1,3-dihydro-2H-benzimidazol-1-yl-2-one | |
| 18 | CH | 3,5-difluoro | methanesulphonyl | R | 5-CF₃—1H-1,2,3-benzotriazol-1-yl | |
| 19 | CH | 3,5-difluoro | methanesulphonyl | R | 3H-imidazo[4,5c]pyridin-3-yl | 518 |

TABLE II-continued

Table II comprises compounds of formula (Ib):

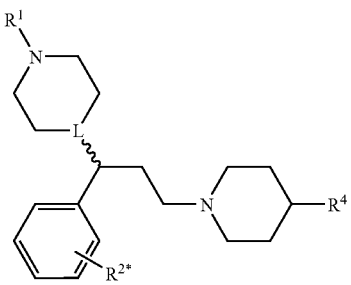

(Ib)

| Compound No | L | R² * | R¹ | Stereo chem | R⁴ | LCMS MH⁺ |
|---|---|---|---|---|---|---|
| 20 | CH | 3,5-difluoro | methanesulphonyl | R | 2-methyl-3H-imidazo[4,5c]pyridin-3-yl | 532 |
| 21 | CH | 3,5-difluoro | methanesulphonyl | R | 2-methyl-5-methanesulphonylbenzimidazolyl | 609 |
| 22 | CH | 3,5-difluoro | methanesulphonyl | R | 3-isopropyl-5-methyl-[1,2,4]triazol-4-yl | 524 |
| 23 | CH | 3,5-difluoro | methanesulphonyl | R | 1H-imidazo[4,5c]pyridin-1-yl | 518 |
| 24 | N | H | 3-methylphenyl | S | 3-isopropyl-5-methyl-[1,2,4]triazol-4-yl | 501 |
| 25 | CH | 3,5-difluoro | methanesulphonyl | R | 3-trifluoromethyl-5-methyl-[1,2,4]triazol-4-yl | 550 |
| 26 | CH | 3-fluoro | methanesulphonyl | R | 5-methanesulphonylbenzimidazolyl | 577 |
| 27 | CH | 3,5-difluoro | methanesulphonyl | R | benzimidazol-1-yl | 517 |
| 28 | CH | 3,5-difluoro | methanesulphonyl | R | 5-(methylsulfonyl)-4,5,6,7-tetrahydro-3H-imidazo[4,5-c]pyridin-3-yl | 600 |
| 29 | CH | 3,5-difluoro | methanesulphonyl | R | 3-acetyl-5-methyl-[1,2,4]triazol-4-yl | 510 |

TABLE III

Table III comprises compounds of formula (Ic):

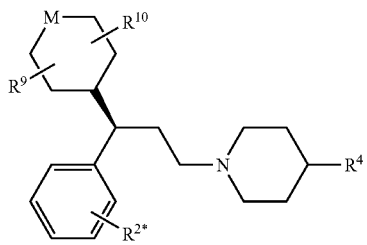

(Ic)

| Compound No | R² * | R⁴ | M | R⁹ | R¹⁰ | LCMS MH⁺ |
|---|---|---|---|---|---|---|
| 1 | 3,5-difluoro | 3-isopropyl-5-methyl-[1,2,4]triazol-4-yl | O | H | H | 447 |
| 2 | 3,5-difluoro | 5-methanesulphonylbenzimidazolyl | O | H | H | 518 |
| 3 | 3,5-dichloro | 5-methanesulphonylbenzimidazolyl | O | H | H | 550 |
| 4 | 3,5-difluoro | 5-methanesulphonylbenzimidazolyl | O | 2-CH₃ (S) | H | 532 |
| 5 | 3,5-difluoro | 5-methanesulphonylbenzimidazolyl | O | 2-CH₃ (cis to R¹⁰) | 5-CH₃ | 546 |
| 6 | 3,5-difluoro | 3-isopropyl-5-methyl-[1,2,4]triazol-4-yl | O | 2-Me (S) | H | 461 |
| 7 | 3,5-difluoro | 3-isopropyl-5-methyl-[1,2,4]triazol-4-yl | SO₂ | H | H | 495 |

TABLE IV

Table IV comprises compounds of formula (Id):

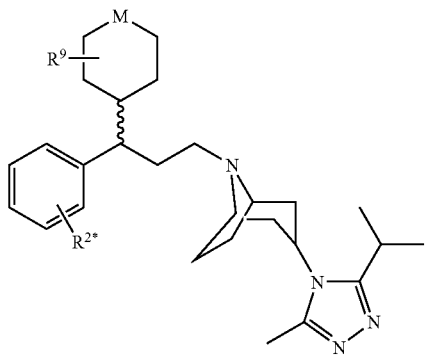

(Id)

| Compound No | $R^{2*}$ | M | $R^9$ | Stereochemistry | LCMS M + H |
|---|---|---|---|---|---|
| 1 | H | trifluoromeethanesulphonyl-N | H | RS | 568 |
| 2 | H | methanesulphonyl-N | H | RS | 514 |
| 3 | 3,5-difluoro | methanesulphonyl-N | H | R | 550 |
| 4 | 3,5-difluoro | O | H | R | 473 |
| 5 | 3,5-difluoro | SO2 | H | R | 521 |
| 6 | 3-fluoro | methanesulphonyl-N | H | R | 554 |
| 7 | 3,5-difluoro | O | 2-Me (S) | R | 487 |
| 8 | 3,5-difluoro | trifluoromethanesulphonyl-N | H | R | 604 |

TABLE V

Table V comprises compounds of formula (Ie):

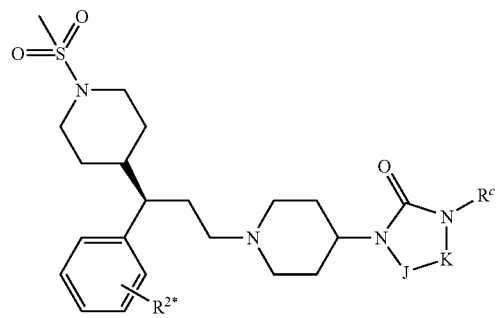

(Ie)

| Compound No | $R^{2*}$ | J—K | $R^c$ | M + H |
|---|---|---|---|---|
| 1 | 3,5-F$_2$ | —CH$_2$—CH$_2$— | hydrogen | 485 |
| 2 | 3,5-F$_2$ | —CH$_2$—CH$_2$— | 4-methanesulphonylbenzyl | 653 |
| 3 | 3,5-F$_2$ | —CH$_2$—CH$_2$— | 4-methanesulphonylphenyl | 639 |
| 4 | 3,5-F$_2$ | —CH$_2$—CH$_2$— | (N-methanesulphonylpiperidin-4-yl)-methyl | 660 |
| 5 | 3,5-F$_2$ | —CH=CH— | hydrogen | 483 |
| 6 | 3,5-F$_2$ | —CH=CH— | 4-methanesulphonylbenzyl | 651 |
| 7 | 3,5-F$_2$ | —CH=CH— | 4-methanesulphonylphenyl | 637 |
| 8 | 3,5-F$_2$ | —CH=CH— | (N-methanesulphonylpiperidin-4-yl)-methyl | 658 |
| 9 | 3,5-F$_2$ | —CH=C(Me)— | hydrogen | 497 |
| 10 | 3,5-F$_2$ | —CH=C(Me)— | 4-methanesulphonylbenzyl | 665 |
| 11 | 3,5-F$_2$ | —CH=C(Me)— | 4-methanesulphonylphenyl | 651 |

TABLE VI

Table VI comprises compounds of formula (If):

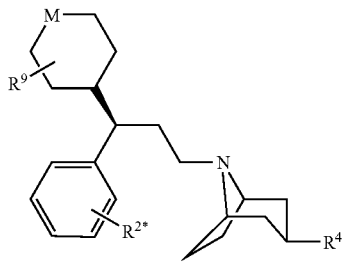

(If)

| Compound No. | M | endo/exo | R²* | R⁹ | R⁴ | M + H |
|---|---|---|---|---|---|---|
| 1 | MeSO₂N | exo | 3,5-diF₂ | H | 5-methanesulphonylbenzimidazolyl | 621 |
| 2 | MeSO₂N | endo | 3,5-diF₂ | H | 5-methanesulphonylbenzimidazolyl | 621 |
| 3 | O | exo | 3,5-diF₂ | H | 5-methanesulphonylbenzimidazolyl | 544 |
| 4 | O | exo | 3,5-diF₂ | 2-Me (S) | 5-methanesulphonylbenzimidazolyl | 558 |
| 5 | MeSO₂N | exo | 3,5-diF₂ | H | 3-trifluoromethyl-5-methyl-[1,2,4]triazol-4-yl | 550 |
| 6 | MeSO₂N | exo | 3,5-diF₂ | H | 3-difluoromethyl-5-methyl-[1,2,4]triazol-4-yl | 558 |
| 7 | MeSO₂N | exo | 3,5-diF₂ | H | 3-hydroxymeethyl-5-meethyl-[1,2,4]triazol-4-yl | 538 |
| 8 | MeSO₂N | exo | 3-F | H | 3-trifluoromethyl-5-methyl-[1,2,4]triazol-4-yl | 558 |
| 9 | MeSO₂N | exo | 3,5-diF₂ | H | 3,5-dimethyl-[1,2,4]triazol-4-yl | 522 |
| 10 | MeSO₂N | exo | 3,5-diF₂ | H | 3-ethyl-5-methyl-[1,2,4]triazol-4-yl | 536 |
| 11 | MeSO₂N | exo | 3,5-diF₂ | H | 1-(1H-imidazo[4,5-c]pyridyl) | 544 |
| 12 | MeSO₂N | exo | 3,5-diF₂ | H | Methyl-1-(1,4,6,7-tetrahydro-5H-imidazo[4,5-c]pyridyl-5-carboxylate) | 606 |
| 13 | meSO₂N | endo | 3,5-diF₂ | H | 1-(1H-imidazo[4,5-c]pyridyl) | 544 |
| 14 | MeSO₂N | exo | 3,5-diF₂ | H | 3-cyclopropyl-5-methyl-[1,2,4]triazol-4-yl | 548 |

TABLE VII

Table VII comprises compounds of formula (Ig):

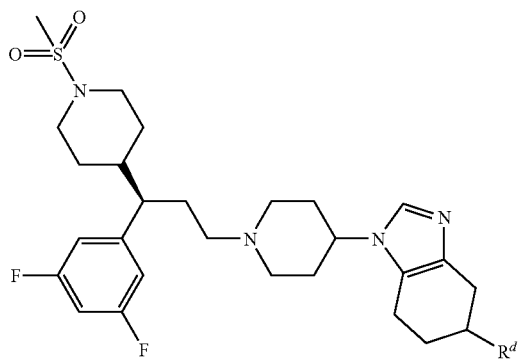

(Ig)

| Compound No | Rᵈ | M + H |
|---|---|---|
| 1 | hydrogen | 522 |
| 2 | methanesulphonyl | 600 |
| 3 | 2,2,2-trifluoropropionyl | 632 |
| 4 | acetyl | 564 |
| 5 | methoxycarbonyl | 580 |
| 6 | isopropyl | 564 |
| 7 | 4-methanesulphonylbenzyl | 690 |
| 8 | isopropyloxycarbonyl | 608 |
| 9 | N-methylcarboxamido | 579 |

TABLE VIII

Table VIII comprises compounds of formula (Ih):

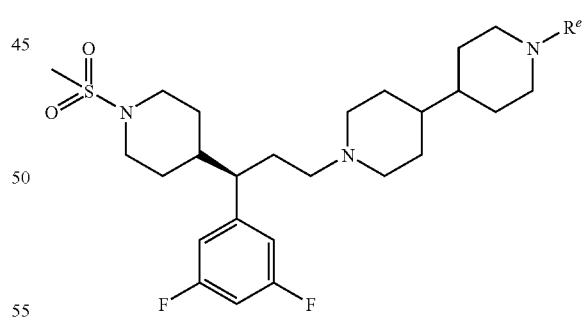

(Ih)

| Compound No | Rᵉ | M + H |
|---|---|---|
| 1 | tert-butoxycarbonyl | 584 |
| 2 | trifluoromethylcarbonyl | 580 |
| 3 | methanesulphonyl | 562 |

TABLE IX

Table IX comprises compounds of formula (Ii):

(Ii)

| Compound No | $R^3$ | $R^4$ | M + H |
|---|---|---|---|
| 1 | mthyl (more polar isomer) | 3-isopropyl-5-methyl-[1,2,4]triazol-4-yl | 538 |
| 2 | methyl (less polar isomer) | 3-isopropyl-5-methyl-[1,2,4]triazol-4-yl | 538 |

TABLE X

Table X comprises compounds of formula (Ij):

(Ij)

| Compound No | $R^{2*}$ | M | $R^b$ | $R^4$ | M + H |
|---|---|---|---|---|---|
| 1 | 3,5-$F_2$ | $MeSO_2N$ | methyl | 5-methanesulphonylbenzimidazolyl | 609 |

TABLE XI

Table XI comprises compounds of formula (Ik):

(Ik)

| Compound No | $R^f$ | M + H |
|---|---|---|
| 1 | methanesulphonyl | 600 |

A compound of the invention can be prepared by reductive amination of a compound of formula (II):

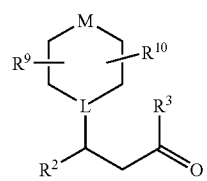

(II)

with a compound of formula (III):

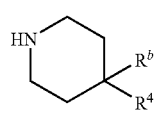

(III)

in the presence of $NaBH(OAc)_3$ (wherein Ac is $C(O)CH_3$) and acetic acid, in a suitable solvent (such as a $C_{1-6}$ aliphatic alcohol, for example ethanol) at room temperature (for example 10-30° C.). A compound of formula (II), wherein L is CH, can be prepared as shown in Scheme 1 below. (In Scheme 1 Ac is acetyl; Et is ethyl; and LDA is lithium diisopropylamide.) A compound of formula (II), wherein L is N, can be prepared as shown in Scheme 2 below.

A compound of formula (III) can be prepared by removal of the protecting group (PG) from a compound of formula (IV):

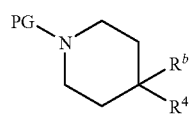
(IV)

for example where PG is benzyloxylcarbonyl or benzyl removal may be effected by hydrogenation (for example hydrogen in the presence of palladium on carbon catalyst); where PG is tert-butyloxycarbonyl removal may be effected by treatment with acid (such as hydrochloric acid or trifluoroacetic acid).

A compound of formula (IVa):

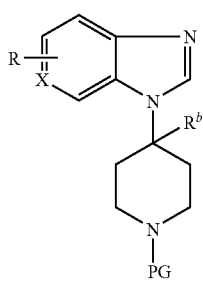
(IVa)

wherein PG is a protecting group; X is N, N-oxide, CH or a carbon substituted by halogen, cyano, $C_{1-4}$ alkyl, $C_{1-4}$ alkoxy, $CF_3$, $OCF_3$, $S(C_{1-4}$ alkyl), $S(O)(C_{1-4}$ alkyl) or $S(O)_2(C_{1-4}$ alkyl); and R is hydrogen, halogen, cyano, $C_{1-4}$ alkyl, $C_{1-4}$ alkoxy, $CF_3$, $OCF_3$, $S(C_{1-4}$ alkyl), $S(O)(C_{1-4}$ alkyl) or $S(O)_2$ ($C_{1-4}$ alkyl); can be made by first reducing a compound of formula (Va):

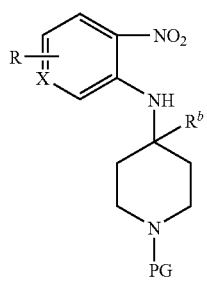
(Va)

and then cyclising the product so formed. (For example cyclising in the presence of trimethylorthoformate and para-toluenesuphonic acid monohydrate.)

Variants of compounds of formulae (IVa) and (Va) in which the group X occupies an alternative position in the aromatic ring can be prepared in a similar manner.

A compound of formula (Va) can be prepared by coupling a compound of formula (VIa):

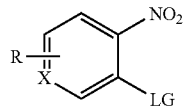
(VIa)

wherein LG is a leaving group (such as fluorine), with a compound of formula (VII):

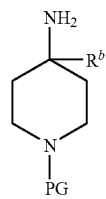
(VII)

in the presence of a base. A compound of formula (VIa) can be made by nitration of the respective chloroheteroaryl or respective chloroheteroaryl N-oxide (followed by reduction to remove the N-oxide); or by chlorination of an oxo-nitro-heteroaryl (such as 3-nitropyridin-4-one).

A compound of formula (IVb):

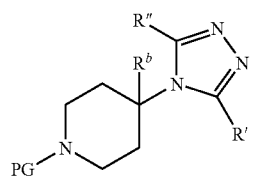
(IVb)

wherein PG is a protecting group; and R' and R" are, independently, hydrogen, $C_{1-6}$ alkyl or benzyl [which is optionally substituted by halogen, $C_{1-4}$ alkyl, $C_{1-4}$ alkoxy, $CF_3$, $OCF_3$, $S(C_{1-4}$ alkyl) or $S(O)_2(C_{1-4}$ alkyl)]; can be prepared from a compound of formula (Vb):

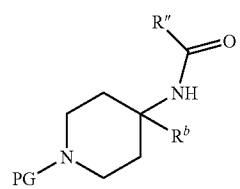
(Vb)

using a "one-pot", two-step procedure by first activating the amide with, for example, phosphorous oxychloride in the presence of a base (such as pyridine), and reacting the product so formed with an acyl hydrazide, then by cyclising in the presence of an acid at elevated temperature (such as para-toluenesuphonic acid in refluxing toluene).

A compound of formula (Vb) can be prepared from a compound of formula (VII) by reaction with an activated carboxylic acid or with a carbonyl chloride in the presence of a base.

A compound of formula (IVc), wherein PG and R' are as defined above, can be prepared by first activating the acid of a compound of formula (Vc) and reacting with an N-hydroxy-amidine RC(NOH)NH$_2$, then by cyclisation under elevated temperature in a suitable solvent (such as dioxin).

(Vc)

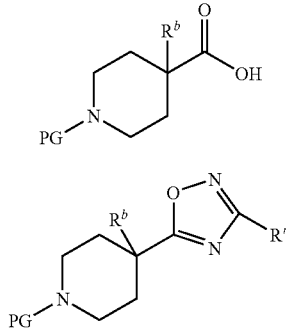

(IVc)

A compound of formula (IVd), wherein PG and R' are as defined above, can be prepared by addition of azide to a compound of formula (Vd) then by alkylation of the product and separation of the N1 and N2 isomers so formed (N2 isomer shown).

(Vd)

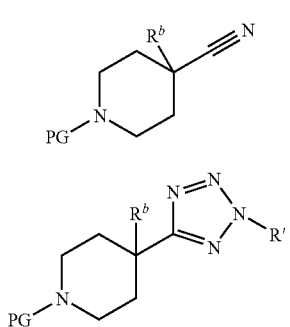

(IVd)

Compounds of formulae (IVe) and (IVf), wherein PG, R' and R" are as defined above, can be prepared by reaction of a compound of formula (Ve) with an alkyl hydrazine R'NHNH$_2$. A compound of formula (Ve) can be made by condensation of a compound of formula (VIe) with an ester R"C(O)$_2$R* (wherein R* is C$_{1-6}$ alkyl).

(IVe)

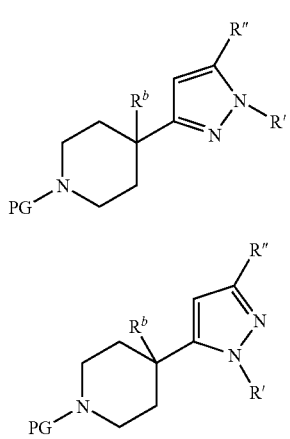

(IVf)

-continued (Ve)

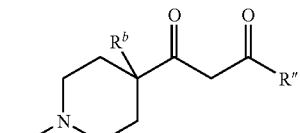

(VIe)

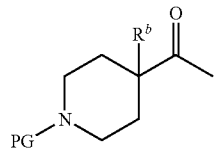

A compound of formula (IVg), wherein PG, R' and R" are as defined above, can be prepared by reaction of a compound of formula (Vg) with a 1,3-di-ketone R"C(O)CH$_2$C(O)R'.

(Vg)

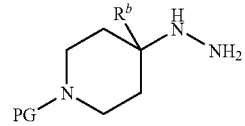

(IVg)

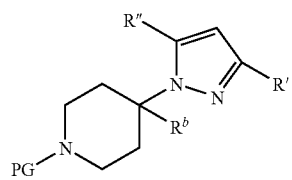

A compound of the invention can be prepared by alkylation of a compound of formula (VIII) or (VIIIa):

(VIII)

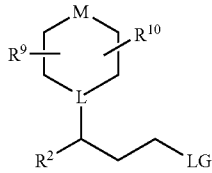

(VIIIa)

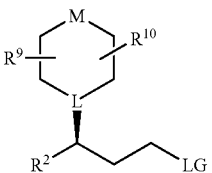

wherein LG is a leaving group; with a compound of formula (III)

(III)

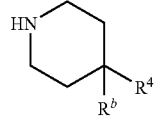

in the presence of a suitable base (such as potassium carbonate or triethylamine) in a suitable solvent (such as acetonitrile or THF) at room temperature (for example 10-30° C.).

The starting materials for these preparative methods are either commercially available or can be prepared by literature methods, adapting literature methods or the Examples below, or by following or adapting Methods herein described.

In a further aspect the invention provides processes for preparing the compounds of the invention. Many of the intermediates in the processes are novel and these are provided as further features of the invention.

The compounds of the invention have activity as pharmaceuticals, in particular as modulators (such as agonists, partial agonists, inverse agonists or antagonists) of chemokine receptor (for example CCR5) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

The compounds of the present invention are also of value in inhibiting the entry of viruses (such as human immunodeficiency virus (HIV)) into target calls and, therefore, are of value in the prevention of infection by viruses (such as HIV), the treatment of infection by viruses (such as HIV) and the prevention and/or treatment of acquired immune deficiency syndrome (AIDS).

According to a further feature of the invention there is provided a compound of the invention, or a pharmaceutically acceptable salt thereof, for use in a method of treatment of a warm blooded animal (such as man) by therapy (including prophylaxis).

According to a further feature of the present invention there is provided a method for modulating chemokine receptor activity (for example CCR5 receptor activity) in a warm blooded animal, such as man, in need of such treatment, which comprises administering to said animal an effective amount of a compound of the present invention, or a pharmaceutically acceptable salt thereof.

The present invention also provides the use of a compound of the invention, or a pharmaceutically acceptable salt thereof, as a medicament, for example a medicament for the treatment of transplant rejection, respiratory disease, psoriasis or rheumatoid arthritis (such as rheumatoid arthritis). [Respiratory disease is, for example, COPD, asthma {such as bronchial, allergic, intrinsic, extrinsic or dust asthma, particularly chronic or inveterate asthma (for example late asthma or airways hyper-responsiveness)} or rhinitis {acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis}; and is particularly asthma or rhinitis].

In another aspect the present invention provides the use of a compound of the invention, or a pharmaceutically acceptable salt thereof, in the manufacture of a medicament for use in therapy (for example modulating chemokine receptor activity (such as CCR5 receptor activity (for example rheumatoid arthritis)) in a warm blooded animal, such as man).

The invention also provides a compound of the invention, or a pharmaceutically acceptable salt thereof, for use as a medicament, for example a medicament for the treatment of rheumatoid arthritis.

In another aspect the present invention provides the use of a compound of the invention, or a pharmaceutically acceptable salt thereof, in the manufacture of a medicament for use in therapy (for example modulating chemokine receptor activity (such as CCR5 receptor activity (for example rheumatoid arthritis)) in a warm blooded animal, such as man).

The invention further provides the use of a compound of the invention, or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofulous rhinitis; seasonal rhinitis including rhinitis nervosa (hay fever) or vasomotor rhinitis; sarcoidosis; farmer's lung and related diseases; nasal polyposis; fibroid lung or idiopathic interstitial pneumonia;

(2) (bone and joints) arthritides including rheumatic, infectious, autoimmune, seronegative spondyloarthropathies (such as ankylosing spondylitis, psoriatic arthritis or Reiter's disease), Behçet's disease, Sjogren's syndrome or systemic sclerosis;

(3) (pain and connective tissue remodelling of musculoskeletal disorders due to injury [for example sports injury] or disease) arthitides (for example rheumatoid arthritis, osteoarthritis, gout or crystal arthropathy), other joint disease (such as intervertebral disc degeneration or temporomandibular joint degeneration), bone remodelling .disease (such as osteoporosis, Paget's disease or osteonecrosis), polychondritits, scleroderma, mixed connective tissue disorder, spondyloarthropathies or periodontal disease (such as periodontitis);

(4) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(5) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(6) (Allograft rejection) acute and chronic following, for example, transplantation of kidney, heart, liver, lung, bone marrow, skin or cornea; or chronic graft versus host disease; and/or (7) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, cosinophilia fascitis, hyper IgE syndrome, leprosy (such as lepromatous leprosy), Peridontal disease, Sezary syndrome, idiopathic thrombocytopenia pupura or disorders of the menstrual cycle;

in a warm blooded animal, such as man.

The present invention further provides a method of treating a chemokine mediated disease state (for example a CCR5 mediated disease state) in a warm blooded animal, such as man, which comprises administering to a mammal in need of such treatment an effective amount of a compound of the invention, or a pharmaceutically acceptable salt thereof.

In order to use a compound of the invention, or a pharmaceutically acceptable salt thereof, for the therapeutic treatment of a warm blooded animal, such as man, in particular modulating chemokine receptor (for example CCR5 receptor) activity, said ingredient is normally formulated in accordance with standard pharmaceutical practice as a pharmaceutical composition.

Therefore in another aspect the present invention provides a pharmaceutical composition which comprises a compound of the invention, or a pharmaceutically acceptable salt thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will comprise, for example, from 0.05 to 99% w (per cent by weight), such as from 0.05 to 80% w, for example from 0.10 to 70% w (such as from 0.10 to 50% w), of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 mgkg$^{-1}$ to 100 mgkg$^{-1}$ of the compound, for example in the range of 0.1 mgkg$^{-1}$ to 20 mgkg$^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of the invention, or a pharmaceutically acceptable salt thereof or a solvent thereof (hereafter Compound X), for therapeutic or prophylactic use in humans:

| (a) | |
|---|---|
| Tablet I | mg/tablet |
| Compound X | 100 |
| Lactose Ph.Eur. | 179 |
| Croscarmellose sodium | 12.0 |

-continued

| (a) | |
|---|---|
| Tablet I | mg/tablet |
| Polyvinylpyrrolidone | 6 |
| Magnesium stearate | 3.0 |

| (b) | |
|---|---|
| Tablet II | mg/tablet |
| Compound X | 50 |
| Lactose Ph.Eur. | 229 |
| Croscarmellose sodium | 12.0 |
| Polyvinylpyrrolidone | 6 |
| Magnesium stearate | 3.0 |

| (c) | |
|---|---|
| Tablet III | mg/tablet |
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

| (d) | |
|---|---|
| Capsule | mg/capsule |
| Compound X | 10 |
| Lactose Ph.Eur. | 389 |
| Croscarmellose sodium | 100 |
| Magnesium stearate | 1.0 |

| (e) | |
|---|---|
| Injection I | (50 mg/mL) |
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)-(c) may be enteric coated by conventional means, for example to provide a coating of cellulose acetate phthalate.

The invention further relates to combination therapies or compositions wherein a compound of the invention, or a pharmaceutically acceptable salt thereof, or a pharmaceutical composition comprising a compound of the invention, or a pharmaceutically acceptable salt thereof, is administered concurrently (possibly in the same composition) or sequentially with an agent for the treatment of any one of the above disease states.

In particular, for the treatment of the inflammatory diseases rheumatoid arthritis, psoriasis, inflammatory bowel disease, COPD, asthma and allergic rhinitis a compound of the invention can be combined with a TNF-α inhibitor (such as an anti-TNF monoclonal antibody (such as Remicade, CDP-870 and D$_2$E$_7$.), or a TNF receptor immunoglobulin molecule (such as Enbrel.reg.)), a non-selective COX-1/COX-2 inhibitor (such as piroxicam or diclofenac; a propionic acid such as naproxen, flubiprofen, fenoprofen, ketoprofen or ibuprofen; a fenamate such as mefenamic acid, indomethacin, sulindac or apazone; a pyrazolone such as phenylbutazone; or a salicylate such as aspirin), a COX-2 inhibitor (such as meloxicam, celecoxib, rofecoxib, valdecoxib or etoricoxib) low dose methotrexate, lefunomide; ciclesonide; hydroxychloroquine, d-penicillamine or auranofin, or parenteral or oral gold.

The present invention still further relates to the combination of a compound of the invention together with:
- a leukotriene biosynthesis inhibitor, a 5-lipoxygenase (5-LO) inhibitor or a 5-lipoxygenase activating protein (FLAP) antagonist, such as zileuton, ABT-761, fenleuton, tepoxalin, Abbott-79175, Abbott-85761, an N-(5-substituted)-thiophene-2-alkylsulfonamide, a 2,6-di-tert-butylphenol hydrazones, a methoxytetrahydropyran such as Zeneca ZD-2138, SB-210661, a pyridinyl-substituted 2-cyanonaphthalene compound such as L-739,010; a 2-cyanoquinoline compound such as L-746,530; an indole or quinoline compound such as MK-591, MK-886 or BAY x 1005;
- a receptor antagonist for a leukotriene LTB$_4$., LTC$_4$., LTD$_4$. or LTE$_4$. selected from the group consisting of a phenothiazin-3-one such as L-651,392; an amidino compound such as CGS-25019c; a benzoxalamine such as ontazolast; a benzenecarboximidamide such as BIIL 284/260; or a compound such as zafirlukast, ablukast, montelukast, pranlukast, verlukast (MK-679), RG-12525, Ro-245913, iralukast (CGP 45715A) or BAY x 7195;
- a PDE4 inhibitor including an inhibitor of the isoform PDE4D;
- an antihistaminic H$_1$. receptor antagonist such as cetirizine, loratadine, desloratadine, fexofenadine, astemizole, azelastine or chlorpheniramine;
- a gastroprotective H$_2$. receptor antagonist;
- an α$_1$.- and α$_2$.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride or ethylnorepinephrine hydrochloride;
- an anticholinergic agent such as ipratropium bromide, tiotropium bromide, oxitropium bromide, pirenzepine or telenzepine;
- a β$_1$.- to β$_4$.-adrenoceptor agonist such as metaproterenol, isoproterenol, isoprenaline, albuterol, salbutamol, formoterol, salmeterol, terbutaline, orciprenaline, bitolterol mesylate or pirbuterol, or a methylxanthanine including theophylline and aminophylline; sodium cromoglycate; or a muscarinic receptor (M1, M2, and M3) antagonist;
- an insulin-like growth factor type I (IGF-1) mimetic;
- an inhaled glucocorticoid with reduced systemic side effects, such as prednisone, prednisolone, flunisolide, triamcinolone acetonide, beclomethasone dipropionate, budesonide, fluticasone propionate or mometasone furoate;
- an inhibitor of a matrix metalloprotease (MMP), such as a stromelysin, a collagenase, or a gelatinase or aggrecanase; such as collagenase-1 (MMP-1), collagenase-2 (MMP-8), collagenase-3 (MMP-13), stromelysin-1 (MMP-3), stromelysin-2 (MMP-10), and stromelysin-3 (MMP-11) or MMP-12;
- a modulator of chemokine receptor function such as CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 (for the C-X-C family) and CX$_3$CR1 for the C-X$_3$-C family;
- an osteoporosis agent such as roloxifene, droloxifene, lasofoxifene or fosomax;
- an immunosuppressant agent such as FK-506, rapamycin, cyclosporine, azathioprine or methotrexate;
- a compound useful in the treatment of AIDS and/or HIV infection for example: an agent which prevents or inhibits the viral protein gp120 from engaging host cell CD4 {such as soluble CD4 (recombinant); an anti-CD4 antibody (or modified/recombinant antibody) for example PRO542; an anti-group 120 antibody (or modified/recombinant antibody); or another agent which interferes with the binding of group 120 to CD4 for example BMS806}; an agent which prevents binding to a chemokine receptor, other than CCR5, used by the HIV virus {such as a CXCR4 agonist or antagonist or an anti-CXCR4 antibody}; a compound which interferes in the fusion between the HIV viral envelope and a cell membrane {such as an anti-group 41 antibody; enfuvirtide (T-20) or T-1249}; an inhibitor of DC-SIGN (also known as CD209) {such as an anti-DC-SIGN antibody or an inhibitor of DC-SIGN binding}; a nucleoside/nucleotide analogue reverse transcriptase inhibitor {for example zidovudine (AZT), nevirapine, didanosine (ddI), zalcitabine (ddC), stavudine (d4T), lamivudine (3TC), abacavir, adefovir or tenofovir (for example as free base or as disoproxil fumarate)}; a non-nucleoside reverse transcriptase inhibitor {for example nevirapine, delavirdine or efavirenz}; a protease inhibitor {for example ritonavir, indinavir, saquinavir (for example as free base or as mesylate salt), nelfinavir (for example as free base or as mesylate salt), amprenavir, lopinavir or atazanavir (for example as free base or as sulphate salt)}; a ribonucleotide reductase inhinbitor {for example hydroxyurea}; or an antiretroviral {for example emtricitabine}; or,
- an existing therapeutic agent for the treatment of osteoarthritis, for example a non-steroidal anti-inflammatory agent (hereinafter NSAID's) such as piroxicam or diclofenac, a propionic acid such as naproxen, flubiprofen, fenoprofen, ketoprofen or ibuprofen, a fenamate such as mefenamic acid, indomethacin, sulindac or apazone, a pyrazolone such as phenylbutazone, a salicylate such as aspirin, a COX-2 inhibitor such as celecoxib, valdecoxib, rofecoxib or etoricoxib, an analgesic or intra-articular therapy such as a corticosteroid or a hyaluronic acid such as hyalgan or synvisc, or a P2X7 receptor antagonist.

The present invention still further relates to the combination of a compound of the invention together with: (i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitor including a VLA-4 antagonist; (vi) a cathepsin; (vii) a MAP kinase inhibitor; (viii) a glucose-6 phosphate dehydrogenase inhibitor; (ix) a kinin-B.sub1.- and B.sub2.-receptor antagonist; (x) an anti-gout agent, e.g., colchicine; (xi) a xanthine oxidase inhibitor, e.g., allopurinol; (xii) an uricosuric agent, e.g., probenecid, sulfinpyrazone or benzbromarone; (xiii) a growth hormone secretagogue; (xiv) a transforming growth factor (TGFβ); (xv) a platelet-derived growth factor (PDGF); (xvi) a fibroblast growth factor, e.g., basic fibroblast growth factor (bFGF); (xvii) a granulocyte macrophage colony stimulating factor (GM-CSF); (xviii) a capsaicin cream; (xix) a Tachykinin NK.sub1. and NK.sub3. receptor antagonist selected from the group consisting of NKP-608C; SB-233412 (talnetant); and D-4418; (xx) an elastase inhibitors selected from the group consisting of UT-77 and ZD-0892; (xxi) a TNFα converting enzyme inhibitor (TACE); (xxii) an induced nitric oxide synthase inhibitor (iNOS); or (xxiii) a chemoattractant receptor-homologous molecule expressed on TH2 cells (a CRTH2 antagonist).

The invention will now be illustrated by the following non-limiting Examples in which, unless stated otherwise:

(i) temperatures are given in degrees Celsius (° C.); operations were carried out at room or ambient temperature, that is, at a temperature in the range of 18-25° C.;

(ii) organic solutions were dried over anhydrous magnesium sulfate; evaporation of solvent was carried out using a rotary evaporator under reduced pressure (600-4000 Pascals; 4.5-30 mm Hg) with a bath temperature of up to 60° C.;

(iii) chromatography unless otherwise stated means flash chromatography on silica gel; thin layer chromatography (TLC) was carried out on silica gel plates; where a "Bond Elut" column is referred to, this means a column containing 10 g or 20 g of silica of 40 micron particle size, the silica being contained in a 60 mL disposable syringe and supported by a porous disc, obtained from Varian, Harbor City, Calif., USA under the name "Mega Bond Elut SI". Where an "Isolute™ SCX column" is referred to, this means a column containing benzenesulphonic acid (non-end-capped) obtained from International Sorbent Technology Ltd., 1st House, Duffryn Industial Estate, Ystrad Mynach, Hengoed, Mid Glamorgan, UK. Where "Argonaut™ PS-tris-amine scavenger resin" is referred to, this means a tris-(2-aminoethyl)amine polystyrene resin obtained from Argonaut Technologies Inc., 887 Industrial Road, Suite G, San Carlos, Calif., USA.

(iv) in general, the course of reactions was followed by TLC and reaction times are given for illustration only;

(v) yields, when given, are for illustration only and are not necessarily those which can be obtained by diligent process development; preparations were repeated if more material was required;

(vi) when given, $^1$H NMR data is quoted and is in the form of delta values for major diagnostic protons, given in parts per million (ppm) relative to tetramethylsilane (TMS) as an internal standard, determined at 300 MHz using perdeuterio DMSO ($CD_3SOCD_3$) as the solvent unless otherwise stated; coupling constants (J) are given in Hz;

(vii) chemical symbols have their usual meanings; SI units and symbols are used;

(viii) solvent ratios are given in percentage by volume;

(ix) mass spectra (MS) were run with an electron energy of 70 electron volts in the chemical ionisation (APCI) mode using a direct exposure probe; where indicated ionisation was effected by electrospray (ES); where values for m/z are given, generally only ions which indicate the parent mass are reported, and unless otherwise stated the mass ion quoted is the positive mass ion—$(M+H)^+$;

(x) LCMS characterisation was performed using a pair of Gilson 306 pumps with Gilson 233 XL sampler and Waters ZMD4000 mass spectrometer. The LC comprised water symmetry 4.6×50 column C18 with 5 micron particle size. The eluents were: A, water with 0.05% formic acid and B, acetonitrile with 0.05% formic acid. The eluent gradient went from 95% A to 95% B in 6 minutes. Where indicated ionisation was effected by electrospray (ES); where values for m/z are given, generally only ions which indicate the parent mass are reported, and unless otherwise stated the mass ion quoted is the positive mass ion—$(M+H)^+$;

(xi) the compounds of the Examples and Methods were named using the IUPAC name program from Advanced Chemistry Development Inc, version 6.00; and, (xii) the following abbreviations are used:

| | |
|---|---|
| DMSO | dimethyl sulfoxide; |
| DMF | N-dimethylformamide; |
| DCM | dichloromethane; |
| THF | tetrahydrofuran; |
| DIPEA | N,N-diisopropylethylamine; |
| DIBAL | Di-iso-butyl aluminium hydride |
| NMP | N-methylpyrrolidinone; |
| HATU | O-(7-Azabenzotriazol-1-yl)-N,N',N',N'-tetramethyluronium hexafluorophosphate; |
| HBTU | O-(7-Benzotriazol-1-yl)-N,N,N',N'-tetramethyluronium hexafluorophosphate; |
| Boc | tert-butoxycarbonyl; |
| MeOH | methanol; |
| TFA | trifluoroacetic acid; |
| TMEDA | N,N,N',N'-tetramethylethylenediamine |
| PS | polymer supported |
| MP | macro porous |
| HPLC | high pressure liquid chromatography; |
| EtOH | ethanol; and |
| EtOAc | ethyl acetate. |

EXAMPLE 1

This Example illustrates the preparation of 1-(1-{3-[4-(ethylsulfonyl)piperazin-1-yl]-3-phenylpropyl}piperidin-4-yl)-5-(methylsulfonyl)-1H-benzimidazole (Compound 1 Table I).

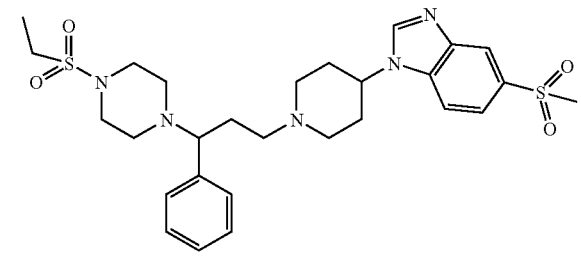

Triethylamine (72 µl) was added to a solution of 5-(methylsulfonyl)-1-[1-(3-phenyl-3-piperazin-1-ylpropyl)piperidin-4-yl]-1H-benzimidazole (100 mg) in dichloromethane (10 ml) followed by ethanesulphonyl chloride (20 µl) and the mixture was stirred at room temperature for 1 hour. The reaction mixture was washed with water (10 ml) and brine (10 ml) and dried. The residue obtained on removal of the solvent was passed through a 10 g silica Bond elut column eluting with a solvent gradient (ethyl acetate-20% methanol/ethyl acetate) to give the title compound, yield 50 mg, M+H 560.

5-(Methylsulfonyl)-1-[1-(3-phenyl-3-piperazin-1-ylpropyl)piperidin-4-yl]-1H-benzimidazole

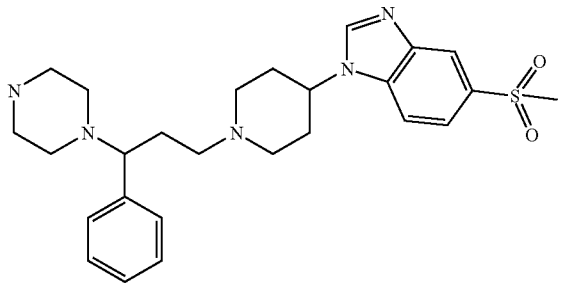

Boc-piperazine (393 mg) was added to a mixture of triethylamine (0.59 ml), 1-[1-(3-chloro-3-phenylpropyl)piperidin-4-yl]-5-(methylsulfonyl)-1H-benzimidazole (910 mg) and sodium iodide (250 mg) in dichloromethane (20 ml) and the mixture was stirred at room temperature for 8 days, washed with water (20 ml) and brine (20 ml), dried and evaporated to dryness. The residue was passed through a 20 g silica Bond-elut column eluting with a mixture of ethyl acetate/methanol (4:1) to give the N-Boc protected title compound, yield 761 mg, M+H 482.

The product was dissolved in dichloromethane (20 ml) and trifluoroacetic acid (3 ml) was added. The mixture was allowed to stand at room temperature for 2 hours and was evaporated to dryness. The residue was dissoleved in 2M NaOH (10 ml) and was extracted with dichloromethane (2×15 ml), dried and evaporated to dryness to give the title compound, yield 450 mg, M+H 482.

1-[1-(3-Chloro-3-phenylpropyl)piperidin-4-yl]-5-(methylsulfonyl)-1H-benzimidazole

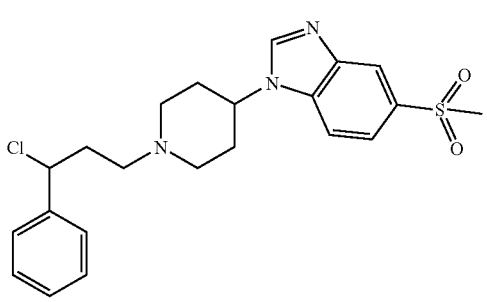

Sodium borohydride (189 mg) was added to a solution of 3-{4-[5-(methylsulfonyl)-1H-benzimidazol-1-yl]piperidin-1-yl}-1-phenylpropan-1-one (2.07 g) in ethanol (40 ml) at 0° C., the mixture was allowed to warm to room temperature and was stirred for 16 hours. The reaction mixture was evaporated to dryness, the residue was redissolved in dichloromethane and washed with water (15 ml) and brine (15 ml) and dried. Removal of the solvent gave 3-{4-[5-(methylsulfonyl)-1H-benzimidazol-1-yl]piperidin-1-yl}-1-phenylpropan-1-ol, 2.1 g, M+H 414.

Methanesulphonyl chloride (0.46 ml) was added to a solution of 3-{4-[5-(methylsulfonyl)-1H-benzimidazol-1-yl]piperidin-1-yl}-1-phenylpropan-1-ol (2.1 g) and triethylamine (0.9 ml) in dichloromethane (30 ml) at 0° C. The mixture was allowed to warm to room temperature and stirring was continued for 16 hours. The reaction mixture was washed with water (15 ml) and brine (15 ml) and dried. Removal of the solvent gave the title compound as an orange foam, yield 1.85 g, M+H 432.

3-{4-[5-(Methylsulfonyl)-1H-benzimidazol-1-yl]piperidin-1-yl}-1-phenylpropan-1-one

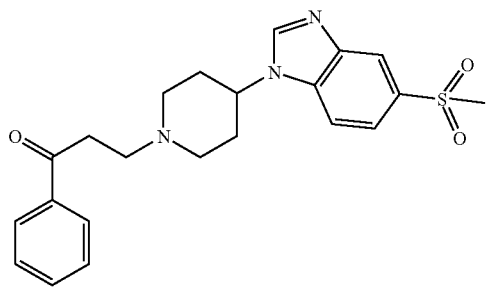

3-Chloropropiophenone (860 mg) was added to a mixture of 5-(methylsulfonyl)-1-piperidin-4-yl-1H-benzimidazole (1.395 g) and potassium carbonate (1.38 g) in DMF (30 ml) and stirred for 2 days. The reaction mixture was evaporated to dryness and the residue was dissolved in dichloromethane (20 ml), washed with water (15 ml) and brine (15 ml), dried and evaporated to dryness to give the title compound, yield 2.07 g, M+H 412, NMR (CDCl$_3$) 2.2 (m, 4H) 2.3-2.4 (m, 2H) 2.9 (m, 2H) 3.1 (s, 3H) 3.2-3.3 (m, 4H) 4.3 (m, 1H) 7.5 (m, 2H) 7.6 (m, 2H) 7.9 (m, 2H) 8.0 (m, 1H) 8.2 (s, 1H) 8.4 (s, 1H).

EXAMPLE 2

This Example illustrates the preparation of 1-{(1S)-3-[4-(3-isopropyl-5-methyl-4H-1,2,4-triazol-4-yl)piperidin-1-yl]-1-phenylpropyl}-4-(phenylsulfonyl)piperazine (Compound 1 Table II).

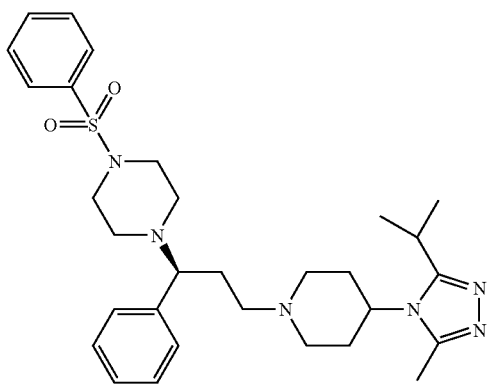

Triethylamine (195 μl) and benzenesulphonylpiperazine (190 mg) were added to a solution of 1-[(3R)-3-chloro-3-phenylpropyl]-4-(3-isopropyl-5-methyl-4H-1,2,4-triazol-4-yl)piperidine (252 mg) [Method G] in dichloromethane (7 ml) and the mixture was stirred for 9 days at room temperature. PS-NCO (700 mg) was added and stirring was continued for 16 hours. The reaction mixture was filtered and the filter cake was washed with 10% methanol in dichloromethane (2×20 ml). The combined filtrate and washings were evaporated to dryness and the residue was passed down a silica column (Biotage 40 g) eluted with a solvent gradient of 1% 7M ammonia in methanol in dichloromethane to 3% 7M ammonia in methanol in dichloromethane, yield 90 mg, (M+H) 551, NMR (CDCl$_3$): 1.34 (6H, d), 1.67-2.27 (17H, m), 2.47 (3H, s), 2.80-3.01 (4H, m), 3.32 (1H, m), 3.78 (1H, m), 7.15 (2H, d), 7.28 (3H, s), 7.51 (1H, t), 7.58 (1H, m), 7.72 (2H, d).

EXAMPLE 3

This Example illustrates the preparation of 1-(1-{(3R)-3-(3,5-difluorophenyl)-3-[1-(methylsulfonyl)piperidin-4-yl]propyl}piperidin-4-yl)-5-(methylsulfonyl)-1H-benzimidazole (Compound 5 Table II).

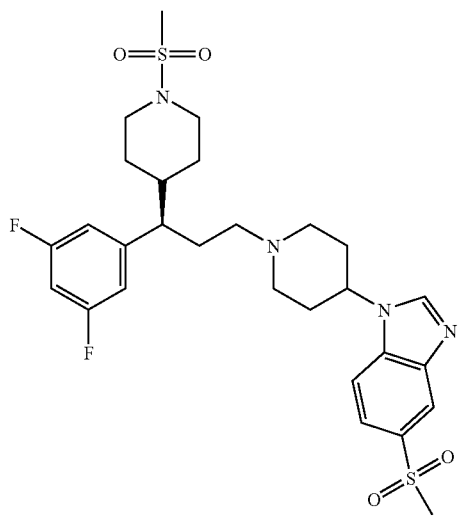

Sodium triacetoxyborohydride (2.5 g) was added to a solution of 5-(methylsulfonyl)-1-piperidin-4-yl-1H-benzimidazole (1.6 g) [Method A] and (3R)-3-(3,5-difluorophenyl)-3-[1-(methylsulfonyl)piperidin-4-yl]propanal (1.98 g) in dichloromethane (100 ml) and the mixture was stirred at room temperature for 2 hours. The reaction mixture was washed with 2M NaOH (2×100 ml), dried and evaporated to dryness. The residue was dissolved in dichloromethane (20 ml) and poured onto a 50 g SCX2 cartridge eluted with methanol (6×50 ml) and 1M ammonia in methanol (7×50 ml). The combined methanolic ammonia washings were evaporated to dryness and the residue was triturated with diethyl ether (75 ml) to give the product as a white powder, yield 2.7 g, Mpt 161° C., M+H 595, NMR (CDCl$_3$): 1.2-1.8 (m, 5H) 2-2.3 (m, 10H) 2.4-2.7 (m, 3H) 2.75 (s, 3) 2.9-3.1 (m, 2H) 3.15 (s, 3H) 3.7-3.9 (m, 2H) 4.2 (m, 1H) 6.7 (m, 3H) 7.55 (d, 2H) 7.9 (d, 1H) 8.15 (s, 1H) 8.4 (s, 1H).

EXAMPLE 4

This Example illustrates the preparation of 4-(3-isopropyl-5-methyl-4H-1,2,4-triazol-4-yl)-1-{3-[1-(methylsulfonyl)piperidin-4-yl]-3-phenylpropyl}piperidine (Compound 5 Table I).

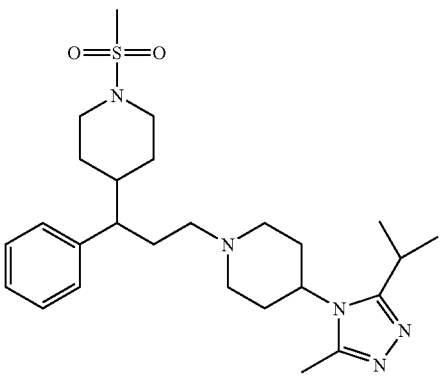

Methanesulphonyl chloride (61 μl) was added to a solution of 4-(3-isopropyl-5-methyl-4H-1,2,4-triazol-4-yl)-1-(3-phenyl-3-piperidin-4-ylpropyl)piperidine (263 mg) [Method J] and triethylamine (178 μl) in dichloromethane (3 ml) at 0° C. The mixture was allowed to warm to room temperature and stirring was continued for 2 hours. The reaction mixture was poured onto a 10 g SCX column and washed with methanol and then 1M ammonia in methanol. The methanolic ammonia washings were evaporated to dryness and the residue was purified by chromatography on a silica Bond-elut column eluting with a mixture of 3% 1M ammonia in methanol and dichloromethane, yield 204 mg, (M+H) 488, NMR (CDCl$_3$): 1.18-1.58 (4H, m), 1.36 (6H, d), 1.64-2.22 (14H, m), 2.38 (1H, m) 2.48 (1H, m), 2.48 (3H, s), 2.60 (1H, m), 2.74 (3H, s), 2.98 (3H, m), 3.70 (1H, m), 3.82 (2H, m), 7.10 (2H, d), 7.26 (3H, m).

EXAMPLE 5

This Example illustrates the preparation of 2-(1-{(3S)-3-phenyl-3-[4-(phenylsulfonyl)piperazin-1-yl]propyl}piperidin-4-yl)-1,3-thiazole-4-carboxamide (Compound 16 Table II).

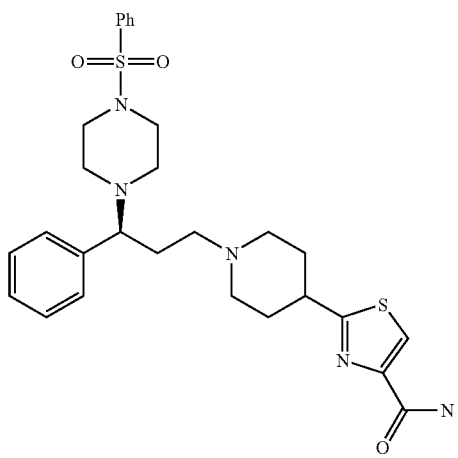

A solution of ethyl 2-(1-{(3S)-3-phenyl-3-[4-(phenylsulfonyl)piperazin-1-yl]propyl}piperidin-4-yl)-1,3-thiazole-4-carboxylate (152 mg) in 35% ammonia (5 ml) and THF (3 ml) was stirred for 24 hours and evaporated to dryness. The residue was purified on a 20 g Isolute silica column eluting with a mixture of 1-2% ammonia in methanol in dichloromethane. Yield 101 mg, M+H 554.

The ethyl 2-(1-{(3S)-3-phenyl-3-[4-(phenylsulfonyl)piperazin-1-yl]propyl}piperidin-4-yl)-1,3-thiazole-4-carboxylate used as starting material was prepared as described in Method G but using ethyl 2-piperidin-4-yl-1,3-thiazole-4-carboxylate (Method K) as the amine component.

EXAMPLE 6

This Example illustrates the preparation of N-benzyl-2-(1-{3-[1-(methylsulfonyl)piperidin-4-yl]-3-phenylpropyl}piperidin-4-yl)-1,3-thiazole-4-carboxamide (Compound 9 Table I).

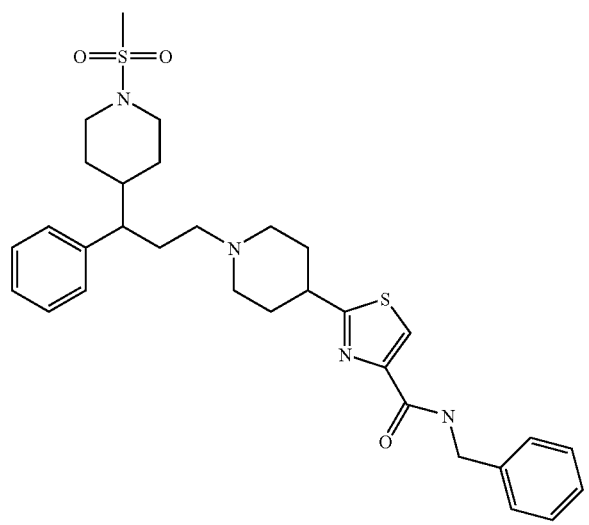

HATU (153 mg), diisopropylethylamine (139 µl) and benzylamine (44 µl) were added to a solution of 2-(1-{3-[1-(methylsulfonyl)piperidin-4-yl]-3-phenylpropyl}piperidin-4-yl)-1,3-thiazole-4-carboxylic acid (192 mg) in dichloromethane and the mixture was stirred for 48 hours. Dichloromethane (50 ml) was added and the solution was washed with saturated ammonium chloride (2×25 ml), water (25 ml), brine (25 ml) and dried. The residue obtained on removal of the solvent was purified on a 20 g Isolute column eluting with a solvent gradient of 10% methanol in ethyl acetate to 20% methanol in ethyl acetate. Yield 182 mg.

Preparation of 2-(1-{3-[1-(methylsulfonyl)piperidin-4-yl]-3-phenylpropyl}piperidin-4-yl)-1,3-thiazole-4-carboxylic acid

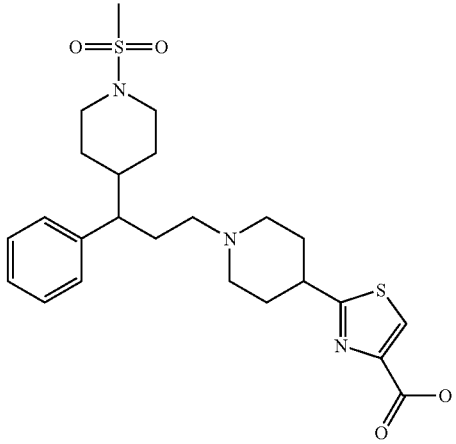

Lithium hydroxide (118 mg) was added to a solution of ethyl 2-(1-{3-[1-(methylsulfonyl)piperidin-4-yl]-3-phenylpropyl}piperidin-4-yl)-1,3-thiazole-4-carboxylate (290 mg) in a mixture of water (1 ml) and THF (3 ml) and the mixture was stirred for 24 hours. Additional water (1 ml) was added and the mixture was acidified to pH 4 with 2M HCl and extracted with dichloromethane (2×50 ml). The combined extracts were dried and solvent removed to give the acid, yield 196 mg.

The ethyl 2-(1-{3-[1-(methylsulfonyl)piperidin-4-yl]-3-phenylpropyl}piperidin-4-yl)-1,3-thiazole-4-carboxylate used as starting material was prepared by reductive amination of 3-[1-(methylsulfonyl)piperidin-4-yl]-3-phenylpropanal (prepared following Method I using 4-benzoyl-N-methanesulphonylpiperidine as starting material) with ethyl 2-piperidin-4-yl-1,3-thiazole-4-carboxylate (Method K) as the amine component.

EXAMPLE 7

This Example illustrates the preparation of 1-{1-[(3R)-3-(3,5-difluorophenyl)-3-(tetrahydro-2H-pyran-4-yl)propyl]piperidine-4-yl}-5-(methylsulfonyl)-1H-benzimidazole (Compound 2 Table III).

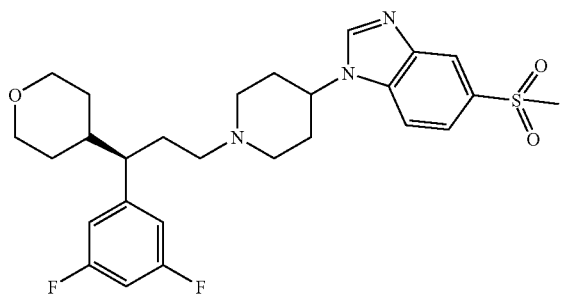

To a solution of 5-(methylsulfonyl)-piperidin-4-yl-1H-benzimidazole (140 mg) [Method A] and (3R)-3-(3,5-difluorophenyl)-3-(tetrahydro-2H-pyran-4-yl propanal (127 mg) in dichloromethane (10 ml) was added polymer supported PStriacetoxyborohydride (604 mg, 2.07 mmol/g) and the mixture was stirred for 18 hours. The reaction mixture was filtered and evaporated to dryness. The residue was purified on 20 g of silica Bond elute column with a solvent gradient of ethyl acetate-30% methanol/ethyl acetate to give the title compound. Yield 150 mg, M+H 518, NMR (CDCl₃): 1.3 (m, 2H) 1.4 (m, 1H) 1.8 (m, 3H) 1.9 (m, 1H) 2.2-2.3 (m, 8H) 2.5 (m, 1H) 3.0-3.2 (m, 5H) 3.4 (m, 1H) 3.5 (m, 1H) 4.0 (m, 1H) 4.1 (m, 1H) 4.3 (m, 1H) 6.8 (m, 3H) 7.6 (d, 1H) 8.0 (d, 1H) 8.2 (s, 1H) 8.5 (s, 1H).

EXAMPLE 8

This Example describes the preparation of 1-{(3R)-3-(3,5-difluorophenyl)-3-[1-(methylsulphonyl)piperidin-4-yl]propyl}-4-[3-methyl-5-(trifluoromethyl)-4H-1,2,4-triazol-4-yl]piperidine (Compound 25 Table II).

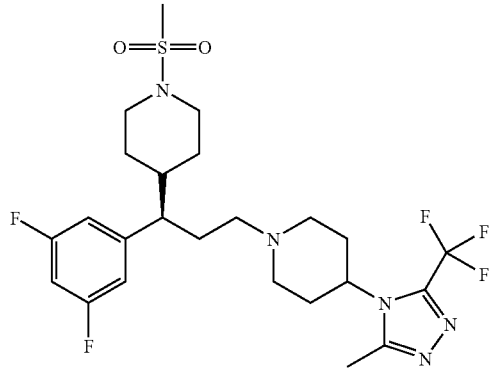

A solution of (3R)-3-(3,5-difluorophenyl)-3-[1-(methylsulphonyl)piperidin-4-yl]propanal (165 mg) in dichloromethane (4 ml) was added to a solution of 4-[3-methyl-5-(trifluoromethyl)-4H-1,2,4-triazol-4-yl]piperidine (117 mg) (Method P) in dichloromethane (4 ml) followed by MP-triacetoxyborohydride (800 mg) and the mixture was stirred for 5 hours. PS-isocyanate (200 mg) was added and stirring was continued for 3 hours. The resin was filtered and washed with 10% methanol in dichloromethane (10 ml) and the filtrate was evaporated to dryness. The residue was purified by chromatography on silica (Isolute 20 g) eluting with a solvent gradient of 5% methanol/ethyl acetate to 10% methanol/ethyl acetate to give the title compound as a white foam, yield 146 mg. LC-MS M+H 550, NMR (CDCl₃) 1.20-1.72 (7H, m), 1.94-2.28 (7H, m), 2.44 (1H, t), 2.52 (1H, t), 2.64(1H), 2.66 (3H, s), 2.76 (3H, s), 2.92 (1H, d), 3.04 (1H, d), 3.72 (1H, d), 3.84 (1H, d), 4.10 (2H, m), 6.68 (3H. m).

In an analogous manner using 3-[3-methyl-5-(trifluoromethyl)-4H-1,2,4-triazol-4-yl]-8-azabicyclo[3.2.1]octane as starting material there is obtained 8-{(3R)-3-(3,5-difluorophenyl)-3-[1-(methylsulphonyl)piperidin-4-yl]propyl}-3-[3-methyl-5-(trifluoromethyl)-4H-1,2,4-triazol-4-yl]-8-azabicyclo[3.2.1]octane (Compound 5 Table VI).

EXAMPLE 9

This Example describes the preparation of 1-(1-{(3R)-3-(3,5-difluorophenyl)-3-[1-(methylsulphonyl)piperidin-4-yl]propyl}piperidin-4-yl)-1,3-dihydro-2H-imidazol-2-one (Compound 5 Table V).

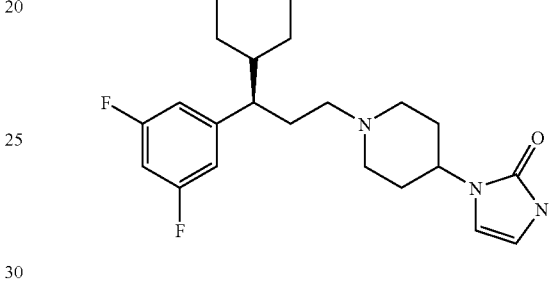

Sodium triacetoxyborohydride (1.26 g) was added to a solution of 1-piperidin-4-yl-1,3-dihydro-2H-imidazol-2-one (1 g) (Method Q) and (3R)-3-(3,5-difluorophenyl)-3-[1-(methylsulphonyl)piperidin-4-yl]propanal (1.95 g) in dichloromethane (100 ml) and the mixture was stirred for 15 hours, washed with 2M NaOH (3×50 ml) and dried. The residue obtained on removal of the solvent was purified on a silica column eluting with a solvent gradient of ethyl acetate-40% methanol/ethyl acetate to give the title compound, yield 1.1 g, M+H 483, NMR CDCl₃: 1.2-2.2 (m, 15H) 2.4-2.7 (m, 3H) 2.75 (s, 3H) 2.9-3 (m, 2H) 3.7-3.9 (m, 2H) 3.95-4.05 (m, 1H) 6.3 (m, 2H) 6.7(m, 3H) 9.8 (s, 1H).

In an analogous manner using 1-piperidin-4-ylimidazolidin-2-one as starting material there is obtained 1-(1-{(3R)-3-(3,5-difluorophenyl)-3-[1-(methylsulfonyl)piperidin-4-yl]propyl}piperidin-4-yl)imidazolidin-2-one (Compound 1 Table V), M+H 485, NMR CDCl₃ 1.05-1.8 (m, 8H) 1.9-2.2 (m, 7H) 2.35-2.7 (m, 3H) 2.75 (s, 3H) 2.8-3 (m, 2H) 3.4 (s, 4H) 3.6-3.75 (m, 2H) 3.8-3.9 (m, 1H) 4.4 (s, 1H) 6.7 (m, 3H).

In an analogous manner using 4-methyl-1-piperidin-4-yl-1,3-dihydro-2H-imidazol-2-one as starting material there is obtained 1-(1-{(3R)-3-(3,5-difluorophenyl)-3-[1-(methylsulfonyl)piperidin-4-yl]propyl}piperidin-4-yl)-4-methyl-1,3-dihydro-2H-imidazol-2-one (Compound 9 Table V), M+H 497, NMR CDCl₃ 1.2-2.2 (m, 18H) 2.4-2.7 (m, 4H) 2.75 (s, 3H) 2.8-3 (m, 2H) 3.7-4 (m, 2H) 5.9 (s, 1H) 6.7 (m, 3H) 8.8 (s, 1H).

EXAMPLE 10

This Example describes the preparation of 1-(1-{(3R)-3-(3,5-difluorophenyl)-3-[1-(methylsulphonyl)piperidin-4-yl]propyl}piperidin-4-yl)-3-[4-(methylsulphonyl)benzyl]-1,3-dihydro-2H-imidazol-2-one (Compound 6 Table V).

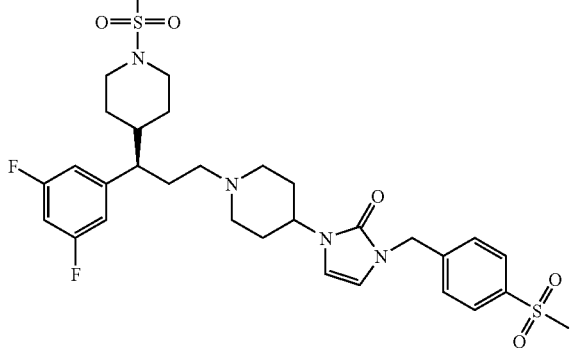

Sodium hydride (24 mg, 60% dispersion in mineral oil) was added to a solution of 1-(1-{(3R)-3-(3,5-difluorophenyl)-3-[1-(methylsulphonyl)piperidin-4-yl]propyl}piperidin-4-yl)-1,3-dihydro-2H-imidazol-2-one (0.25 g) (Example 9) in DMF (10 ml) at 0° C. and the mixture was stirred for 30 minutes. 4-Methanesulphonylbenzyl chloride (105 mg) was added; the reaction mixture was allowed to warm to room temperature and stirring was continued for 2 hours. The solvent was evaporated and the residue was dissolved in dichloromethane (30 ml), washed with water (2×30 ml), dried and evaporated to dryness. The residue was purified by chromatography on silica eluting with a solvent gradient of ethyl acetate to 30% methanol/ethyl acetate, yield 55 mg, M+H 651, NMR CDCl$_3$ 1.1-2.2 (m, 16H) 2.4-2.7 (m, 3H) 2.75 (s, 3H) 2.8-3 (m, 2H) 3.05 (s, 3H) 3.7-4 (m, 2H) 4.9 (s, 2H) 6.15 (d, 1H) 6.25 (d, 1H) 6.7 (m, 3H) 7.4 (d, 2H) 7.9 (d, 2H).

EXAMPLE 11

This Example describes the preparation of 1-(1-{(3R)-3-(3,5-difluorophenyl)-3-[1-(methylsulfonyl)piperidin-4-yl]propyl}piperidin-4-yl)-3-[4-(methylsulfonyl)phenyl]-1,3-dihydro-2H-imidazol-2-one (Compound 7 Table V).

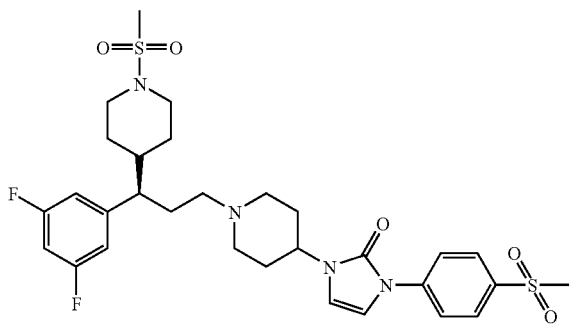

Argon was bubbled through a suspension of 1-(1-{(3R)-3-(3,5-difluorophenyl)-3-[1-(methylsulphonyl)piperidin-4-yl]propyl}piperidin-4-yl)-1,3-dihydro-2H-imidazol-2-one (400 mg, Example 9), 4-methanesulphonylbromobenzene (193 mg), potassium phosphate (350 mg) and copper iodide (314 mg) in dioxane (25 ml) for 10 minutes and N,N'-dimethylethylenediamine (290 mg) was added. Argon was passed through the stirred mixture for 10 minutes and the mixture was then heated at 100° C. for 6 hours under an atmosphere of argon. The solvent was evaporated and the residue was dissolved in ethyl acetate (100 ml) and washed with 20% ammonium chloride solution (2×50 ml). The ethyl acetate solution was dried and evaporated to dryness to give the title compound, yield 171 mg, M+H 637, NMR DMSO D6 1.1-2.2 (m, 16H) 2.6-2.75 (m, 3H) 2.8 (s, 3H) 2.9 (m, 1H) 3.2 (s, 3H) 3.4-3.6 (m, 2H) 6.9-7.1 (m, 4H) 7.2 (m, 1H) 7.9-8.1 (q, 4H).

In an analogous manner using 1-(1-{(3R)-3-(3,5-difluorophenyl)-3-[1-(methylsulfonyl)piperidin-4-yl]propyl}piperidin-4-yl)imidazolidin-2-one (Example 9 part 2) as starting material there is obtained 1-(1-{(3R)-3-(3,5-difluorophenyl)-3-[1-(methylsulfonyl)piperidin-4-yl]propyl}piperidin-4-yl)-3-[4-(methylsulfonyl)phenyl]imidazolidin-2-one (Compound 3 Table V), M+H 639, NMR DMSO D6 1.1-2.2 (m, 16H) 2.6-2.75 (m, 2H) 2.8 (s, 3H) 2.9 (m, 1H) 3.1 (s, 3H) 3.4-6 (m, 3H) 3.8-3.9 (m, 1H) 6.9-7.1 (m, 3 H) 7.8 (q, 4H).

In an analogous manner using 1-(1-{(3R)-3-(3,5-difluorophenyl)-3-[1-(methylsulfonyl)piperidin-4-yl]propyl}piperidin-4-yl)-4-methyl-1,3-dihydro-2H-imidazol-2-one as starting material there is obtained 1-(1-{(3R)-3-(3,5-difluorophenyl)-3-[1-(methylsulfonyl)piperidin-4-yl]propyl}piperidin-4-yl)-4-methyl-3-[4-(methylsulfonyl)phenyl]-1,3-dihydro-2H-imidazol-2-one (Compound 11 Table V), NMR CDCl$_3$ 1.2-2.2 (m, 19H) 2.4-2.7 (m, 3H) 2.75 (s, 3H) 2.8-3 (m, 2H) 3.1 (s, 3H) 3.7-4 (m, 2H) 6.1 (s, 1H) 6.7 (m, 3H) 7.6-8.05 (q, 4H).

EXAMPLE 12

This Example describes the preparation of 1-(1-{(3R)-3-(3,5-difluorophenyl)-3-[1-(methylsulfonyl)piperidin-4-yl]propyl}piperidin-4-yl)-3-{[1-(methylsulfonyl)piperidin-4-yl]methyl}-1,3-dihydro-2H-imidazol-2-one (Compound 8 Table V).

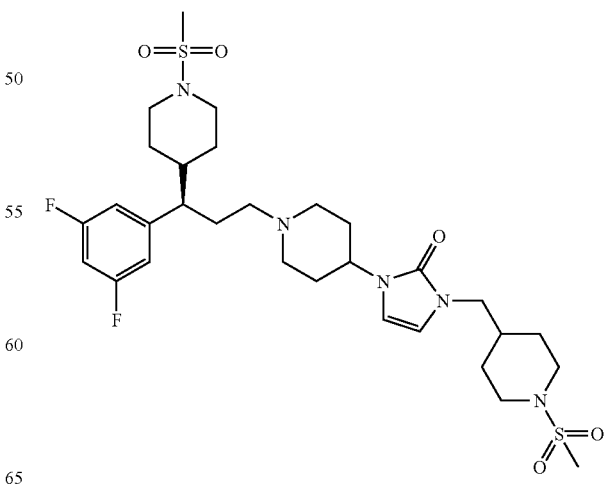

Step 1: Preparation of 1-(1-{(3R)-3-(3,5-difluorophenyl)-3-[1-(methylsulfonyl)piperidin-4-yl]propyl}piperidin-4-yl)-3-(piperidin-4-ylmethyl)-1,3-dihydro-2H-imidazol-2-one

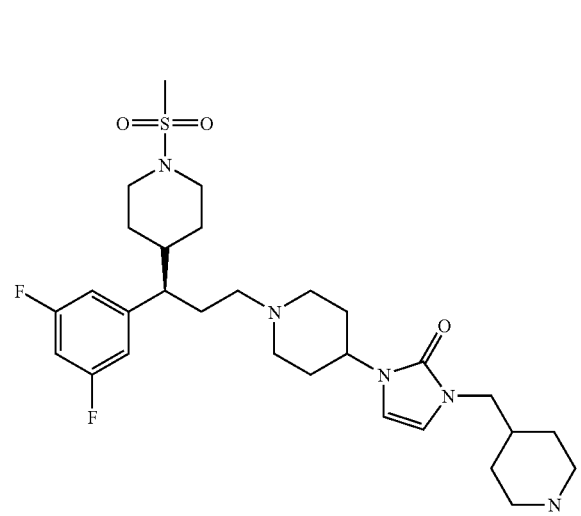

tert-Butyl 4-{[3-(1-{(3R)-3-(3,5-difluorophenyl)-3-[1-(methylsulfonyl)piperidin-4-yl]propyl}piperidin-4-yl)-2-oxo-2,3-dihydro-1H-imidazol-1-yl]methyl}piperidine-1-carboxylate (300 mg) (example 10 part 2) was dissolved in TFA (10 ml) and allowed to stand at room temperature for 2 hours. The TFA was evaporated and the residue was used directly in step 2.

Step 2. Preparation of the Title Compound

Methanesulphonyl chloride (49 mg) was added to a solution of 1-(1-{(3R)-3-(3,5-difluorophenyl)-3-[1-(methylsulfonyl)piperidin-4-yl]propyl}piperidin-4-yl)-3-(piperidin-4-ylmethyl)-1,3-dihydro-2H-imidazol-2-one trifluoroacetate salt (300 mg) and triethylamine (132 mg) in dichloromethane (10 ml) and the mixture was stirred for 1 hour. The reaction mixture was washed with water (2×50 ml), dried and evaporated to dryness. The residue was purified by chromatography on silica eluting with a solvent gradient of ethyl acetate-40% methanol/ethyl acetate. Yield 28 mg, M+H 658.

In an analogous manner following Steps 1 and 2 and using tert-butyl 4-{[3-(1-{(3R)-3-(3,5-difluorophenyl)-3-[1-(methylsulphonyl)piperidin-4-yl]propyl}piperidin-4-yl)-2-oxoimidazolidin-1-yl]methyl}piperidine-1-carboxylate as starting material there is obtained 1-(1-{(3R)-3-(3,5-difluorophenyl)-3-[1-(methylsulphonyl)piperidin-4-yl]propyl}piperidin-4-yl)-3-{[1-(methylsulphonyl)piperidin-4-yl]methyl}imidazolidin-2-one (Compound 4 Table V), M+H 660.

EXAMPLE 13

This Example describes the preparation of tert-butyl 1'-{(3R)-3-(3,5-difluorophenyl)-3-[1-(methylsulphonyl)piperidin-4-yl]propyl}-4,4'-bipiperidine-1-carboxylate (Compound 1 Table VIII).

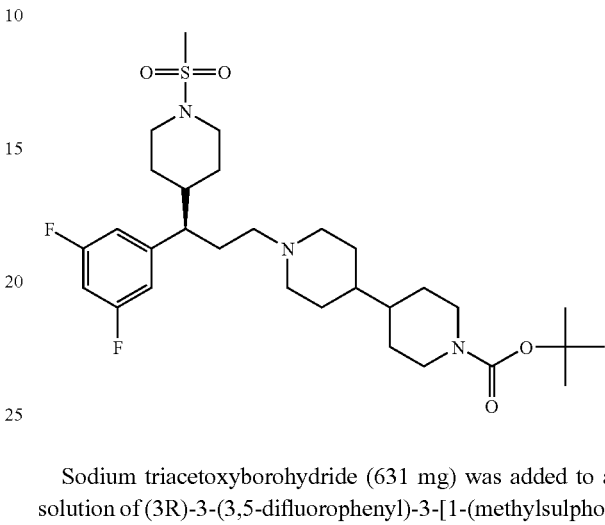

Sodium triacetoxyborohydride (631 mg) was added to a solution of (3R)-3-(3,5-difluorophenyl)-3-[1-(methylsulphonyl)piperidin-4-yl]propanal (990 mg) and tert-butyl 4,4'-bipiperidine-1-carboxylate (800 mg) in dichloromethane (50 ml). The mixture was stirred for 2 hours, washed with 2M NaOH (2×50 ml) and dried. The residue obtained on evaporation of the solvent was purified by chromatography on silica eluting with a solvent gradient of ethyl acetate 40% methanol/ethyl acetate, yield 360 mg, M+H 583, NMR CDCl$_3$ 1-1.4 (m, 9H) 1.45 (s, 9H) 1.5-2.2 (m, 14H) 2.35-2.65 (m, 3H) 2.7 (s, 3H) 2.8-3 (m, 2H) 3.7-3.8 (m, 2H) 4.1 m, 2H) 6.6 (m, 3H).

EXAMPLE 14

This Example describes the preparation of 1-{(3R)-3-(3,5-difluorophenyl)-3-[1-(methylsulfonyl)piperidin-4-yl]propyl}-1'-(methylsulfonyl)-4,4'-bipiperidine (Compound 3 Table VIII).

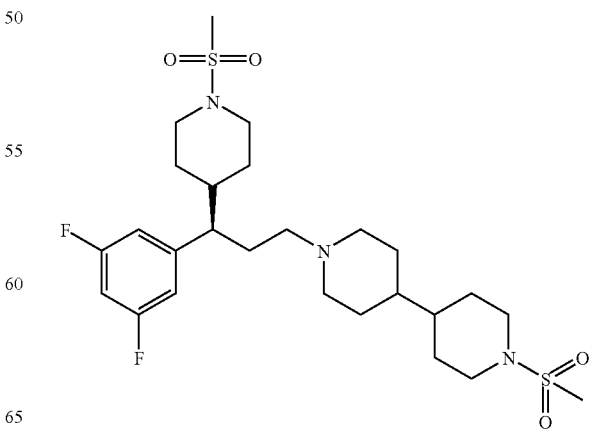

Methanesulphonyl chloride (49 mg) was added to a stirred solution of 1-{(3R)-3-(3,5-difluorophenyl)-3-[1-(methylsulphonyl)piperidin-4-yl]propyl}-4,4'-bipiperidine trifluoroacetate (260 mg) [prepared from the title compound of Example 13 following the method described in Example 12, step 1] and triethylamine (88 mg) in dichloromethane (20 ml) and stirring was continued for 30 minutes. The reaction mixture was washed with 2M NaOH (2×20 ml), dried and evaporated to dryness. The residue was purified by chromatography on silica eluting with a solvent gradient of ethyl acetate-30% methanol/ethyl acetate, yield 100 mg, M+H 562, NMR CDCl$_3$ 1-2.2 (m, 22H) 2.3-2.7 (m, 5H) 2.75 (s, 6H) 2.8-2.9 (m, 1H) 3.6-3.9 (m, 4H) 6.7 (m, 3H).

In an analogous manner using trifluoroacetyl chloride as reactant there was obtained 1-{(3R)-3-(3,5-difluorophenyl)-3-[1-(methylsulphonyl)piperidin-4-yl]propyl}-1'-(trifluoroacetyl)-4,4'-bipiperidine (Compound 2 Table VII), M+H 580, NMR CDCl$_3$ 1-2.2 (m, 21H) 2.3-2.7 (m, 4H) 2.75 (s, 3H) 2.8-3.05 (m, 3H) 3.7-4.1 (m, 3H) 4.6 (m, 1H) 6.6 (m, 3H).

EXAMPLE 15

This Example illustrates the preparation of 8-{(3R)-3-(3,5-difluorophenyl)-3-[1-(methylsulfonyl)piperidin-4-yl]propyl}-3-exo-(3-isopropyl-5-methyl-4H-1,2,4-triazol-4-yl)-8-azabicyclo[3.2.1]octane (Compound 3 Table IV).

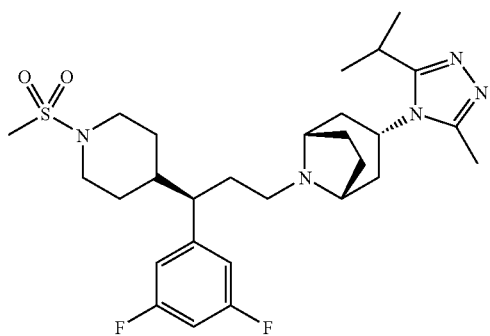

To a solution of (3R)-3-(3,5-difluorophenyl)-3-[1-(methylsulphonyl)piperidin-4-yl]propanal (169 mg) (Method H) and 3-(3-isopropyl-5-methyl-4H-1,2,4-triazol-4-yl)-exo-8-azabicyclo[3.2.1]octane (120 mg) (Method N) in dichloromethane (6 ml) was added MP-triacetoxyborohydride resin (620 mg, 2.07 mmol/g). The resulting mixture was stirred at room temperature for 18 hours. The mixture was filtered and washed with more dichloromethane. The organics were evaporated to give an oil which was purified by chromatography on silica eluting with methanol/dichloromethane (5:95) to give the titled compound as a solid (280 mg). NMR CDCl$_3$ 1.2-1.5 (m, 2H), 1.4 (d, 6H), 1.5-1.7 (m, 8H), 1.9-2.05 (m, 4H), 2.1-2.25 (m, 4H), 2.45 (s, 3H), 2.5-2.7 (m, 2H), 2.75 (s, 3H), 3.0 (m, 1H), 3.3 (m, 2H), 3.75 (m, 1H), 3.85 (m, 1H), 4.25 (m, 1H), 6.7 (m, 3H). MS 550 (M+H).

EXAMPLE 16

This Example illustrates the preparation of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine. (Compound 1 Table VII).

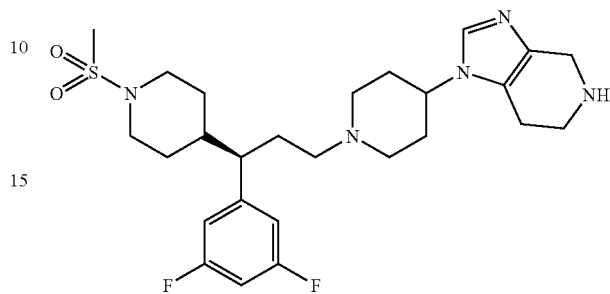

To a solution of 1-(1-{(3R)-3-(3,5-difluorophenyl)-3-[1-(methylsulfonyl)piperidin-4-yl]propyl}piperidin-4-yl)-1H-imidazo[4,5-c]pyridine (Compound 23, Table II; 0.60 g) in trifluoroacetic acid (50 ml) was added PtO$_2$ (75 mg) and the reaction mixture was heated to 70° C. with stirring under an atmosphere of hydrogen gas (65 psi) for 48 hours. The reaction mixture was filtered and solvents evaporated under reduced pressure to give a brown gum, which was suspended in dichloromethane (75 ml). To this was added conc. HCl (4 ml) then the resulting brown solid precipitate was filtered under suction, dissolved in methanol and purified by SCX ion-exchange chromatography, eluting with a gradient of methanolic ammonia in methanol, followed by further purification by silica chromatography, eluting with a gradient of methanolic ammonia in dichloromethane to give the title compound (0.37 g) as a pale yellow foam. MS (ES) 522 (M+H)$^+$, NMR(CDCl$_3$): 1.17-1.29 (m, 1H), 1.30-1.58 (m, 3H), 1.60-1.71 (m, 1H), 1.85-2.20 (m, 13H), 2.40-2.46 (t, 1H), 2.48-2.66 (m, 4H), 2.75 (s, 3H), 2.85-2.91 (d, 1H), 2.93-2.99 (d, 1H), 3.14 (t, 1H), 3.64-3.76 (m, 2H), 3.82-3.89 (m, 2H), 6.62-6.72 (m, 3H), 7.40 (s, 1H).

EXAMPLE 17

This Example illustrates the preparation of methyl 1-(1-{(3R)-3-(3,5-difluorophenyl)-3-[1-(methylsulfonyl)piperidin-4-yl]propyl}piperidin-4-yl)-1,4,6,7-tetrahydro-5H-imidazo[4,5-c]pyridine-5-carboxylate (Compound 5 Table VII).

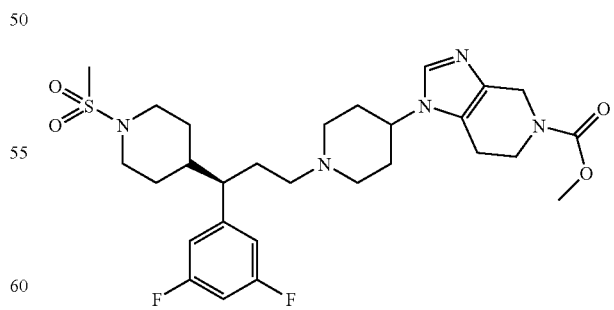

To a solution of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (0.150 g) in dichloromethane (10 ml) was added methyl chloroformate (0.036 g, 0.03 ml) followed by triethylamine (0.044 g, 0.061 ml). The resulting solution was left to stir at room temperature for 48 hours before being poured directly onto a silica cartridge and purified by column chromatography using a gradient of methanol in dichloromethane giving the title compound (0.112 g) as a white foam.

MS (ES) 580 (M+H)⁺

NMR (CDCl₃): 1.20-1.28 (m, 1H), 1.30-1.55 (m, 3H), 1.63-1.69 (m, 1H), 1.88-2.20 (m, 10H), 2.43 (t, 1H), 2.52 (td, 1H), 2.58-2.66 (m, 3H), 2.74 (s, 3H), 2.87 (d, 1H), 2.96 (d, 1H), 3.63-3.81 (m, 7H), 3.86 (d, 1H), 4.50 (s, 2H), 6.62-6.72 (m, 3H), 7.43 (s, 1H).

In a similar manner but using isopropyl chloroformate instead of methyl chloroformate was prepared isopropyl 1-(1-{(3R)-3-(3,5-difluorophenyl)-3-[1-(methylsulfonyl)piperidin-4-yl]propyl}piperidin-4-yl)-1,4,6,7-tetrahydro-5H-imidazo[4,5-c]pyridine-5-carboxylate (Compound 8 Table VII).

MS (ES) 608 (M+H)

NMR (CDCl₃): 1.3 (d, 6H), 1.4-1.8 (m, 4H), 2.0-2.3 (m, 12H), 2.4-2.75 (m, 5H), 2.8 (s, 3H), 2.9 (d, 1H), 3.0 (m, 1H), 3.7-3.8 (m, 4H), 3.9 (d, 2H), 4.6(s, 2H), 5.0 (m, 1H), 6.7-6.8 (m, 3H), 7.5 (s, 1H).

EXAMPLE 18

This Example illustrates the preparation of 5-acetyl-1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (Compound 4 Table VII).

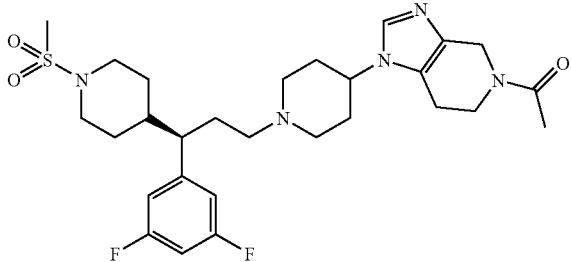

To a solution of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (0.150 g) in dichloromethane (10 ml) was added acetyl chloride (0.025 g, 0.023 ml) followed by triethylamine (0.033 g, 0.045 ml). The resulting solution was left to stir at room temperature for 48 hours before being poured directly onto a silica cartridge and purified by column chromatography using a gradient of methanol in dichloromethane giving the title compound (0.095 g) as a white foam.

MS (ES) 564 (M+H)⁺

NMR (CDCl₃): 1.17-1.27 (m, 1H), 1.30-1.71 (m, 4H), 1.88-2.10 (m, 11H), 2.16 (s, 3H), 2.42 (t, 1H), 2.52 (td, 1H), 2.58-2.70 (m, 3H), 2.74 (s, 3H), 2.88 (d, 1H), 2.97 (d, 1H), 3.65-3.76 (m, 2H), 3.82-3.93 (m, 2H), 4.48 (s, 2H), 6.62-6.72 (m, 3H), 7.44 (s, 1H).

EXAMPLE 19

This Example illustrates the preparation of 1-(1-{(3R)-3-(3,5-difluorophenyl)-3-[1-(methylsulfonyl)piperidin-4-yl]propyl}piperidin-4-yl)-5-isopropyl-4,5,6,7-tetrahydro-1H-imidazo[4,5-c]pyridine trifluoroacetate (Compound 6 Table VII).

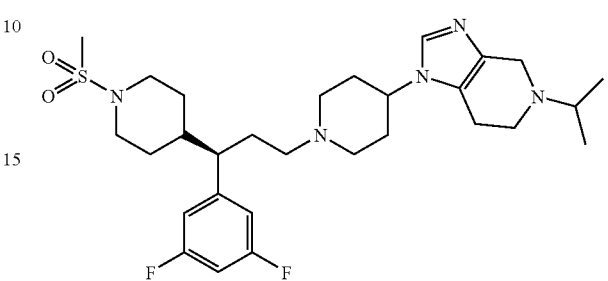

To a solution of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (0.150 g) in dichloromethane (10 ml) was added acetone (0.170 g, 0.02 ml) followed by macroporous polymer-supported triacetoxyborohydride resin (0.232 g @ 2.5 mmol/g loading). The resulting solution was left to stir at room temperature for 48 hours before being poured directly onto a silica cartridge and initially purified by column chromatography using a gradient of methanol in dichloromethane followed by further purification by reverse-phase HPLC using a gradient of (0.1% trifluoroacetic acid in acetonitrile) in (0.1% trifluoroacetic acid in water) giving the title compound (0.105 g) as a white foam.

MS (ES) 564 (M+H)⁺

NMR (DMSO_{d6}): 1.03-1.38 (m, 4H), 1.31 (d, 6H), 1.55-1.66 (m, 1H), 1.86-2.25 (m, 11H), 2.52-2.68 (m, 1H), 2.81 (s, 3H), 2.88-3.12 (m, 5H), 3.27-3.76 (m, 5H), 4.22 (s, 2H), 6.94-7.03 (m, 2H), 7.06-7.16 (t, 1H), 7.94 (s, 1H), 9.77 (s br, 1H).

EXAMPLE 20

This Example illustrates the preparation of 1-(1-{(3R)-3-(3,5-difluorophenyl)-3-[1-(methylsulfonyl)piperidin-4-yl]propyl}piperidin-4-yl)-5-[4-(methylsulfonyl)benzyl]-4,5,6,7-tetrahydro-1H-imidazo[4,5-c]pyridine trifluoroacetate (Compound 7 Table VII).

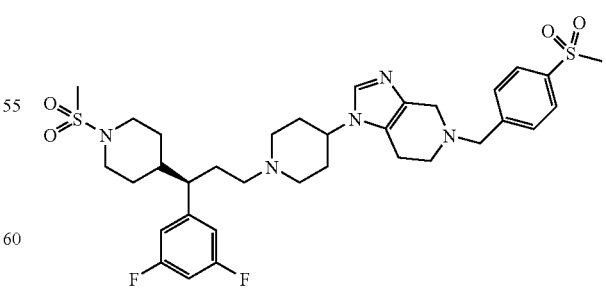

To a solution of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (0.150 g) in dichloromethane (10 ml) was added 4-(methylsulfonyl)benzyl chloride (0.060 g) followed by triethylamine (0.029 g, 0.040 ml). The resulting solution was left to stir at room temperature for 48 hours before being poured directly onto a silica cartridge and initially purified by column chromatography using a gradient of methanol in dichloromethane followed by further purification by reverse-phase HPLC using a gradient of (0.1% trifluoroacetic acid in acetonitrile) in (0.1% trifluoroacetic acid in water) giving the title compound (0.065 g) as a white foam.

MS (ES) 690 (M+H)$^+$

NMR (DMSO$_{d6}$): 1.01-1.26 (m, 3H), 1.36 (d, 1H), 1.57-1.68 (m, 1H), 1.95 (d, 1H), 2.00-2.30 (m, 9H), 2.53-2.69 (m, 3H), 2.83 (s, 3H), 2.87 (s br, 1H), 2.94-3.16 (m br, 3H), 3.24 (s, 3H), 3.49 (d, 1H), 3.56-3.70 (m, 2H), 3.86 (s br, 2H), 4.22 (s br, 2H), 4.32-4.43 (m, 1H), 7.02 (d, 2H), 7.11 (t, 1H), 7.72 (d, 2H), 7.99 (d, 2H), 8.57 (s br, 1H), 9.97 (s br, 1H).

EXAMPLE 21

This Example illustrates the preparation of 1-(1-{(3R)-3-(3,5-difluorophenyl)-3-[1-(methylsulfonyl)piperidin-4-yl]propyl}piperidin-4-yl)-5-(3,3,3-trifluoropropanoyl)-4,5,6,7-tetrahydro-1H-imidazo[4,5-c]pyridine (Compound 3 Table VII).

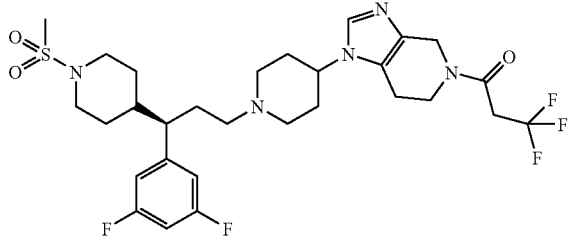

To a solution of 1,1'-carbonyldiimidazole (0.039 g) in dichloromethane (5 ml) was added 3,3,3-trifluoropropionic acid (0.031 g, 0.021 ml) and the resulting solution was left to stir for 30 minutes. To this was then added a solution of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (0.125 g) in dichloromethane (10 ml). The resulting solution was left to stir at room temperature for 18 hours before being poured into water and the layers separated. The aqueous portion was further extracted with dichloromethane then the combined organic portions were dried (MgSO$_4$) and solvents evaporated under reduced pressure before purification of the residues by column chromatography using a gradient of methanol in dichloromethane giving the title compound (0.077 g) as a white foam.

MS (ES) 632 (M+H)$^+$

NMR (CDCl$_3$): 1.18-1.70 (m, 8H), 1.87-2.20 (m, 8H), 2.43 (t, 1H), 2.52 (td, 1H), 2.59-2.69 (m, 3H), 2.74 (s, 3H), 2.88 (d, 1H), 2.97 (d, 1H), 3.24-3.36 (m, 2H), 3.64-3.76 (m, 2H), 3.86 (d, 1H), 3.96 (t, 1H), 4.48 (s, >1H major rotomer), 4.67 (s, <1H minor rotomer), 6.63-6.72 (m, 3H), 7.45 (s, 1H).

EXAMPLE 22

This Example illustrates the preparation of 1-(1-{(3R)-3-(3,5-difluorophenyl)-3-[1-(methylsulfonyl)piperidin-4-yl]propyl}piperidin-4-yl)-5-(methylsulfonyl)-4,5,6,7-tetrahydro-1H-imidazo[4,5-c]pyridine (Compound 2 Table VII).

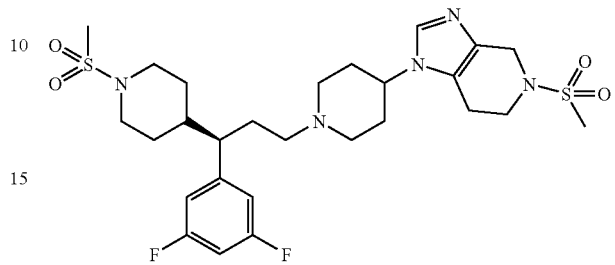

To a solution of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (0.120 g) in dichloromethane (10 ml) was added methanesulfonyl chloride (0.026 g, 0.018 ml) followed by triethylamine (0.026 g, 0.036 ml). The resulting solution was left to stir at room temperature for 18 hours before being quenched with saturated brine and the layers separated. The aqueous portion was further extracted with dichloromethane, the combined organic portions were washed with brine then the combined organic portions were dried (MgSO$_4$) and solvents evaporated under reduced pressure before purification of the residues on an SCX ion-exchange cartridge, using as eluent dichloromethane then methanol then methanolic ammonia, giving the title compound (0.102 g) as a white foam.

MS (ES) 600 (M+H)$^+$

NMR (CDCl$_3$): 1.18-1.28 (qd, 1H), 1.30-1.41 (qd, 1H), 1.42-1.58 (m, 2H), 1.61-1.72 (m, 1H), 1.87-2.20 (m, 12H), 2.43 (t, 1H), 2.52 (td, 1H), 2.62 (td, 1H), 2.73 (s, 3H), 2.84 (s, 3H), 2.89 (s, 1H), 2.94-3.02 (m, 1H), 3.63 (t, 2H), 3.66-3.75 (m, 2H), 3.85 (d, 1H), 4.35 (s, 2H), 6.61-6.73 (m, 3H), 7.47 (s, 1H).

EXAMPLE 23

This Example illustrates the preparation of 1-(1-{(3R)-3-(3,5-difluorophenyl)-3-[1-(methylsulfonyl)piperidin-4-yl]propyl}piperidin-4-yl)-N-methyl-1,4,6,7-tetrahydro-5H-imidazo[4,5-c]pyridine-5-carboxamide (Compound 9 Table VII).

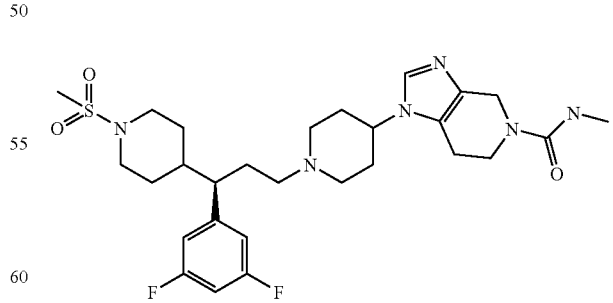

To a solution of 1-(1-{(3R)-3-(3,5-difluorophenyl)-3-[1-(methylsulfonyl)piperidin-4-yl]propyl}piperidin-4-yl)-4,5,6,7-tetrahydro-1H-imidazo[4,5-c]pyridine (0.156 g) in dichloromethane (10 ml) at 0° C. was added methyl isocyanate (0.1 ml). The resulting solution was left to stir at room temperature for 24 hours before being poured directly onto a silica cartridge and purified by column chromatography using a gradient of methanol in ethyl acetate giving the title compound (0.102 g) as a white foam.

MS (ES) 579 (M+H)$^+$

NMR (CDCl$_3$): 1.4-1.8 (m, 4H), 1.95-2.2 (m, 12H), 2.4-2.75 (m, 5H), 2.8 (s, 3H), 2.9(d, 3H), 3.0(m, 1H), 3.7-3.95(m, 4H), 4.4(s, 2H), 4.7 (m, 1H), 6.7-6.8 (m, 3H), 7.5 (s, 1H).

EXAMPLE 24

This Example illustrates the preparation of 3-(1-{(3R)-3-(3,5-difluorophenyl)-3-[1-(methylsulfonyl)piperidin-4-yl]propyl}piperidin-4-yl)-5-(methylsulfonyl)-4,5,6,7-tetrahydro-3H-imidazo[4,5-c]pyridine (Compound 1 Table XI).

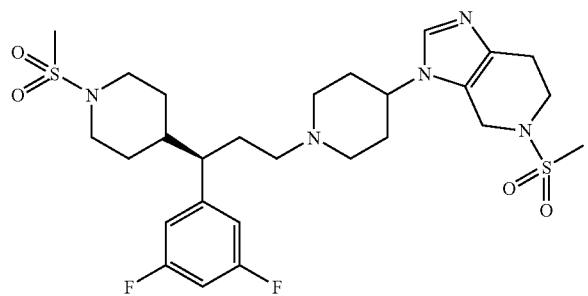

Step 1: Preparation of 3-(1-{(3R)-3-(3,5-difluorophenyl)-3-[1-(methylsulfonyl)piperidin-4-yl]propyl}piperidin-4-yl)-4,5,6,7-tetrahydro-3H-imidazo[4,5-c]pyridine.

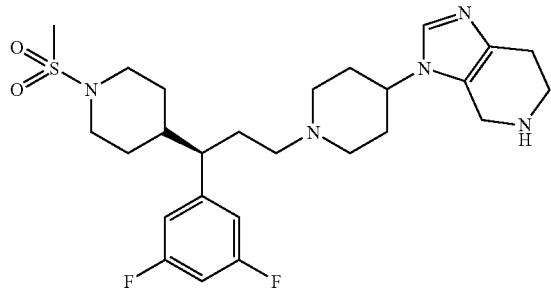

A solution of 3-(1-{(3R)-3-(3,5-difluorophenyl)-3-[1-(methylsulfonyl)piperidin-4-yl]propyl}piperidin-4-yl)-3H-imidazo[4,5-c]pyridine (Compound 19, Table II; 0.50 g) was dissolved in trifluoroacetic acid (50 ml), PtO$_2$ (75 mg) was added and the reaction mixture was heated to 70° C. with stirring under an atmosphere of hydrogen gas (65 psi) for 48 hours. The reaction mixture was filtered and solvents evaporated under reduced pressure to give a brown gum which was purified by SCX ion-exchange chromatography, eluting with a gradient of methanol then methanolic ammonia in methanol to give the title compound (0.34 g) as a pale yellow foam.

MS (ES) 522 (M+H)$^+$

NMR (DMSO$_{d6}$): 0.98-1.23 (m, 3H), 1.27-1.38 (m, 1H), 1.51-2.15 (m, 12H), 2.56-2.64 (m, 2H), 2.68-2.74 (m, 2H), 2.80 (s, 3H), 2.85-2.94 (m, 1H), 3.21-3.61 (m, 6H), 3.72-3.83 (m, 1H), 4.04 (s br, 2H), 6.95 (d, 2H), 7.03 (t, 1H).

Step 2: To a solution of 3-(1-{(3R)-3-(3,5-difluorophenyl)-3-[1-(methylsulfonyl)piperidin-4-yl]propyl}piperidin-4-yl)-4,5,6,7-tetrahydro-3H-imidazo[4,5-c]pyridine (0.155 g) in tetrahydrofuran (10 ml) cooled to 0° C. was added methanesulfonyl chloride (0.035 g, 0.024 ml) followed by triethylamine (0.034 g, 0.0476 ml). The resulting solution was left to stir at room temperature for 18 hours before being quenched with saturated brine, ethyl acetate was added and the layers separated. The aqueous portion was further extracted with ethyl acetate, the combined organic portions were washed with brine then the combined organic portions were dried (MgSO$_4$) and solvents evaporated under reduced pressure before purification of the residues by column chromatography using as eluent a gradient of methanol in dichloromethane, giving the title compound (0.066 g) as a white foam.

MS (ES) 600 (M+H)$^+$

NMR (CDCl$_3$): 1.23 (qd, 1H), 1.30-1.71 (m, 6H), 1.86-2.20 (m, 9H), 2.43 (t, 1H), 2.52 (t, 1H), 2.63 (t, 1H), 2.75 (s, 3H), 2.81 (t, 2H), 2.85 (s, 3H), 2.89 (d, 1H), 2.97 (d, H), 3.57-3.68 (m, 2H), 3.73 (d, 1H), 3.86 (d, 1H), 4.37 (s, 2H), 6.62-6.73 (m, 3H), 7.47 (s, 1H).

EXAMPLE 25

This Example describes the preparation of 4-{(1R)-1-(3,5-difluorophenyl)-3-[4-(3-isopropyl-5-methyl-4H-1,2,4-triazol-4-yl)piperidin-1-yl]butyl}-1-(methylsulphonyl)piperidine (Compound 1 Table IX).

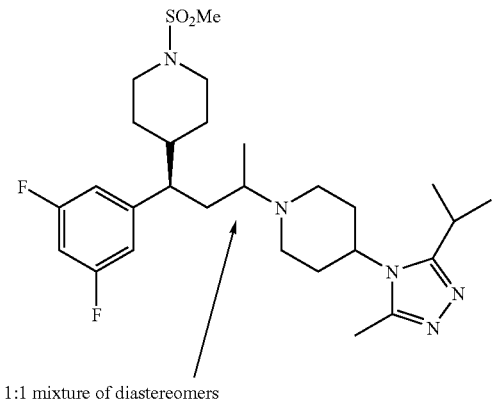

1:1 mixture of diastereomers

To a solution of (3R)-3-(3,5-difluorophenyl)-3-[1-(methylsulphonyl)piperidin-4-yl]propanal (0.45 g) and benzotriazole (160 mg) in anhydrous toluene (40 ml) was added 4-(3-isopropyl-5-methyl-4H-1,2,4-triazol-4-yl)piperidine (281 mg) and the mixture was refluxed overnight with a Dean-Stark trap. The reaction mixture was allowed to cool and a solution of methylmagnesium bromide in diethyl ether (3M, 2.25 ml) was added. The resulting mixture was heated at 60° C. for 3 hours. The mixture was poured into aqueous ammonium chloride (40 ml) and extracted with ethylacetate. The combined organic extracts were washed with brine and dried (MgSO$_4$). Concentration under reduced pressure gave the crude product as a 1:1 mixture of diastereomers. This oil was submitted to preparative HPLC (Merck 50 mm 10 μm Kromasil C8, DT0267 column. Eluting with A=H$_2$O/TFA 99.9/0.1, B=MeOH/TFA 99.9/0.1). The first isomer to be eluted from the column was dissolved in dichloromethane and ethereal HCl (2M) was added. Concentration under reduced pressure provided the hydrochloride salt of the title compound as a single diastereomer (44 mg). MH$^+$538.3, NMR (CD$_3$OD): 1.0-1.4 (m, 12H), 1.6 (m, 1H), 2.05 (m, 2H), 2.2 (m, 2H), 2.4 (t, 1H), 2.5 (t, 2H), 2.6-3.0 (9H, m), 3.3-3.5 (m, 4H), 3.5 (m, 2H), 3.7 (d, 1H), 4.8 (m, 1H), 6.8 (t, 1H), 6.9 (d, 2H).

The second isomer to be eluted from the column was dissolved in dichloromethane and ethereal HCl (2M) was added. Concentration under reduced pressure gave the hydrochloride salt of the corresponding diastereomer (51 mg)(Compound 2 Table IX). MH+538.3, NMR (CD$_3$OD) 1.0 (d, 3H), 1.1 (m, 1H), 1.4 (d, 6H), 1.45 (d, 1H), 1.6 (m, 1H), 1.8 (m, 1H), 2.0 (d, 2H), 2.6 (m, 4H), 2.7 (s, 3H), 2.8 (s, 3H), 2.9 (m, 3H), 3.2 (s, 1H), 3.4 (m, 1H), 3.5 (m, 1H), 3.6 (d, 2H), 3.7 (m, 2H), 4.9 (m, 1H), 6.8 (t, 1H), 6.9 (d, 2H).

EXAMPLE 26

This Example illustrates the preparation of 1-((3-exo)-8-{(3R)-3-(3,5-difluorophenyl)-3-[1-(methylsulfonyl)piperidin-4-yl]propyl}-8-azabicyclo[3.2.1]oct-3-yl)-1H-imidazo[4,5-c]pyridine (Compound 11 Table VI)

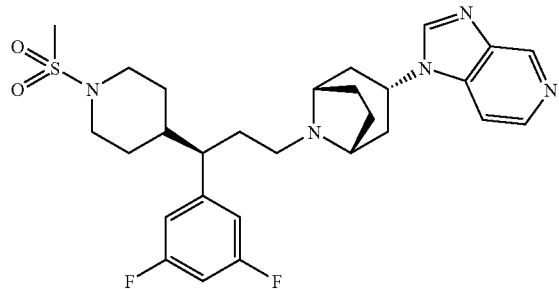

To a solution of (3R)-3-[1-(methylsulfonyl)piperidin-4-yl]-3-phenylpropan-1-ol (0.643 g) in dichloromethane (40 ml) was added Dess-Martin Periodinane (0.900 g). The reaction mixture was allowed to stir for 90 minutes before the addition of NaOH solution (1M, 50 ml). The reaction was stirred for 10 minutes then extracted with dichloromethane (50 ml). The organic portion was then re-extracted with NaOH solution (1M, 50 ml) then dried over MgSO$_4$ and filtered. The resulting solution was then treated with 1-[(3-exo)-8-azabicyclo[3.2.1]oct-3-yl]-1H-imidazo[4,5-c]pyridine (0.400 g) and polymer-supported triacetoxyborohydride resin (1.750 g @2.57 mmol/g) and left to stir for 18 hours. The material was then poured directly onto an SCX-2 ion-exchange cartridge, and purified using as eluent dichloromethane then methanol then methanolic ammonia, giving the title compound (0.709 g) as a white foam.

MS (ES) 544 (M+H)+

$^1$H NMR (400.132 MHz, CDCl$_3$) δ: 0.91-1.79 (m, 6H), 1.79-2.36 (m, 1H), 2.36-2.85 (m, 7H), 3.25-3.38 (m, 2H), 3.74 (d, 1H), 3.86 (d, 1H), 4.52 (t, 1H), 6.63-6.79 (m, 2H), 7.34 (d, 1H), 7.95 (s, 1H), 8.37 (s, 1H), 9.07 (s, 1H).

The 1-[(3-exo)-8-azabicyclo[3.2.1]oct-3-yl]-1H-imidazo[4,5-c]pyridine was prepared in a manner analogous to the preparation of 1-piperidin-4-yl-1H-imidazo[4,5-c]pyridine (Method O), but substituting (3-exo)-8-benzyl-8-azabicyclo[3.2.1]octan-3-amine in place of the tert-butyl-4-aminopiperidine-1-carboxylate in Step 2.

MS (ES) 229 (M+H)+

$^1$H NMR (400.132 MHz, DMSO) δ: 1.74-1.92 (m, 4H), 2.07-2.13 (m, 2H), 3.18 (s, 2H), 3.55 (s, 2H), 3.99-4.22 (m, 1H), 4.63-4.86 (m, 1H), 7.82 (d, 1H), 8.31 (d, 1H), 8.43 (s, 1H), 8.93 (s, 1H).

EXAMPLE 27

This Example illustrates the preparation of methyl 1-((3-exo)-8-{(3R)-3-(3,5-difluorophenyl)-3-[1-(methylsulfonyl)piperidin-4-yl]propyl}-8-azabicyclo[3.2.1]oct-3-yl)-1,4,6,7-tetrahydro-5H-imidazo[4,5-c]pyridine-5-carboxylate (Compound 12 Table VI).

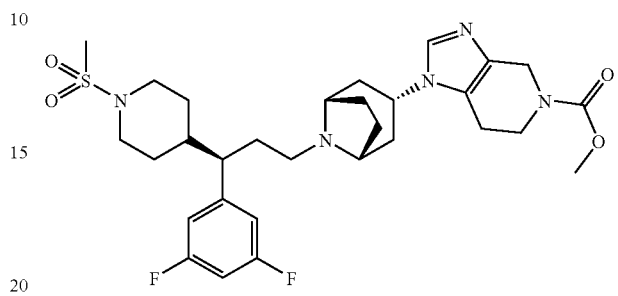

To a solution of methyl 1-((3-exo)-8-{(3R)-3-(3,5-difluorophenyl)-3-[1-(methylsulfonyl)piperidin-4-yl]propyl}-8-azabicyclo[3.2.1]oct-3-yl)-1,4-dihydro-5H-imidazo[4,5-c]pyridine-5-carboxylate (0.150 g) in methanol was added 20% Pd(OH)$_2$ (75 mg). The reaction vessel was purged to vacuum until the solvent started to boil, then H$_2$ gas was introduced from a balloon. This was repeated 3 times, then the reaction was left to stir under an atmosphere of H$_2$ gas for 2 hours. The reaction mixture was filtered under suction through a pad of celite then evaporation of the filtrate solution under reduced pressure gave a white foam which was first purified by reverse-phase HPLC using a gradient of (0.1% trifluoroacetic acid in acetonitrile) in (0.1% trifluoroacetic acid in water) giving a white foam, then passed through an SCX-2 ion-exchange cartridge, using as eluent dichloromethane then methanol then methanolic ammonia, giving the title compound (0.031 g) as a white foam.

MS (ES) 606 (M+H)+

$^1$H NMR (400.132 MHz, CDCl$_3$) δ: 1.19-2.03 (m, 17H), 2.10-2.21 (m, 2H), 2.46-2.66 (m, 4H), 2.75 (s, 3H), 3.24 (s, 2H), 3.64-3.90 (m, 6H), 3.99-4.08 (m, 1H), 4.48 (s, 2H), 6.62-6.74 (m, 3H), 7.40 (s, 1H).

The methyl 1-((3-exo)-8-{(3R)-3-(3,5-difluorophenyl)-3-[1-(methylsulfonyl)piperidin-4-yl]propyl}-8-azabicyclo[3.2.1]oct-3-yl)-1,4-dihydro-5H-imidazo[4,5-c]pyridine-5-carboxylate used above was prepared in the following manner:

To a solution of 1-((3-exo)-8-{(3R)-3-(3,5-difluorophenyl)-3-[1-(methylsulfonyl)piperidin-4-yl]propyl}-8-azabicyclo[3.2.1]oct-3-yl)-1H-imidazo[4,5-c]pyridine (0.140 g) in ethanol (10 ml), cooled to −78° C., was added methyl chloroformate (0.030 g, 0.025 ml). The resulting solution was left to stir for 40 minutes before addition of a solution of lithium borohydride (2M solution in THF, 0.20 ml) then left to stir for 2 hours before being warmed to room temperature. The reaction was quenched by addition of saturated ammonium chloride solution (5 ml) then diluted with dichloromethane (25 ml). The resulting white suspension was filtered under suction, the filtrate being further washed with saturated ammonium chloride solution (10 ml) before being dried over MgSO$_4$ and filtered. Evaporation of solvents under reduced pressure gave the product (0.153 g) as a clear glass.

MS (ES) 604 (M+H)+

EXAMPLE 28

This Example illustrates the preparation of 1-((3-endo)-8-{(3R)-3-(3,5-difluorophenyl)-3-[1-(methylsulfonyl)piperidin-4-yl]propyl}-8-azabicyclo[3.2.1]oct-3-yl)-1H-imidazo[4,5-c]pyridine (Compound 28 Table VI).

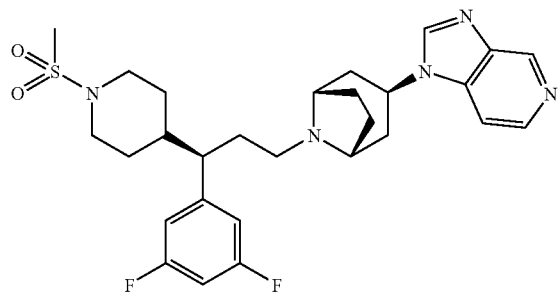

To a solution of (3R)-3-[1-(methylsulfonyl)piperidin-4-yl]-3-phenylpropan-1-ol (0.247 g) in dichloromethane (10 ml) was added Dess-Martin Periodinane (0.343 g). The reaction mixture was allowed to stir for 90 minutes before the addition of NaOH solution (1M, 50 ml). The reaction was stirred for 10 minutes then extracted with dichloromethane (50 ml). The organic portion was then re-extracted with NaOH solution (1M, 50 ml) then dried over $MgSO_4$ and filtered. The resulting solution was then treated with 1-[(3-endo)-8-azabicyclo[3.2.1]oct-3-yl]-1H-imidazo[4,5-c]pyridine (0.090 g) and polymer-supported triacetoxyborohydride resin (0.377 g @2.57 mmol/g) and left to stir for 18 hours. The material was then poured directly onto an SCX-2 ion-exchange cartridge, and purified using as eluent dichloromethane then methanol then methanolic ammonia, giving the title compound (0.103 g) as a white foam.

MS (ES) 544 (M+H)$^+$ $^1$H NMR (400.132 MHz, $CDCl_3$) δ: 1.26-1.60 (m, 6H), 1.65-1.84 (m, 3H), 1.95-2.12 (m, 6H), 2.46-2.68 (m, 5H), 2.75 (s, 3H), 3.26-3.33 (m, 2H), 3.76 (d, 1H), 3.89 (d, 1H), 4.62-4.71 (m, 1H), 6.65-6.72 (m, 3H), 7.34 (d, 1H), 8.04 (s, 1H), 8.43 (d, 1H), 9.11 (s, 1H).

The 1-[(3-endo)-8-azabicyclo[3.2.1]oct-3-yl]-1H-imidazo[4,5-c]pyridine was prepared in a manner analogous to the preparation of 1-piperidin-4-yl-1H-imidazo[4,5-c]pyridine (Method O), but substituting tert-butyl (3-endo)-3-amino-8-azabicyclo[3.2.1]octane-8-carboxylate in place of the tert-butyl-4-aminopiperidine-1-carboxylate in Step 2.

Method A 5-(Methylsulfonyl)-1-piperidin-4-yl-1H-benzimidazole

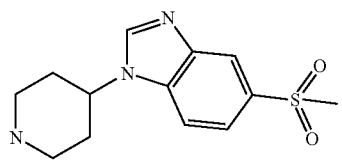

Step 1: 4-Amino-1-benzylpiperidine (87 g) was added slowly during 20 minutes to a stirred mixture of 2-fluoro-5-methylsulphonyl-nitrobenzene (100 g) and anhydrous sodium carbonate (35 g) in 500 mL DMSO, the internal temperature rose from 20° C. to 50° C. The mixture was stirred at 90° C. for 12 hours, then poured into ice/water and the yellow solid was filtered off, redissolved in dichloromethane, dried and evaporated to give 175 g N-(1-benzylpiperidin-4-yl)-2-nitro-4-methylsulphonylaniline.

Step 2: The crude material from Step 1 (170 g) was dissolved in 3 liters of methanol in a pressure vessel, 20 g of moist 5% Pd/C catalyst was added and stirred under an atmosphere of hydrogen at 3 bar and 50° C. for one hour. The reaction was cooled, filtered and evaporated to give 133 g N-(1-benzylpiperidin-4-yl)-2-amino-4-methylsulphonylaniline as a brown solid.

Step 3: The crude material from Step 2 (130 g) was stirred in 300 mL trimethylorthoformate containing 4-toluenesulphonic acid (8 g) at 90° C. for one hour, and collecting the methanol distillate. The reaction was cooled and filtered to give 108 g 1-(1-benzylpiperidin-4-yl)-5-methylsulphonyl-1H-benzimidazole as a brown solid.

Step 4: The crude material from Step 3 (100 g) was dissolved in 1 liter of methanol in a pressure vessel, 20 g of moist 10% Pd/C catalyst and 100 mL acetic acid were added and stirred under an atmosphere of hydrogen at 5 bar and 50° C. for 8 hours. The reaction was cooled, filtered and evaporated. The residue was dissolved in water and basified with sodium hydroxide solution, extracted into dichloromethane, dried and evaporated. The brown solid was triturated with isopropanol, filtered, and washed with ether to give the title compound (60 g) as a pale grey solid; NMR: 2.00(m, 4H), 2.75(m, 2H), 3.15(m, 2H), 3.20(s, 3H), 4.60 (m, 1H), 7.78 (dd, 1H), 7.85(d, 1H), 8.20(d, 1H), 8.56(s, 1H).

Method B 4-(3-iso-Propyl-5-methyl-[1,2,4]triazol-4-yl)-piperidine

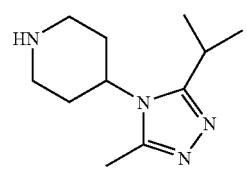

Step 1: To a solution of the 2-methyl-N-[1-(phenylmethyl)-4-piperidinyl]-propanamide (5.89 g) in pyridine (11.2 mL) and chloroform (15 mL) at 0° C. under argon was added phosphorus oxychloride (6.33 mL). The mixture was allowed to warm to ambient temperature and stirred for 24 hours then evaporated. The residue was dissolved in chloroform (30 mL) and acetic hydrazide (3.36 g) added and the mixture heated at reflux for 5 hrs, diluted with saturated sodium hydrogen carbonate and extracted with dichloromethane, dried ($MgSO_4$) and evaporated. The residue was dissolved in 6M HCl (30 mL) and heated at reflux for 21 hours and then evaporated. Saturated potassium carbonate (300 mL) was added and extracted with dichlo romethane, the organic layer was washed with brine, dried (MgSO$_4$) and evaporated. The resulting yellow oil was purified on silica (90 g) using 2% of a 7M ammonia solution in methanol in 98% dichloromethane to give a yellow solid (3.04 g); NMR (CDCl$_3$): 1.40 (d, 6H), 1.80 (m, 2H), 2.0-2.3 (m, 5H), 2.55 (s, 3H), 3.0-3.1 (m, 3H), 3.55 (s, 2H), 3.85 (m, 1H), 7.25-7.35 (m, 5H).

Step 2: The N-benzylpiperidine triazole (3.03 g) was dissolved in ethanol (50 mL) and 20% palladium hydroxide (0.70 g) and ammonium formate (3.22 g) added and the mixture heated at reflux for 150 minutes. The suspension was filtered through celite and the filtrate evaporated to give the product as a yellow solid (2.20 g). NMR (CDCl$_3$): 1.2 (d, 6H), 1.7 (m, 2H), 1.9 (m, 2H), 2.1 (br s, 1H), 2.4 (s, 3H), 2.6 (t, 2H), 3.0 (m, 2H), 3.1 (m, 1H), 4.0 (m, 1H).

Method C

Preparation of 2-methyl-5-(methylsulfonyl)-1-piperidin-4-yl-1H-benzimidazole

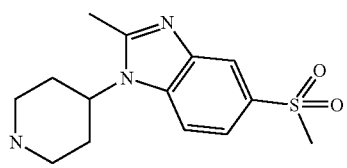

Step 1: Preparation of tert-butyl 4-{[4-(methylsulfonyl)-3-nitrophenyl]amino}piperidine-1-carboxylate.

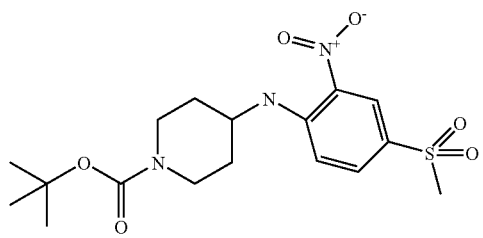

To a solution of tert-butyl 4-aminopiperidine-1-carboxylate (1.36 g) in dimethyl sulphoxide (30 ml) was added 2-fluoro-5-methylsulfonylnitrobenzene (1.5 g) followed by anhydrous potassium carbonate (4 g) and the resulting mixture was heated to 90° C. for 18 hours. The mixture was cooled, quenched with water (100 ml) and extracted with ethyl acetate (×3). The organics were dried and evaporated to dryness to give the title compound, which was used without further purification. Yield 2.72 g.

NMR (d6 DMSO) 1.4 (s, 9H), 1.55 (m, 2H), 1.95 (m, 2H), 2.5 (m, 2H), 3.9 (m, 1H), 7.4 (d, 1H), 7.9 (dd, 1H), 8.3 (d, 1H), 8.5 (d, 1H).

Step 2: Preparation of tert-butyl 4-[2-methyl-5-(methylsulfonyl)-1H-benzimidazol-1-yl]piperidine-1-carboxylate

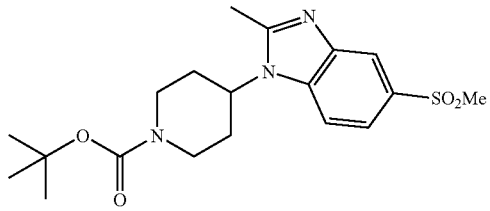

To a solution of tert-butyl 4-{[4-(methylsulfonyl)-3-nitrophenyl]amino}piperidine-1-carboxylate (2 g) in methanol/acetic acid (100 ml) was added trimethyl orthoacetate (0.7 ml) followed by a catalytic amount of 10% palladium on carbon. The resulting mixture was placed under a hydrogen atmosphere (3 bar) and heated to 80° C. for 16 hours. The mixture was cooled, filtered and evaporated to dryness. The resulting solid was purified by chromatography on silica eluting with a gradient of dichloromethane to 5% methanol/dichloromethane to give the title compound as a solid. Yield 1.32 g.

NMR (d6 DMSO) 1.5 (s, 9H), 1.9 (m, 2H), 2.2 (m, 2H), 2.7 (s, 3H), 3.0 (m, 2H), 3.2 (s, 3H), 4.15 (m, 2H), 4.65 (m, 1H), 7.7 (dd, 1H), 7.8 (d, 1H), 8.05 (d, 1H).

Step 3: Preparation of 2-methyl-5-(methylsulfonyl)-1-piperidin-4-yl-1H-benzimidazole The title compound was prepared in a similar manner to Method O, Step 5.

NMR (d6 DMSO) 2.2 (m, 2H), 2.85 (m, 2H), 2.9 (s, 3H), 3.15 (m, 2H), 3.3 (s, 3H), 3.5 (m, 2H), 5.0 (m, 1H), 8.0 (dd, 1H), 8.39s, 1H), 8.7 (d, 1H), 9.2 (d, 1H), 9.9 (m, 1H).

Method D 4-(3-Benzyl-[1,2,4]oxadiazol-5-yl)-piperidine hydrochloride

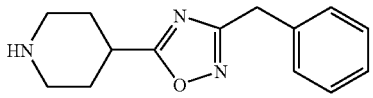

This was prepared from N'-hydroxy-2-phenylethanimidamide and 1-(tert-butoxycarbonyl)piperidine-4-carboxylic acid using a similar method to that used to prepare 4-{3-[4-(methylthio)benzyl]-1,2,4-oxadiazol-5-yl}piperidine hydrochloride (Method E, Steps 1, 2); NMR: 1.96 (2H, m), 2.15 (2H, dd), 3.01(2H, t), 3.24 (2H, dd), 3.40 (1H, m), 4.09 (2H, s), 7.25 (5H, m), 9.31(2H, br s); MS: 244 (MH+).

Method E

4-{3-[4-(methylthio)benzyl]-1,2,4-oxadiazol-5-yl}piperidine hydrochloride

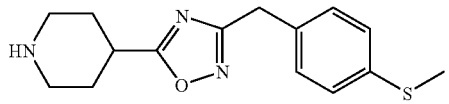

1-(tert-Butoxycarbonyl)piperidine-4-carboxylic acid (1.00 g, 4.36 mmol), 1-hydroxybenzotriazole (589 mg, 4.36 mmol) and N-methylmorpholine(0.97 mL, 8.72 mmol) were dissolved in dicloromethane (50 mL), under argon, and (3-dimethylaminopropyl)carbodiimide hydrochloride (921 mg, 8.72 mmol) and N'-hydroxy-2-[4-(methylthio)phenyl] ethanimidamide (855 mg, 4.36 mmol) were added. The mixture was stirred at room temperature for 92 hours. The organics were washed with sodium hydroxide (0.1 N) and citric acid (0.5M), dried (phase separating filter) and the solvent evaporated to give a yellow oil which was redissolved in 1,4-dioxane (100 mL) and heated to reflux for 5 hours, cooled and the solvent evaporated and chromatographed (50 g Silica Isolute, eluent 20% ethyl acetate/isohexane) to give a yellow oil, tert-butyl 4-{3-[4-(methylthio)benzyl]-1,2,4-oxadiazol-5-yl}piperidine-1-carboxylate (920 mg, 54%); NMR (CDCl$_3$): 1.46 (9H, s), 1.71-1.87 (2H, m), 2.03 (2H, m), 2.48 (3H, m), 2.92 (2H, t), 3.05 (1H, m), 4.00 (2H, s), 4.07 (2H, m), 7.24 (4H, m).

Step 2: Acetyl chloride (86 µL, 1.21 mmol) was added dropwise to methanol (0.5 mL) and stirred for 10 minutes then added to tert-butyl 4-{3-[4-(methylthio)benzyl]-1,2,4-oxadiazol-5-yl}piperidine-1-carboxylate (237 mg, 0.61 mmol) in MeOH (5 mL) and the mixture heated to 60° C. for 1 hour and the solvents evaporated to give a the title compound as a yellow powder, (199 mg, 100%); MS: 290 (MH+).

Method F

4-{3-[4-(Methylsulphonyl)benzyl]-1,2,4-oxadiazol-5-yl}piperidine

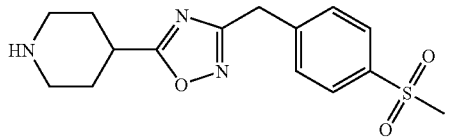

Step 1: tert-Butyl 4-{3-[4-(methylthio)benzyl]-1,2,4-oxadiazol-5-yl}piperidine-1-carboxylate (3.10 g, 7.96 mmol) (Method E, Step 1) was dissolved in dichloromethane (100 mL), at room temperature, under argon. 3-Chloroperbenzoic acid (60% wt, 6.87 g, 23.88 mmol) was added portionwise and stirred for 1 hour. Sodium metabisulfite (1M, 250 mL) was added and stirred and the organics separated and washed with 1N sodium hydroxide and brine, dried (MgSO$_4$) and solvents evaporated to a clear oil which crystallised upon addition of diethyl ether (50 mL). The solid was filtered, washed with a minimum of diethyl ether and dried to give tert-butyl 4-{3-[4-(methylsulfonyl)benzyl]-1,2,4-oxadiazol-5-yl}piperidine-1-carboxylate as a white fluffy solid (2.61 g, 78% yield); NMR (CDCl$_3$): 1.46 (9H, s), 1.61 (3H, s), 1.79 (2H, m), 2.04 (2H, m), 2.93 (2H, m), 3.04 (3H, s), 4.15 (2H, s), 7.53 (2H, d), 7.90 (2H, d).

Step 2: Acetyl chloride (0.97 mL, 11.86 mmol) was added dropwise to methanol (10 mL), stirred for 10 minutes and tert-butyl 4-{3-[4-(methylsulfonyl)benzyl]-1,2,4-oxadiazol-5-yl}piperidine-1-carboxylate (2.50 g, 5.93 mmol) was added and the mixture heated to reflux for 2 hours. The solvents were evaporated and the residue triturated with diethyl ether, filtered and dried to give the title compound as a fine white powder (2.05 g, 97%); NMR 1.97 (2H, m), 2.17(2H, dd), 3.02(2H, m), 3.31 (2H, m), 3.41 (1H, m), 4.25 (2H, s), 7.59 (2H, d), 7.89 (2H, d), 9.27(1H, br s), 9.35 (1H, br s); MS: 322 (MH+).

Method G

1-[(3R)-3-Chloro-3-phenylpropyl]-4-(3-isopropyl-5-methyl-4H-1,2,4-triazol-4-yl)piperidine

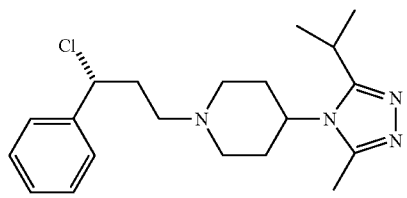

Step 1: Potassium carbonate (276 mg) was added to a solution of (3S)-3-hydroxy-3-phenylpropyl 4-methylbenzenesulfonate (306 mg) and 4-(3-isopropyl-5-methyl-4H-1,2,4-triazol-4-yl)piperidine (208 mg) in dioxane (5 ml) and the mixture was heated and stirred at 100° C. for 11 hours. The reaction mixture was evaporated to dryness and the residue was partitioned between dichloromethane and water (20 ml of each). The organic layer was collected and washed with water (10 ml), brine (10 ml) and dried. The crude product was purified by chromatography on silica eluted with a solvent gradient (ethyl acetate-30% methanol/ethyl acetate) to give (1S)-3-[4-(3-isopropyl-5-methyl-4H-1,2,4-triazol-4-yl)piperidin-1-yl]-1-phenylpropan-1-ol, yield 104 mg, M+H 343, NMR (CDCl$_3$): 1.37 (6H, d), 1.92 (4H, m), 2.03 (1H, m), 2.22 (3H, m), 2.52 (3H, s), 2.61 (1H, m), 2.73 (1H, m), 3.01 (1H, d), 3.21 (1H, m), 3.32 (1H, d), 3.91 (1H, m), 4.92 (1H, dd), 7.22 (1H, m), 7.36 (4H, m).

Step 2: Triethylamine (127 µl) was added to a solution of (1S)-3-[4-(3-iso-propyl-5-methyl-4H-1,2,4-triazol-4-yl) piperidin-1-yl]-1-phenylpropan-1-ol (238 mg) in dichloromethane (3 ml) at 0° C. followed by methanesulphonyl chloride (61 µl). The reaction mixture was allowed to warm to room temperature and was stirred for 48 hours. The reaction mixture was diluted with an equal volume of dichloromethane and washed with saturated ammonium chloride (2×10 ml) and brine (10 ml) and dried. Evaporation of the solvent gave the title compound, yield 252 mg, M+H 361.

Method H

Preparation of (3R)-3-(3,5-difluorophenyl)-3-[1-(methylsulfonyl)piperidin-4-yl]propanal

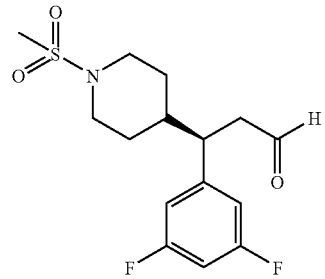

Step 1: Preparation of (2E)-3-[1-(methylsulfonyl)piperidin-4-yl]acryloyl chloride.

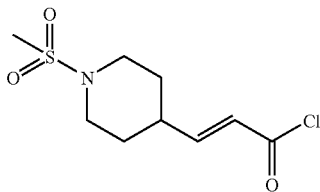

Oxalyl chloride (5.1 g) was added to a solution of (2E)-3-[1-(methylsulfonyl)piperidin-4-yl]acrylic acid (9.4 g) in dichloromethane containing 2-3 drops of DMF and the mixture was stirred at room temperature for 1.5 hours. The reaction mixture was evaporated to dryness and the residue obtained was used directly in the next step.

Step 2: Preparation of (4R,5S)-1,5-dimethyl-3-{(2E)-3-[1-(methylsulfonyl)piperidin-4-yl]prop-2-enoyl}-4-phenylimidazolidin-2-one.

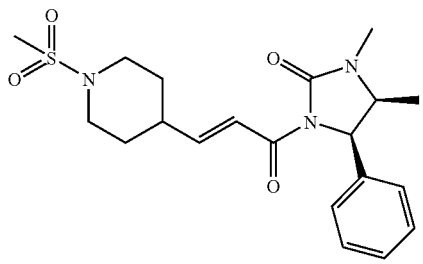

Lithium bis(trimethylsilyl)amide (8 ml of a 1M solution in THF) was added dropwise to a suspension of (4R,5S)-1,5-dimethyl-4-phenyl-2-imidazolidinone (1.52 g) in THF (20 ml) under argon at −10° C. The reaction mixture was stirred at −10° C. for 10 minutes, allowed to warm to 0° C. and maintained at this temperature for 10 minutes then cooled again to −10° C. The solution of the acid chloride (2 g dissolved in 10 ml of dichloromethane) prepared in Step 1 was added dropwise and the reaction mixture was allowed to warm to room temperature and washed with water (100 ml). The aqueous extract was extracted with ethyl acetate (3×50 ml) and the ethyl acetate extracts were dried and the residue passed through a 90 g Biotage column eluting with a solvent gradient (50% ethyl acetate/isohexane-70% ethyl acetate/isohexane). Yield 1.89 g. LC-MS MH+406, NMR (CDCl₃): 0.8 (d, 3H), 1.5-1.6 (m, 3H), 1.9 (m, 2H), 2.3 (m, 1H), 2.7 (m, 2H), 2.75 (s, 3H), 2.8 (s, 3H), 3.75 (m, 2H), 3.9 (m, 1H), 5.3 (d, 1H), 6.85 (d-d, 1H), 7.1 (d, 1H), 7.2-7.35 (m, 3H), 7.45 (d, 1H).

Step 3: Preparation of (4S,5R)-1-{(3R)-3-(3,5-difluorophenyl)-3-[1-(methylsulfonyl)piperidin-4-yl]propanoyl}-3,4-dimethyl-5-phenylimidazolidin-2-one.

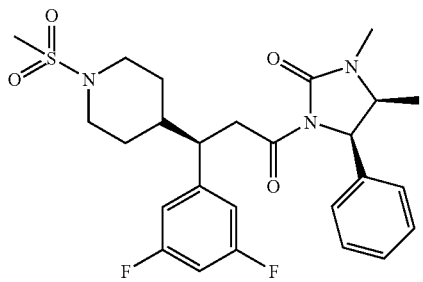

Step A: TMEDA (11.6 g) was added to a suspension of copper iodide (19.4 g) in THF (240 ml) under argon and the mixture was stirred for 45 minutes then cooled to −70° C. A solution of 3,5-difluorophenyl magnesium bromide in THF (201.1 ml of a 0.5M solution in THF) was added over 10 minutes and a mixture was stirred at −70° C. for 30 minutes.

Step B: Di-n-butylboron triflate (100.7 ml of 1M solution in dichloromethane) was added to a suspension of (4R,5S)-1,5-dimethyl-3-{(2E)-3-[1-(methylsulfonyl)piperidin-4-yl]prop-2-enoyl}-4-phenylimidazolidin-2-one (20.41 g; Step 2) in THF maintained at −40° C. and stirring was continued for 10 minutes and the mixture was cooled to −70° C. and added via a cannula to the cuprate suspension prepared in step A. The reaction mixture was stirred at −70° C. for 1 hour, allowed to warm to room temperature, then saturated ammonium chloride solution (200 ml) was added. The THF was evaporated and ethyl acetate (200 ml) was added. Air was blown through this mixture for 1 hour. The ethyl acetate layer was collected and the aqueous portion was extracted with ethyl acetate (2×100 ml). The combined ethyl acetate extracts were washed with saturated ammonium chloride solution (2×100 ml), dried and evaporated to dryness. The residue was purified by chromatography on silica eluting with a solvent gradient of ethyl acetate-isohexane (1:1) to neat ethyl acetate to give the title compound as a white solid, yield 25 g, NMR (CDCl₃) 0.78 (d, 3H) 1.2-1.6 (m, 6H) 1.9 (m, 1H) 2.4-2.65 (m, 2H) 2.75 (s, 3H) 2.85 (s, 3H) 3-3.2 (m, 2H) 3.7-3.9 (m, 4H) 5.2 (d, 1H) 6.6(m, 3H) 6.85 (m, 2H) 7.2 (m, 3H).

Step 4: Preparation of (3R)-3-(3,5-difluorophenyl)-3-[1-(methylsulfonyl)piperidin-4-yl]propan-1-ol

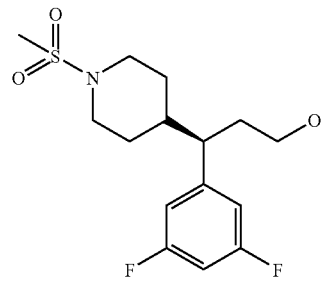

Lithium borohydride (48 ml of 2M solution in THF) was added to a solution of (4S,5R)-1-{(3R)-3-(3,5-difluorophenyl)-3-[1-(methylsulfonyl)piperidin-4-yl]propanoyl}-3,4-dimethyl-5-phenylimidazolidin-2-one (25 g) in THF (200 ml) and the mixture was heated at 70° C. for 3 hours then allowed to cool to room temperature and stirring was continued for 16 hours. Ethanol was added carefully (20 ml) and the reaction mixture was acidified to pH 4 by addition of 2M HCl. The THF was evaporated and the residue dissolved in dichloromethane (100 ml) and this was washed with water (100 ml) and dried. The solvent was removed and the product was purified by chromatography on a Biotage 65 column eluted with a 1:1 mixture of ethyl acetate/isohexane. Yield 13 g, NMR (CDCl₃) 1.2-1.8 (m, 5H) 1.95-2.2 (m, 2H) 2.5-2.7 (m, 3H) 2.75 (s, 3H) 3.3-3.6 (m, 2H) 3.7-3.9 (m, 2H) 6.65 (m, 3H).

Step 5: Preparation of Title Compound

Dess-Martin periodinane (1 g) was added to a solution of (R)3-(N-methanesulphonyl-piperidin-4-yl)-3-(3,5-difluorophenyl)propanol (0.8 g) in dichloromethane (40 ml) and the mixture was stirred for 1.5 hours. The reaction mixture was washed with 2M NaOH (2×20 ml) and dried. The solution of the title compound in dichloromethane was used in subsequent reactions.

In a similar manner but starting from (2E)-3-[1-(trifluoromethylsulfonyl)piperidin-4-yl]acrylic acid in step 1 was prepared (3R)-3-(3,5-difluorophenyl)-3-[1-(trifluoromethylsulfonyl)piperidin-4-yl]propanal.

Method I

Preparation of 3-phenyl-3-(1-tert-butylcarbonyloxypiperidin-4-yl)propionaldehyde

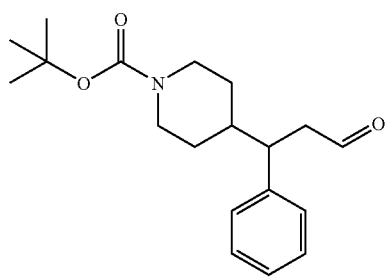

Step 1: Preparation of 1-tert-butylcarbonyloxy-4-benzoylpiperidine

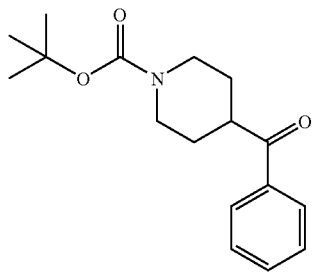

To a solution of 4-benzoylpiperidine (6 g, 26.5 mmol) in 2M aqueous sodium hydroxide (26.5 mL) was added di-tert-butyl dicarbonate (5.79 g, 26.5 mmol) and the resulting mixture was stirred at room temperature for 18 h. The solid product was isolated by filtration and dried under vacuum at 40° C. giving the sub-titled compound (7 g); NMR: 1.3-1.4 (m, 11H) 1.7 (m, 2H) 2.9 (m, 2H) 3.6 (m, 1H) 3.95 (m, 2H) 7.5-7.6 (m, 3H) 7.95 (d, 2H).

Step 2: Preparation of ethyl 3-phenyl-3-(1-tert-butylcarbonyloxypiperidin-4-yl)acrylate

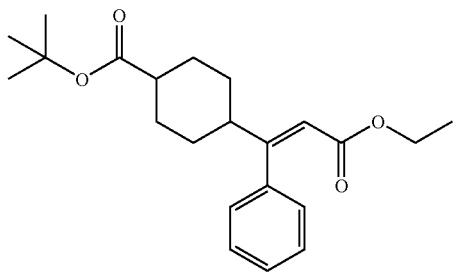

To a solution of triethylphosphonoacetate (6.2 g, 27 mmol) in THF (100 mL) at 0° C. was added lithium bis(trimethylsilyl)amide (32.5 mL, 1M, 32.5 mmol). The resulting mixture was stirred at 0° C. for 20 min. 1-tert-Butylcarbonyloxy-4-benzoylpiperidine (7 g, 25 mmol) was added and the resulting mixture was stirred at room temperature for 48 h. The mixture was evaporated and the residue dissolved in ethyl acetate (200 mL). The solution was washed with 2M hydrochloric acid (2×100 mL), dried and evaporated giving the sub-titled compound.

Step 3: Preparation of ethyl 3-phenyl-3-(1-tert-butylcarbonyloxypiperidin-4-yl)propionoate

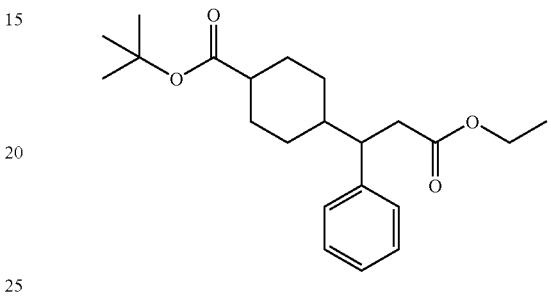

Ethyl 3-phenyl-3-(1-tert-butylcarbonyloxypiperidin-4-yl) acrylate (~25 mmol) was dissolved in ethanol (200 mL) and the solution purged with argon. 20% Palladium hydroxide (2 g) was added and the resulting mixture was stirred at room temperature under an atmosphere of hydrogen (balloon) for 72 h. The mixture was purged with argon, filtered and the filtrate evaporated. The crude product was purified by silica gel chromatography (eluent:isohexane then 35% ethyl acetate in isohexane) to give the sub-titled compound (5.3 g).

Step 4: Preparation of 3-phenyl-3-(1-tert-butylcarbonyloxypiperidin-4-yl)propan-1-ol

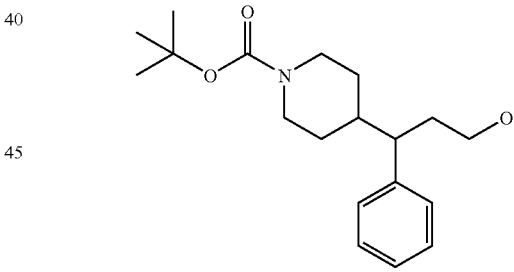

To a solution of ethyl 3-phenyl-3-(1-tert-butylcarbonyloxypiperidin-4-yl)propionoate (5.3 g, 14.6 mmol) in THF (100 mL) was added lithium aluminium hydride (14.6 mL, 1M, 14.6 mmol) dropwise over 20 min. The resulting mixture was stirred at 0° C. for 1 h. 2M aqueous sodium hydroxide (20 mL) was added dropwise. The mixture was filtered through Celite®, washing with ethyl acetate (3×25 mL). The filtrate and washings were combined and evaporated. The residue was dissolved in ethyl acetate (100 mL) and the resulting solution washed with water (3×50 mL), dried and evaporated to give the sub-titled compound (4.6 g); NMR: 0.9-1 (m, 2H) 1.25 (m, 1H) 1.35 (s, 9H) 1.5-2 (m, 5H) 2.6 (m, 2H) 3.1 (m, 2H) 3.8-4 (m, 2H) 4.2 (t, 1H).

Step 5: Preparation of the Title Compound

To a solution of 3-phenyl-3-(1-tert-butylcarbonyloxypiperidin-4-yl)propan-1-ol (4.6 g, 14.4 mmol) in DCM (100 mL)

was added Dess-Martin periodinane (6.1 g, 14.6 mmol) and the resulting mixture was stirred at room temperature for 2 h. The mixture was washed with 2M aqueous sodium hydroxide (3×50 mL), dried and evaporated to give the title compound.

Method J

Preparation of 4-(3-isopropyl-5-methyl-4H-1,2,4-triazol-4-yl)-1-(3-phenyl-3-piperidin-4-ylpropyl)piperidine

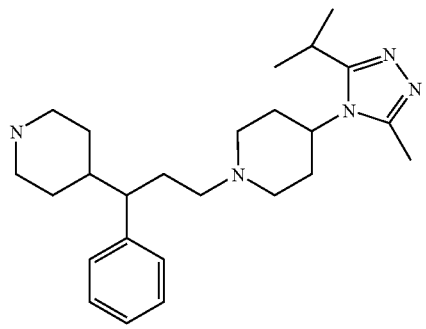

Step 1: Preparation of tert-butyl 4-{3-[4-(3-isopropyl-5-methyl-4H-1,2,4-triazol-4-yl)piperidin-1-yl]-1-phenylpropyl}piperidine-1-carboxylate

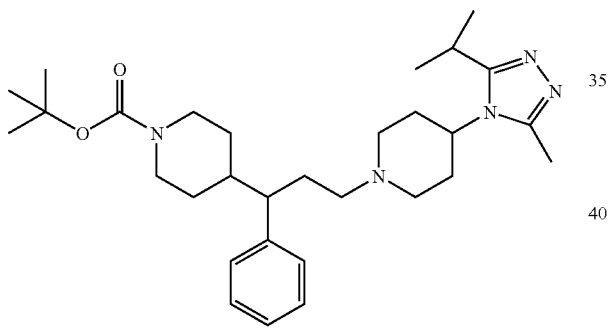

Sodium triacetoxyborohydride (874 mg) was added to a solution of 4-(3-isopropyl-5-methyl-4H-1,2,4-triazol-4-yl)piperidine (572 mg) and 3-phenyl-3-(1-tert-butylcarbonyloxypiperidin-4-yl)propionaldehyde (800 mg, prepared by Method I, Step 5) in dichloromethane (15 ml) at 0° C. followed by 5 drops of acetic acid. The mixture was allowed to warm to room temperature and was stirred for 2 hours then diluted with dichloromethane (100 ml) and washed with 2M NaOH (2×100 ml), water (100 ml) and brine (100 ml) and dried. The residue obtained on removal of the solvent was passed through a Biotage 40 g silica column eluting with a mixture of 2% methanolic ammonia and dichloromethane, yield 790 mg, NMR (CDCl$_3$): 0.97 (1H, m), 1.14 (1H, m), 1.30 (1H, m), 1.33 (6H, d), 1.40 (9H, s), 1.56 (1H, m), 1.67-2.10 (10H, m), 2.33 (1H, m), 2.48 (3H, s), 2.50 (1H, t), 2.67 (1H, t), 2.96 (3H, m), 3.80 (1H, m), 3.93 (1H, m), 4.09 (1H, m), 7.08 (2H, d), 7.19 (1H, t), 7.27 (2H, m). MS 510 (M+H).

Step 2: Preparation of the Title Compound

The product from step 1 was dissolved in dichloromethane (1.5 ml) and trifluoroacetic acid (15 ml) was added and the mixture was allowed to stand for 1 hour. The reaction mixture was evaporated to dryness and the residue was dissolved in 2M NaOH (50 ml) and this solution was extracted with dichloromethane (2×50 ml). The organics were evaporated to dryness to give the title compound as a yellow oil, yield 578 mg, NMR (CDCl$_3$): 1.11 (1H, m), 1.29 (1H, m), 1.31 (6H, d), 1.55 (1H, m), 1.66-2.20 (10H, m), 2.33 (1H, m), 2.48 (1H, m), 2.49 (3H, s), 2.62 (1H, t), 2.98 (4H, m), 3.18 (1H, m), 3.60 (2H, m), 3.80 (2H, m), 7.08 (2H, d), 7.19 (1H, t), 7.28 (2H, m).

Method K

Preparation of ethyl 2-piperidin-4-yl-1,3-thiazole-4-carboxylate

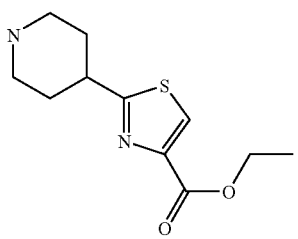

Step 1: Preparation of benzyl 4-[4-(ethoxycarbonyl)-1,3-thiazol-2-yl]piperidine-1-carboxylate

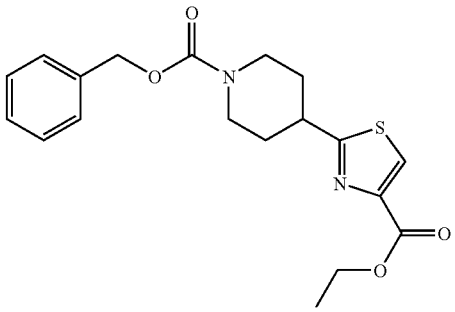

Ethyl bromopyruvate (1.61 ml) was added to a suspension of benzyl 4-(aminocarbonothioyl)piperidine-1-carboxylate [CAS number 167757-46-2] (2.32 g) in ethanol (25 ml) and the mixture was stirred for 6 hours. The residue obtained on removal of the solvent was used directly in Step 2.

Step 2: Preparation of Title Compound

The product from step 1 was added to 33% HBr in acetic acid (35 ml) and the mixture was stirred for 1 hour. A further aliquot of HBr in acetic acid was added and stirring was continued for 1 hour. The reaction mixture was diluted with diethyl ether (100 ml) and the solids filtered. The solid was dissolved in dichloromethane (100 ml) and triethylamine (2 ml) and MP-carbonate (10 g) were added and the mixture was stirred for 16 hours, filtered and the filtered resin was washed with a mixture of methanol/dichloromethane (1:9) (2×50 ml). The residue obtained on removal of the solvent was subjected to the scavenging process two more times. Removal of the solvent gave the title compound as a yellow oil, yield 1.8 g.

NMR (CDCl₃): 1.41 (3H, t), 1.84 (2H, m), 2.11 (2H, d), 2.82 (2H, t), 3.30 (3H, m), 4.42 (2H, quart), 8.05 (1H, s). MS 241 (M+H).

Method L

Preparation of (3R)-3-(3,5-difluorophenyl)-3-(tetrahydro-2H-pyran-4-yl)propanal

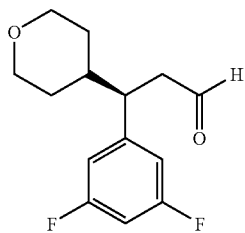

Step 1: Preparation of (2E)-3-(tetrahydro-2H-pyran-4-yl) acrylic acid

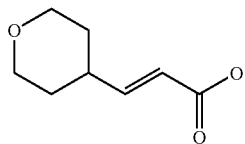

A mixture of tetrahydro-2H-pyran-4-carboxaldehyde (2.47 g), malonic acid (2.26 g) and piperidine (0.2 ml) in pyridine (15 ml) was heated to 100° C. for 4 hours. The reaction mixture was concentrated and partitioned between ethyl acetate (100 ml) and 1N HCl. The organic layer was dried and evaporated to give the title compound, yield 2.77 g. NMR CDCl₃ 1.4-1.8 (m, 4H), 2.4 (m, 1H), 3.4 (m, 2H), 4.0 (m, 2H), 5.8 (d, 1H), 7.0 (dd, 1H).

Step 2: Preparation of (4R,5S)-1,5-dimethyl-4-phenyl-3-[(2E)-3-(tetrahydro-2H-pyran-4-yl)prop-2-enoyl]imidazolin-2-one

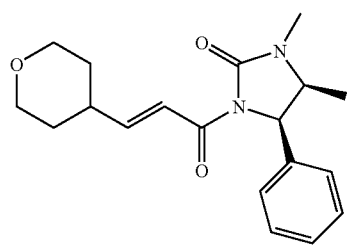

Step A: To a solution of (2E-3-(tetrahydro-2H-pyran-4-yl) acrylic acid (2.76 g) in anhydrous THF (25 ml) was added 1-chloro-N,N-2-trimethyl-1-propenylamine (2.31 ml) and the resulting mixture was stirred for 3 hours.

Step B: To a suspension of (4R,5S)-1,5-dimethyl-4-phenyl-2-imidazidinone (3.32 g) in THF (25 ml), cooled to 5° C., was added dropwise lithium bis(trimethylsilyl)amide (19.2 ml of a 1M solution in THF) under argon. The reaction mixture was stirred for 30 minutes before the addition of the solution of the acid chloride from Step A. The resulting mixture was stirred at room temperature for 18 hours. The reaction was quenched with 50% brine (100 ml) and extracted with ethyl acetate (3×100 ml) and the ethyl acetate extracts were dried and evaporated. The residue was recrystallised from ethanol to give the title compound, yield 3.46 g. NMR CDCl₃ 0.8 (d, 3H), 1.4-1.7 (m, 4H), 2.35 (m, 1H), 2.8 (s, 3H), 3.35 (m, 2H), 3.9 (m, 3H), 5.3 (d, 1H), 6.85 (dd, 1H), 7.1 (m, 2H), 7.25 (m, 3H), 7.4 (d, 1H).

Step 3: Preparation of (4S,5R)-1-[(3R)-3-(3,5-difluorophenyl)-3-(tetrahydro-2H-pyran-4-yl)propanoyl]-3,4-dimethyl-5-phenylimidazolidin-2-one

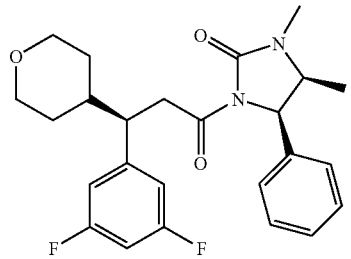

To a suspension of copper iodide (931 mg) in anhydrous THF (60 ml) under argon was added TMEDA (0.81 ml) and the resulting mixture was stirred for 20 minutes. The reaction mixture was cooled to −70° C. and 3,5-difluorophenyl magnesium bromide (9.8 ml of 0.5M solution in THF) was added dropwise and the mixture was stirred for a further 1 hour. A preformed solution of (4R,5S)-1,5-dimethyl-4-phenyl-3-[(2E)-3-(tetrahydro-2H-pyran-4-yl)prop-2-enoyl]imidazolin-2-one (800 mg) and dibutylboron triflate (2.93 ml of 1M solution in dichloromethane) in dichloromethane (2 ml) was added dropwise to the mixture. The reaction mixture was stirred for 1 hour at −70° C. and allowed to warm to room temperature, then saturated ammonium chloride (100 ml) and ethyl acetate (200 ml) was added. Air was blown through the mixture for 1 hour. The ethyl acetate was collected and the aqueous layer was extracted with ethyl acetate (2×100 ml). The combined ethyl acetate layers were washed with water, saturated EDTA, dried and evaporated to dryness. The residue was purified by chromatography on silica eluting with a solvent gradient of isohexane to 75% ethyl acetate/isohexane to give the title compound as a solid. Yield 887 mg. M+H 443. NMR CDCl₃ 0.8 (d, 3H), 1.2-1.5 (m, 3H), 1.7 (m, 2H), 2.85 (s, 3H), 3.0 (m, 1H), 3.15-3.4 (m, 3H), 3.8-4.0 (m, 4H), 5.2 (d, 1H), 6.6-6.7 (m, 3H), 6.85 (m, 2H), 7.2 (m, 3H).

Step 4: Preparation of (3R)-3-(3,5-difluorophenyl)-3-(tetrahydro-2H-pyran-4-yl)propan-1-ol

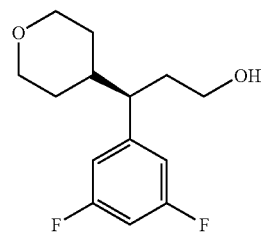

Lithium borohydride (1.5 ml of 2M solution in THF) was added to a solution of (4S,5R)-1-[(3R)-3-(3,5-difluorophenyl)-3-(tetrahydro-2H-pyran-4-yl)propanoyl]-3,4-dimethyl-5-phenylimidazolidin-2-one (882 mg) in anhydrous THF (20 ml) and the mixture was heated to 60° C. for 2 hours. The reaction mixture was cooled and quenched with saturated ammonium chloride and ethyl acetate and stirred for 20 minutes. The organic layer was dried and evaporated to dryness. The residue was purified by chromatography on silica eluting with a gradient of ethyl acetate and isohexane (10:90 to 50:50) to give the title compound as an oil. Yield 345 mg. NMR CDCl₃ 1.2-1.4 (m, 2H), 1.6-1.85 (m, 4H), 2.15,(m, 1H), 2.5 (m, 1H), 3.25-3.6 (m, 4H), 3.9 (m, 1H), 4.05 (m, 1H), 6.7 (m, 3H).

Step 5: Preparation of the Title Compound

Dess-Martin periodinane (628 mg) was added to a solution of (3R)-3-(3,5-difluorophenyl)-3-(tetrahydro-2H-pyran-4-yl)propan-1-ol (345 mg) in dichloromethane (10 ml) and the mixture was stirred for 2 hours. The reaction mixture was washed with 1N NaOH (10 ml) and dried. The solution of the title compound in dichloromethane was used in subsequent reactions.

In a similar manner, but using 3,5-dichlorophenyl magnesium bromide in Step 3 was prepared (3R)-3-(3,5-dichlorophenyl)-3-(tetrahydro-2H-pyran-4-yl)propanal.

Method M

Preparation of (2E)-3-[(2S)-2-methyltetrahydro-2H-pyran-4-yl]acrylic acid

Step 1: Preparation of (2S,4E/Z)-4-(methylmethylene)-2-methyltetrahydro-2H-pyran

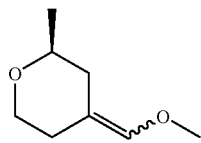

To a suspension of (methoxymethyl)triphenyl phosphine chloride (32 g) in anhydrous THF (160 ml), cooled to −10° C., was added dropwise sodium bis(trimethylsilyl) amide (46.7 ml of 2M solution in THF). The reaction mixture was stirred for 1 hour and then a solution of (2S)-2-methyltetrahydro-4H-pyran-4-one (7.1 g) in anhydrous THF (20 ml) was added over 5 minutes. The resulting mixture was allowed to warm to room temperature and stirred for 3 hours. The reaction was quenched with water (50 ml) and extracted with diethyl ether (3×100 ml). The organics were dried and evaporated to dryness. The resulting gum was treated with diethyl ether and filtered. The organics were evaporated to dryness and the resulting residue was purified by chromatography on silica eluting with ethyl acetate/isohexane (1:9) to give the title compound (~1:1 E/Z mixture of isomers) as an oil. Yield 6.22 g. NMR CDCl₃ 1.1 (dd, 3H), 1.45-2.1 (m, 3H), 2.4-2.55 (m, 1H), 3.2 (m, 2H), 3.4 (s, 3H), 3.85 (m, 1H) 5.7 (m, 1H).

Step 2: Preparation of (2S)-2-methyltetrahydro-2H-pyran-4-carboxaldehyde

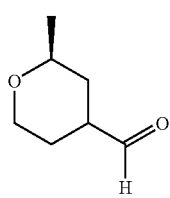

A mixture of (2S,4E/Z)-4-(methylmethylene)-2-methyltetrahydro-2H-pyran (6.22 g) and formic acid (40 ml, 88%) in water (20 ml) was heated, under argon, to 90° C. for 6 hours. The reaction mixture was cooled, neutralised with 6N sodium hydroxide and extracted with diethyl ether (3×150 ml). The organics were dried and evaporated to dryness. The residue was purified by chromatography on silica eluting with ethyl acetate/isohexane (3:7) to give the title compound (4:1 mixture of cis/trans isomers) as an oil. Yield 4.065 g.

NMR CDCl₃ 1.25-1.4 (m, 4H), 1.5-2.2 (m, 3H), 2.45-2.7 (m, 1H), 3.4 3.5 (m, 2H), 3.85-4.1 (m, 1H), 9.65 (s, CHO cis), 9.8 (s, CHO trans).

Step 3: Preparation of the Title Compound

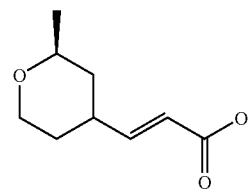

A mixture of (2S)-2-methyltetrahydro-2H-pyran-4-carboxaldehyde (4.0), malonic acid (6.495 g) and piperidine (0.1 ml) in pyridine (10 ml) was heated to 100° C. for 4 hours. The reaction mixture was concentrated and partitioned between ethyl acetate (100 ml) and 1N HCl. The organic layer was dried, evaporated and recrystallised form toluene to give the title compound. Yield 2.48 g. NMR CDCl₃ 1.2 (m, 4H), 1.5 (m, 1H), 1.7 (m, 2H), 2.45 (m, 1H), 3.5 (m, 2H), 4.05 (m, 1H), 5.8 (d, 1H), 7.0 (dd, 1H).

In a similar manner, but starting from 2,6-dimethyltetrahydro-4H-pyran-2-one, was prepared (2E)-3-(2,6-dimethyltetrahydro-2H-pyran-4-yl)acrylic acid. NMR CDCl₃ 1.05 (m, 2H), 1.2 (m, 6H), 1.7 (m, 2H), 2.5 (m, 1H), 3.5 (m, 2H), 5.8 (d, 1H), 7.0 (dd, 1H)

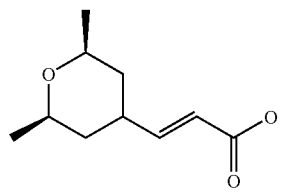

Method N

Preparation of 3-(3-isopropyl-5-methyl-4H-1,2,4-triazol-4-yl)-exo-8-azabicyclo[3.2.1]octane

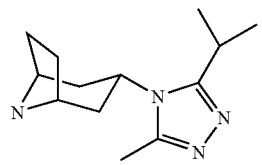

Step 1: Preparation of 8-benzylbicyclo[3.2.1.]octan-3-one

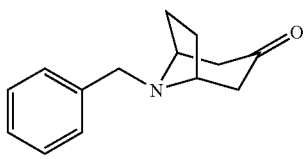

A solution of 2,5-dimethoxytetrahydrofuran (22.2 ml) in 0.1M HCl was refluxed for 1 hour and then cooled to 0° C. 1,3-Acetonedicarboxylic acid (25 g), benzylamine (15.6 ml) and 10% sodium acetate (95 ml) were added in one portion and the resulting mixture was stirred at room temperature for 1 hour, followed by heating to 50° C. for 5 hours. The reaction mixture was cooled, basified with 2M sodium hydroxide and washed with water. The organics were dissolved in 1M hydrochloric acid and washed with dichloromethane. The aqueous layer was rebasified with 2M sodium hydroxide and extracted with ethyl acetate (3×100 ml). The organic extracts were dried and evaporated to dryness to give the title compound as a brown oil which was used without further purification. Yield 13.66 g, M+H 216.

Step 2: Preparation of 8-benzylbicyclo[3.2.1.]octan-3-one-O-methyloxime

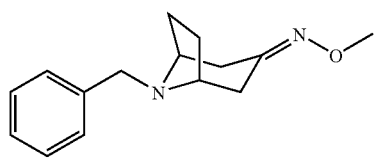

To a solution of 8-benzylbicyclo[3.2.1.]octan-3-one (13.66 g) in ethanol (250 ml) was added pyridine (5.69 ml) followed by hydroxylamine hydrochloride (4.85 g) and the resulting mixture was refluxed for 18 hours. The reaction mixture was allowed to cool to room temperature and then partitioned between water and dichloromethane. The organic layer was dried and evaporated to give the title compound as a brown solid which was used without further purification. Yield 10.79 g. M+H 231.

Step 3: Preparation of 8-benzyl-8-azobicyclo[3.2.1]octan-3-exo-amine

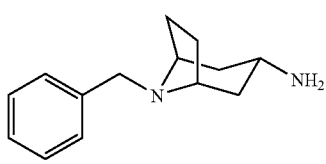

A solution of 8-benzylbicyclo[3.2.1]octan-3-one-O-methyloxime (27.78 g) in pentanol (500 ml) was heated to 165° C. Sodium (10 g) was added portionwise over 6 hours. The reaction was heated for a further 4 hours and then cooled to 5° C. The reaction was acidified with 6M hydrochloric acid and the phases separated. The aqueous extracts were basified with sodium hydroxide and extracted with ethyl acetate (3×100 ml). The combined organic extracts were dried and evaporated to dryness to give the title compound as a pale brown oil. Yield 20.21 g. M+H 217.

Step 4: Preparation of N-(8-benzyl-8-azabicyclo[3.2.1]oct-3-yl-exo)-2-methylpropanamide

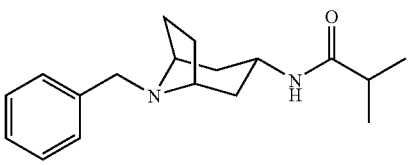

To a solution of 8-benzyl-8-azabicyclo[3.2.1]octan-3-exo-amine (10 g) in DMF (20 ml) was added triethylamine (9.7 ml) and isobutyric acid (6.43 ml) followed by O-(7-azabenzotriazol-1yl)-N,N,N'N'-tetramethyluronium hexafluorophosphate (HATU, 26.36 g) and the resulting mixture was allowed to stir for 18 hours. The reaction mixture was poured onto water and extracted with ethyl acetate (3×50 ml). The organics were extracted with 6M hydrochloric acid. The acid extracts were basified with sodium hydroxide and then extracted with ethyl acetae (3×50 ml). The organic extracts were dried and evaporated to dryness to give the title compound as a pale brown solid. Yield 5.99 g. M+H 287; NMR CDCl₃ 1.1 (d, 6H), 1.5 (m, 2H), 1.6-2.05 (m, 6H), 2.3 (m, 1H), 3.2 (m, 2H), 4.2 (m, 1H), 5.2 (m, 1H), 7.2-7.4 (m, 5H).

Step 5: Preparation of 8-benzyl-3-(3-isopropyl-5-methyl-4H-1,2,4-triazol-4-yl)-exo-8-azabicyclo[3.2.1]octane

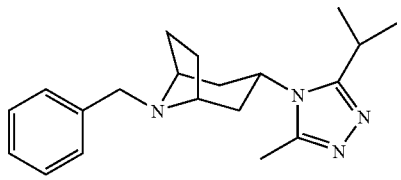

Phosphorous oxychloride (13 ml) was added slowly to a solution of N-(8-benzyl-8-azabicyclo[3.2.1]oct-3-yl-exo)-2-methylpropanamide (13.27 g) in pyridine (25 ml) and chloroform (50 ml) at 0° C. The reaction mixture was allowed to warm to room temperature and stirred for 18 hours. The mixture was evaporated and azeotroped with toluene. The residue was dissolved in chloroform (50 ml) and diisopropylethylamine (24 ml) and acetic anhydride (5.15 g) and the resulting mixture was refluxed for 18 hours. Saturated aqueous sodium carbonate (250 ml) was added and the product was extracted with dichloromethane. The organic extracts were dried and evaporated. The residue was dissolved in 6M hydrochloric acid and refluxed for 18 hours. The reaction mixture was allowed to cool to room temperature, basified with 6M sodium hydroxide, extracted with dichloromethane (3×50 ml), dried and evaporated to dryness. The residue was purified by column chromatography on silica eluting with a gradient of dichloromethane to 5% (7M NH₃ in methanol) in dichloromethane to give the title compound as an off white solid. Yield 2.31 g. M+H 325.

NMR CDCl₃ 1.4 (d, 6H), 1.7 (m, 4H), 2.1-2.4 (m, 4H), 2.6 (s, 3H), 3.05 (m, 1H), 3.4 (bs, 2H), 3.6 (s, 2H), 4.3 (m, 1H), 7.2-7.4 (m, 5H).

Step 6: Preparation of 3-(3-isopropyl-5-methyl-4H-1,2,4-triazol-4-yl)-exo-8-azabicyclo[3.2.1]octane

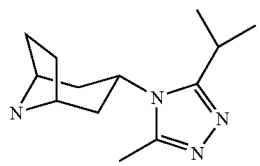

To a solution of 8-benzyl-3-(3-isopropyl-5-methyl-4H-1,2,4-triazol-4-yl)-exo-8-azabicyclo[3.2.1]octane (2.3 g) in ethanol (70 ml) was added 20% palladium hydroxide (230 mg) and the resulting mixture was stirred under a hydrogen atmosphere for 18 hours. The reaction mixture was filtered and evaporated to give the title compound as a white solid. Yield 1.88 g. NMR CDCl$_3$ 1.4(d, 6H), 1.7-1.8 (m, 4H), 1.95 (m, 2H), 2.1-2.3 (m, 4H), 2.55 (s, 3H), 3.05 (m, 1H), 4.35 (m, 1H).

Method O

Preparation of 3-piperidin-4-yl-3H-imidazo[4,5-c]pyridine

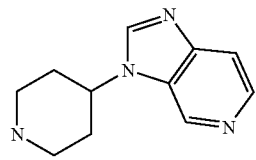

Step 1: Preparation of 3-fluoro-4-nitropyridine-N-oxide

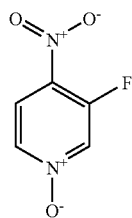

To 3-fluoropyridine-N-oxide (5.0 g) was added carefully concentrated sulphuric acid (8 ml), keeping the temperature below 5° C. and then a mixture of fuming nitric acid (5.5 ml) in concentrated sulphuric acid (8 ml) was added dropwise over 15 minutes. The resulting mixture was heated to 90° C. for 90 minutes. The mixture was cooled, poured onto 200 g of ice and extracted with dichloromethane (×3). The combined organic extracts were dried and evaporated to give the title compound as a yellow solid, yield 3.64 g, which was used without further purification. NMR (d6 DMSO) 8.2 (m, 2H), 8.9 (m, 1H).

Step 2: Preparation of tert-butyl 4-[(4-nitro-1-oxidopyridin-3-yl)amino]piperidine-1-carboxylate.

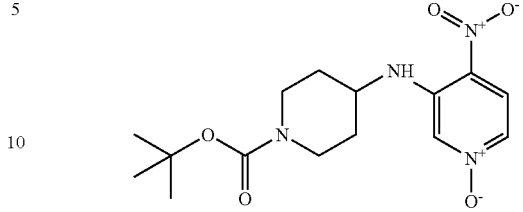

To a mixture of 3-fluoro-4-nitropyridine-N-oxide (3.46 g) and tert-butyl 4-aminopiperidine-1-carboxylate (2.745 g) in acetonitrile (150 ml) was added anhydrous potassium carbonate (2.74 g) and the resulting mixture was refluxed for 8 hours. The mixture was filtered and washed well with dichloromethane. The organics were concentrated to dryness and the residue was purified by column chromatography eluting with a mixture of ethyl acetate and dichloromethane (1:1) to give the titled compound as a yellow solid. Yield 3.25 g. NMR (d6 DMSO) 1.4 (s, 9H), 1.5 (M, 2H), 1.9 (m, 2H), 2.95 (m, 2H), 3.9 (m, 3H), 7.5 (dd, 1H), 7.85 (d, 1H), 8.05 (d, 1H) 8.4 (d, 1H).

Step 3: Preparation of tert-butyl 4-[(4-aminopyridin-3-yl)amino]piperidine-1-carboxylate

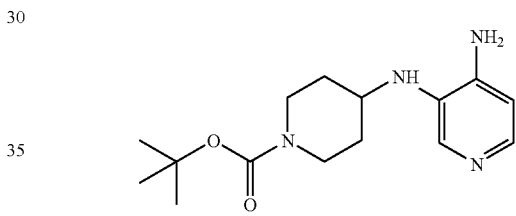

To a solution of tert-butyl 4-[(4-nitro-1-oxidopyridin-3-yl)amino]piperidine-1-carboxylate (4 g) in methanol (100 ml) was added 10% palladium on carbon (50 mg) and the mixture was placed under a hydrogen atmosphere (60 psi) for 48 hours. The mixture was filtered through Celite and evaporated to dryness to give the title compound as a solid, which was used without further purification. Yield 3.21 g. MS 293 (M+H).

Step 4: Preparation of tert-butyl 4-(3H-imidazo[4,5-c]pyridine-3-yl)piperidine-1-carboxylate

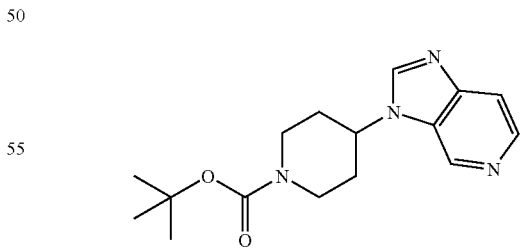

To tert-butyl 4-[(4-nitro-1-oxidopyridin-3-yl)amino]piperidine-1-carboxylate (1.6 g) in toluene (3 ml) was added trimethyl orthoformate (3.6 ml) followed by p-toluenesulfonic acid (105 mg) and the resulting mixture was heated to 105° C. for 4 hours. The mixture was cooled and partitioned between ethyl acetate (75 ml) and water (75 ml). The organic layer was washed with brine, dried and evaporated to dryness to give the title compound as a solid. Yield 1.18 g. NMR (CDCl₃) 1.5 (s, 9H), 2.1 (m, 2H), 2.25 (m, 2H), 3.0 (m, 2H), 4.4 (m, 3H), 7.7 (dd, 1H), 8.1 (s, 1H), 8.5 (d, 1H), 8.9 (s, 1H).

In a similar manner, but using trimethyl orthoacetate, was prepared tert-butyl 4-(2-methyl-3H-imidazo[4,5-c]pyridine-3-yl)piperidine-1-carboxylate. NMR (CDCl₃) 1.55 (s, 9H), 1.95 (m, 2H), 2.4 (m, 2H), 2.7 (s, 3H), 2.9 (m, 2H), 4.4 (m, 3H), 7.6 (d, 1H), 8.4 (d, 1H), 8.85 (s, 1H).

Step 5: Preparation of 3-piperidin-4-yl-3H-imidazo[4,5-c]pyridine

To a solution of tert-butyl 4-(3H-imidazo[4,5-c]pyridine-3-yl)piperidine-1-carboxylate (1.12 g) in 1,4 dioxan (10 ml) was added 4M hydrochloric acid in dioxin (10 ml) and the resulting mixture was stirred for 3 hours. Diethyl ether (30 ml) was added and the mixture was filtered and washed with diethyl ether (50 ml) to give the title compound which was used without further purification. Yield 1.1 g. NMR (d6 DMSO) 2.35 (m, 2H), 2.5 (m, 2H), 3.1 (m, 2H), 3.5 (m, 2H), 5.05 (m, 1H), 8.3 (d, 1H), 8.65 (d, 1H), 9.3 (bd, 2H), 9.9 (s, 1H).

In a similar manner but starting from tert-butyl 4-(2-methyl-3H-imidazo[4,5-c]pyridine-3-yl)piperidine-1-carboxylate was prepared 2-methyl-3-piperidin-4-yl-3H-imidazo[4,5-c]pyridine. NMR (d6 DMSO) 2.15 (m, 2H), 2.75-2.8 (m, 2H), 2.8 (s, 3H), 3.15 (m, 2H), 3.5 (m, 2H), 5.05 (m, 1H), 8.15 (d, 1H), 8.55 (d, 1H), 9.4 (bd, 1H), 9.85 (bd, 1H), 10.0 (s, 1H).

Preparation of 1-piperidine-4-yl-1H-imidazo[4,5-c]pyridine

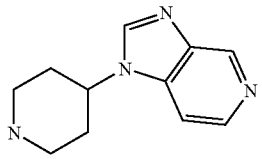

In a similar manner to Steps 2-5 but using 4-methoxy-3-nitropyridine hydrochloride was prepared the title compound. NMR (CDCl₃) 2.1 (m, 4H), 2.85 (m, 2H), 3.3 (M, 2H), 4.3 (m, 1H), 7.4 (dd, 1H), 8.05 (s, 1H), 8.45 (d, 1H), 9.1 (s, 1H).

Method P

Preparation of 4-[3-methyl-5-(trifluoromethyl)-4H-1,2,4-triazol-4-yl]piperidine

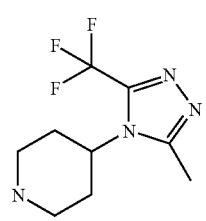

Step 1: Preparation of 1-benzyl-4-[3-methyl-5-(trifluoromethyl)-4H-1,2,4-triazol-4-yl]piperidine

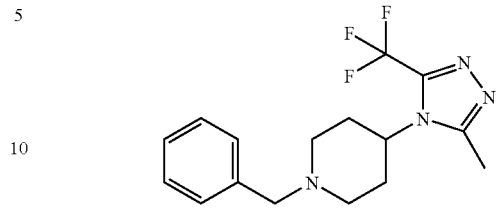

Phosphorous oxychloride (13.0 ml) was added dropwise to a mixture of N-(1-benzylpiperidin-4-yl)acetamide (10.75 g) in chloroform (30 ml) containing pyridine (22.5 ml) at 0° C. under an argon atmosphere. The reaction mixture was allowed to warm to room temperature and stirring was continued for 12 hours. The reaction mixture was evaporated to dryness under vacuum and the residue was azeotroped with toluene (100 ml). The residue obtained was dissolved in chloroform (30 ml), trifluoro acetic acid hydrazide (8.89 g) was added and the mixture was heated under reflux for 4 hours. The reaction mixture was allowed to cool and saturated aqueous sodium bicarbonate (100 ml) was added and the mixture was extracted with dichloromethane (3×100 ml) and the combined extracts were dried. The residue obtained on removal of the solvent was stirred with 2M HCl (65 ml) for 2 hours. The reaction mixture was evaporated to dryness and the residue partitioned between saturated aqueous potassium carbonate (100 ml) and dichloromethane (100 ml). The aqueous portion was extracted with dichloromethane (2×100 ml), the combined organic extracts were dried and evaporated to dryness to give a brown solid, yield 2.97 g, NMR (CDCl₃); 1.90 (2H, d), 2.08 (4H, m), 2.64 (3H, s), 3.04 (2H, d), 3.58 (2H, s), 4.16 (1H, m), 7.30 (5H, m).

Step 2: Preparation of the Title Compound

A solution of 1-benzyl-4-[3-methyl-5-(trifluoromethyl)-4H-1,2,4-triazol-4-yl]piperidine (2.97 g) in ethanol (45 ml) was hydrogenated under a hydrogen filled balloon using 20% palladium hydroxide on charcoal as catalyst. The mixture was filtered through celite and evaporated to dryness to give the title compound, yield 2.14 g, LC-MS M+H 235, NMR (CDCl₃); 1.90 (2H, d), 2.16 (2H, m), 2.42 (1H, br N—H), 2.66 (3H, s), 2.78 (2H, t), 3.32 (1H, d), 4.26 (1H, m).

In an analogous manner using N-8-azabicyclo[3.2.1]oct-3-(exo)-ylacetamide as starting material there is obtained 3-(exo)-[3-methyl-5-(trifluoromethyl)-4H-1,2,4-triazol-4-yl]-8-azabicyclo[3.2.1]octane.

NMR (CDCl₃): 1.4-1.8 (m, 9H), 2.0 (m, 4H), 2.2-2-3 (m, 4H), 2.6 (m, 2H), 2.7 (s, 3H), 2.75 (m, 1H), 2.8 (s, 3H), 3.35 (m, 2H), 3.8 (m, 1H), 3.9 (m, 1H), 4.6 (m, 1H), 6.7-6.8 (m, 3H).

MS (ES) 576 (M+H)⁺

In an analogous manner but using 2,2-difluoroacetohydrazide (Method X) instead of trifluoro acetic acid hydrazide and N-(8-benzyl-8-azabicyclo[3.2.1]oct-3-(exo)-yl)acetamide in step 1 was prepared 3-(exo)-[3-methyl-5-(difluoromethyl)-4H-1,2,4-triazol-4-yl]-8-azabicyclo[3.2.1]octane.

NMR DMSO: 2.0 (m, 6H), 2.4 (t, 2H), 2.58 (s, 3H), 4.18 (m, 2H), 4.58 (m, 1H), 7.78 (t, 1H).

M+H 243.

In an analogous manner but using acethydrazide instead of trifluoro acetic acid hydrazide and N-(8-benzyl-8-azabicyclo

[3.2.1]oct-3-(exo)-yl)acetamide in step 1 was prepared 3-(exo)-[3,5-dimethyl-4H-1,2,4-triazol-4-yl]-8-azabicyclo[3.2.1]octane.

NMR (DMSO) 1.70 (m, 6H), 1.95 (td, 2H), 2.90 (s, 6H), 3.50 (s, 2H), 4.20 (m, 1H).

M+H 207.

In an similar manner but starting from N-(8-benzyl-8-azabicyclo[3.2.1]oct-3-(exo)-yl)propanamide and using acethydrazide instead of trifluoro acetic acid hydrazide in step 1 was prepared 3-(exo)-(3-ethyl-5-methyl-4H-1,2,4-triazol-4-yl)-8-azabicyclo[3.2.1]octane. MS 221 (M+H)

In an similar manner but starting from N-(8-benzyl-8-azabicyclo[3.2.1]oct-3-(exo)-yl)cyclopropanecarboxamide and using acethydrazide instead of trifluoro acetic acid hydrazide in step 1 was prepared 3-(exo)-(3-cyclopropyl-5-methyl-4H-1,2,4-triazol-4-yl)-8-azabicyclo[3.2.1]octane.

NMR (DMSO) 1.1-1.3 (m, 4H), 1.8-2.1 (m, 6H), 2.3-2.5 (m, 4H), 2.6 (s, 3H), 3.8-3.9 (m, 2H), 4.6 (m, 1H).

M+H 233

Method Q

Preparation of 1-piperidin-4-yl-1,3-dihydro-2H-imidazol-2-one

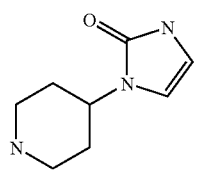

Aminoacetaldehyde dimethylacetal (1.2 g) was added to a solution of benzyl 4-isocyanatopiperidine-1-carboxylate (3 g) in THF (100 ml) and the mixture was stirred for 3 hours. 20% Palladium on charcoal (500 mg) was added and the mixture was hydrogenated under a hydrogen filled balloon. The catalyst was filtered through Celite and the residue was evaporated to dryness then dissolved in ethanol and subjected to repeat hydrogenation with fresh palladium on charcoal catalyst (500 mg). The catalyst was filtered through Celite and the residue was evaporated to dryness then dissolved in 2M HCl (50 ml) and allowed to stand for 4 hours. The reaction mixture was basified with 2M NaOH (50 ml) and evaporated to dryness using toluene (100 ml) to azeotrope final traces of solvent. The residue was triturated with methanol (100 ml) and filtered. The filtrate was evaporated to dryness to give the title compound as an off-white solid, yield 2.2 g, NMR DMSO D6 (Part spectrum some peaks obscured by DMSO): 1.3-1.8 (m, 5H) 3 (m, 2H) 3.9 (m, 1H) 6.3 (d, 1H) 6.4 (d, 1H) 9.9 (s broad, 1H).

In an analogous manner using (2,2-dimethoxy-1-methylethyl)amine as starting material there is obtained 4-methyl-1-piperidin-4-yl-1,3-dihydro-2H-imidazol-2-one, NMR DMSO D6 (Part spectrum DMSO D6 obscures some peaks) 1.3-1.8 (m, 5H) 3 (m, 2H) 3.9 (m, 1H) 6.3 (d, 1H) 6.4 (d, 1H) 9.9 (s broad, 1H).

Method R

Preparation of 1-piperidin-4-ylimidazolidin-2-one

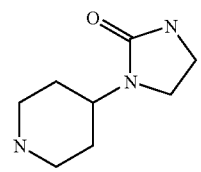

Step 1: Preparation of benzyl 4-(2-oxoimidazolidin-1-yl)piperidine-1-carboxylate

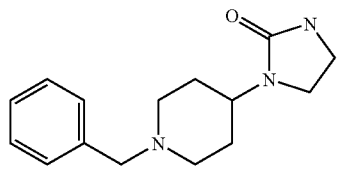

2-Chloroethylisocyanate (2.23 g) was added to a solution of benzyl 4-aminopiperidine-1-carboxylate (5 g) (CAS 120278-07-1) in THF (100 ml) and the mixture was stirred at room temperature for 1 hour. Lithium bis(trimethylsilyl)amide (21 ml of 1M solution in THF) was added and stirring was continued for 16 hours. The clear solution was evaporated to dryness and the residue was dissolved in dichloromethane (50 ml) and the solution was washed with 2M HCl (2×50 ml) and dried. The residue obtained on evaporation of the solvent was purified by chromatography on silica eluting with a solvent gradient of 30% ethyl acetate/isohexane-ethyl acetate, yield 3.2 g.

Step 2: Preparation of the Title Compound

A solution of benzyl 4-(2-oxoimidazolidin-1-yl)piperidine-1-carboxylate (3.2 g) in ethanol (200 ml) was hydrogenated under a hydrogen filled balloon with 20% palladium on charcoal as catalyst. The catalyst was filtered and the filtrate evaporated to dryness to give the title compound as a white solid, yield 1.6 g.

Method S

Preparation of 1-[4-(methylsulphonyl)benzyl]-3-piperidin-4-ylimidazolidin-2-one

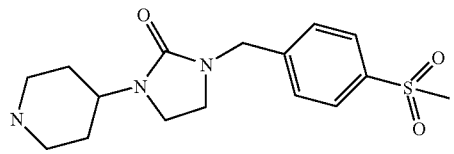

Step 1: Preparation of 1-(1-benzylpiperidin-4-yl)-3-[4-(methylsulphonyl)benzyl]-1,3-dihydro-2H-imidazol-2-one

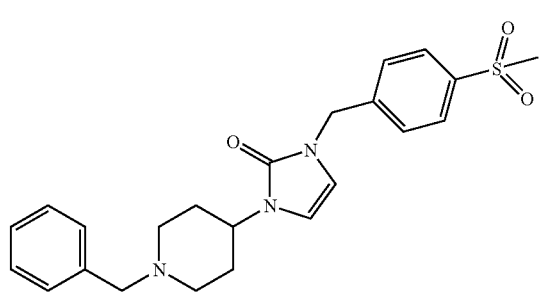

Trimethylsilyl chloride was added to a suspension of potassium iodide (2.47 g) in acetonitrile (40 ml) and the mixture was stirred for 1 hour. A solution of benzyl 4-{3-[4-(methylsulphonyl)benzyl]-2-oxo-2,3-dihydro-1H-imidazol-1-yl}piperidine-1-carboxylate (1.4 g) in acetonitrile (10 ml) was added and stirring was continued for 8 hours. The solvent was evaporated and the residue was suspended in 2M NaOH and extracted with dichloromethane (4×50 ml). The combined dichloromethane extracts were dried and the solvent was evaporated. The residue was redissolved in dichloromethane (20 ml) and poured on to a 20 g SCX2 cartridge and eluted with methanol (5×20 ml) and 1M ammonia in methanol (5×20 ml). The combined methanolic ammonia washings were evaporated, yield 1.2 g, NMR CDCl$_3$ 1.6-2.2 (m, 7H) 2.9 (m, 3H) 3.1 (s, 3H) 4.9 (s, 2H) 6.1 (d, 1H) 6.3 (d, 1H) 7.3 (m, 5H) 7.4 (d, 2H) 7.9 (d, 2H).

The benzyl 4-{3-[4-(methylsulphonyl)benzyl]-2-oxo-2,3-dihydro-1H-imidazol-1-yl}piperidine-1-carboxylate used as starting material was obtained by alkylation of benzyl 4-(2-oxo-2,3-dihydro-1H-imidazol-1-yl)piperidine-1-carboxylate (obtained by reaction of benzyl 4-isocyanatopiperidine-1-carboxylate with aminoacetaldehyde dimethyl acetal as described in Method Q) following the method outlined in Example 10.

Step 2: Preparation of the Title Compound

A solution of 1-(1-benzylpiperidin-4-yl)-3-[4-(methylsulphonyl)benzyl]-1,3-dihydro-2H-imidazol-2-one (1.2 g) in ethanol was hydrogenated under a hydrogen filled balloon using 20% palladium on charcoal as catalyst. The catalyst was filtered and the filtrate evaporated to dryness to give the title compound, yield 0.6 g, NMR CDCl$_3$ 1.6-2 (m, 5H) 2.8 (m, 1H) 3.05 (s, 3H) 3.2-4.5 (m, 7H) 4.45 (s, 2H) 7.5 (d, 2H) 7.9 (d, 2H).

Method T

Preparation of 1-endo-(8-azabicyclo[3.2.1]oct-3-yl)-5-(methylsufonyl)-1H-benzamidazole

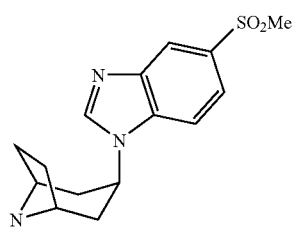

Step 1: Preparation of 8-benzylbicyclo[3.2.1.]octan-3-one

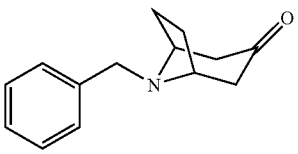

A solution of 2,5-dimethoxytetrahydrofuran (22.2 ml) in 0.1M HCl was refluxed for 1 hour and then cooled to 0° C. 1.3-Acetonedicarboxylic acid (25 g), benzylamine (15.6 ml) and 10% sodium acetate (95 ml) was added in one portion and the resulting mixture was stirred at room temperature for 1 hour and then heated to 50° C. for 5 hours. The reaction mixture was cooled, basified with 2M sodium hydroxide, extracted with dichloromethane and washed with water. The organics were extracted with 1M hydrochloric acid and washed with dichloromethane. The aqueous layer was basified with 2M sodium hydroxide and extracted with ethyl acetate (3×100 ml). The organic extracts were dried and evaporated to dryness to give the title compound as a brown oil which was used without further purification. Yield 13.66 g. MS 216 MH$^+$.

Step 2: Preparation of tert-butyl 3-oxo-8-azabicyclo[3.2.1]octane-8-carboxylate

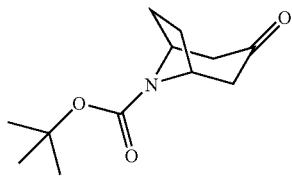

To a solution of 8-benzylbicyclo[3.2.1]octan-3-one (8.48 g) in ethanol (100 ml) was added 30% palladium on carbon (850 mg) followed by ammonium formate (8.5 g) and the resulting mixture was refluxed for 4 hours. The mixture was cooled, filtered and evaporated to dryness. The residue was dissolved in THF (50 ml) and water (50 ml) and d-tert-butyl dicarbonate (8.61 g) was added. The resulting mixture was stirred at room temperature for 18 hours. The reaction mixture was concentrated and then partitioned between dichloromethane and 1M citric acid. The organic extracts were washed with saturated sodium bicarbonate, brine, dried and evaporated to dryness. The residue was purified by chromatography on silica eluting with ethyl acetate/isohexane (20:80) to give the title compound as an oil which solidified on standing. Yield 4.43 g. NMR CDCl$_3$: 1.5 (s, 9H), 1.7 (m, 2H), 2.1 (m, 2H), 2.35 (m, 2H), 2.7 (m, 2H), 4.5 9 m, 2H).

Step 3: Preparation of tert-butyl 3-endo-(benzylamino)-8-azabicyclo[3.2.1]octane-8-carboxylate

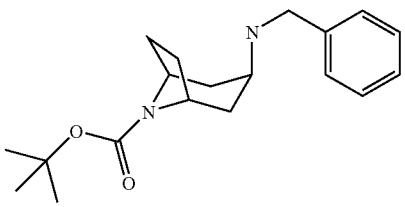

To a solution of tert-butyl 3-oxo-8-azabicyclo[3.2.1]octane-8-carboxylate (4.43 g) in dichloromethane (90 ml) and acetic acid (10 ml) was added benzylamine (2.37 ml) followed by sodium triacetoxyborohydride (6.3 g) and the resulting mixture was stirred for 18 hours. The reaction mixture was concentrated, redissolved in ethyl acetate and washed with saturated sodium bicarbonate. The organic layers were dried and evaporated to dryness. The residue was purified by chromatography on silica eluting with a gradient of ethyl acetate/isohexane to give the title compound as a solid. Yield 2.84 g. NMR CDCl$_3$: 1.5 (s, 9H), 1.6 (m, 2H), 1.9-2.2 (m, 5H), 3.0 (m, 1H), 3.759s, 2H), 4.1 (m, 2H), 7.3 (m, 5H).

Step 4: Preparation of tert-butyl 3-endo-amino-8-azabicyclo[3.2.1]octane-8-carboxylate

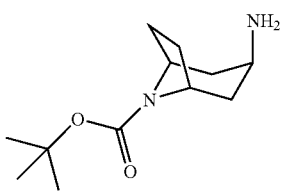

To a solution of tert-butyl 3-endo-(benzylamino)-8-azabicyclo[3.2.1]octane-8-carboxylate (2.84 g) in ethanol (50 ml) was added 30% palladium on carbon (286 mg) followed by ammonium formate (3 g) and the resulting mixture was refluxed for 2.5 hours. The mixture was cooled, filtered and evaporated to dryness to give the title compound, which was used without further purification. MS 227 MH$^+$.

Step 5: Preparation of tert-butyl 3-{[4-(methylsulphonyl)-2-nitrophenyl]amino}-8-endo-azabicyclo[3.2.1]octane-8-carboxylate.

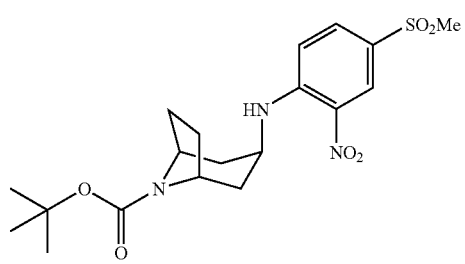

Prepared in a similar manner to Method A, Step 1 but using of tert-butyl 3-endo-amino-8-azabicyclo[3.2.1]octane-8-carboxylate (2.12 g) to give the title compound as a foam. Yield 3.24 g. NMR CDCl$_3$: 1.5 (s, 9H), 1.8 (m, 2H), 2.0-2.2 (m, 6H), 3.1 (3, 3H), 4.0 (m, 1H), 4.3 (m, 2H), 6.85 (d, 1H), 7.9 (dd, 1H), 8.8 9d, 1H), 9.1 (d, 1H).

Step 6: Preparation of 1-endo-(8-azabicyclo[3.2.1]oct-3-yl)-5-(methylsufonyl)-1H-benzamidazole

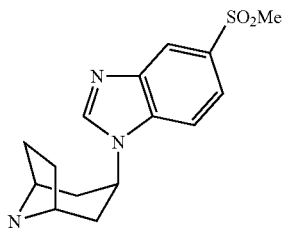

Step A: To a solution of tert-butyl 3-{[4-(methylsulphonyl)-2-nitrophenyl]amino}-8-endo-azabicyclo[3.2.1]octane-8-carboxylate (3.25 g) and trimethyl orthoformate (4.2 ml) in ethanol (100 ml) was added acetic acid (1 ml) and 10% palladium on carbon (100 mg]). The mixture was placed under an atmosphere of hydrogen (5 bar) and heated to 80° C. for 18 hours. The mixture was cooled and filtered to a gum.

Step B: The product from Step A was dissolved in dioxane (20 ml) and 4M HCl (20 ml) was added. The resulting mixture was stirred for 1 hour. Diethyl ether (50 ml) was added and the mixture was filtered and washed with diethyl ether to give the title compound. MS 306 MH$^+$.

Method U

Preparation of 1-exo-(8-azabicyclo[3.2.1]oct-3-yl)-5-(methylsufonyl)-1H-benzamidazole

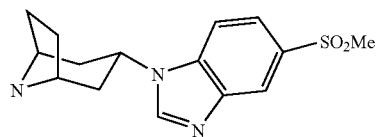

Step 1: Preparation of 8-benzyl-N-[4-(methylsulphonyl)-2-nitrophenyl]-8-exo-azabicyclo[3.2.1]octan-3-amine

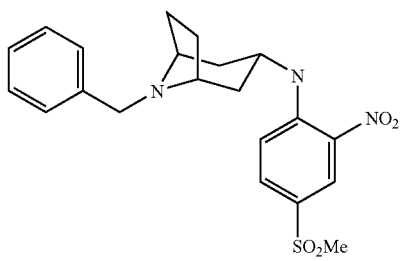

In a similar manner to Method A Step 1 but using 8-benzyl-8-azobicyclo[3.2.1]octan-3-exo-amine (CAS Reg No. 76272-36-1) was prepared 8-benzyl-N-[4-(methylsulphonyl)-2-nitrophenyl]-8-exo-azabicyclo[3.2.1]octan-3-amine. NMR CDCl$_3$: 1.8 (m, 4H), 2.1 (m, 2H), 2.3 (m, 2H), 3.15 (s, 3H), 3.45 (m, 2H), 3.7 (s, 2H), 4.0 (m, 1H), 7.1 9d, 1H), 7.4 (m, 4H), 7.95 (dd, 1H), 8.4 (d, 1H), 8.85 (d, 1H).

Step 2: Preparation of 1-(8-benzyl-8-exo-azabicyclo[3.2.1]oct-3-yl)-5-(methylsufonyl)-1H-benzamidazole

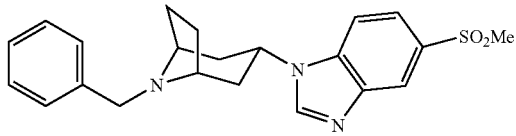

In a similar manner to Method T Step 6, Step A was prepared 1-(8-benzyl-8-exo-azabicyclo[3.2.1]oct-3-yl)-5-(methylsufonyl)-1H-benzamidazole as oil, which solidified on standing. NMR CDCl$_3$: 1.9 (m, 4H), 2.3 (m, 4H), 3.1 (s, 3H), 3.45 (m, 2H), 3.65 (s, 2H), 4.7 (m, 1H), 7.4 (m, 5H), 7.65 (m, 1H), 7.9 (m, 1H), 8.2 (s, 1H), 8.4 (s, 1H).

Step 3: Preparation of 1-exo-(8-azabicyclo[3.2.1]oct-3-yl)-5-(methylsufonyl)-1H-benzamidazole To a solution of 1-(8-benzyl-8-exo-azabicyclo[3.2.1]oct-3-yl)-5-(methylsufonyl)-1H-benzamidazole (1.1 g) in ethanol (50 ml) was added 30% palladium on carbon (110 mg) followed by ammonium formate (1.1 g) and the resulting mixture was heated to 90° C. for 5 hours. An additional portion of ammonium formate (1.1 g) and 30% palladium on carbon (110 mgs) was added and the mixture was heated for a further 8 hours. The mixture was cooled, filtered and evaporated to give a gum, which was purified on a SCX column to give the title compound as a solid. Yield 750 mg. NMR CDCl$_3$: 1.8-2.3 (m, 8H), 3.1 (s, 3H), 3.8 (m, 2H), 4.7 (m, 1H), 7.6 9d, 1H), 7.9 9dd, 1H), 8.2 (s, 1H), 8.4 9s, 1H). MS 306 MH$^+$.

Method V

Preparation of (3R)-3-(3,5-difluorophenyl)-3-(1,1-dioxidotetrahydro-2H-thiopyran-4-yl)propanal

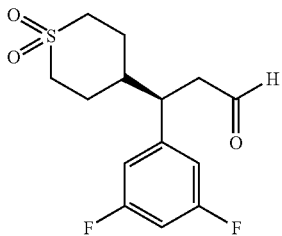

Step 1: Preparation of (4S,5R)-1-[(3R)-3-(3,5-difluorophenyl)-3-(tetrahydro-2H-thiopyran-4-yl)propanoyl]-3,4-dimethyl-5-phenylimidazolidin-2-one.

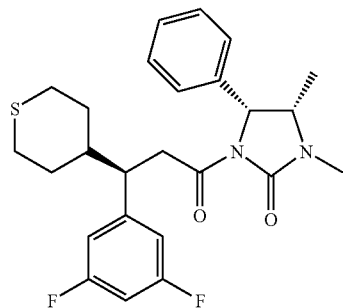

Was prepared in a similar manner to Method L Step 1-3 but starting from tetrahydro-2H-thiopyran-4-carbaldehyde (CAS Reg No. 50675-19-9) instead of tetrahydro-2H-pyran-4-carboxaldehyde. NMR CDCl$_3$ 0.75 (d, 3H), 1.2-1.5 (m, 2H), 1.8 (m, 1H), 2.1 (m, 1H), 2.5-2.6 (m, 5H), 2.85 (s, 3H), 3.1 (m, 2H), 3.75-3.9 (m, 2H), 5.2 (d, 1H), 6.55-6.7 (m, 3H), 6.85 (m, 2H), 7.2 (m, 3H). MS 459 (M+H).

Step 2: Preparation of (4S,5R)-1-[(3R)-3-(3,5-difluorophenyl)-3-(1,1-dioxidotetrahydro-2H-thiopyran-4-yl)propanoyl]-3,4-dimethyl-5-phenylimidazolidin-2-one.

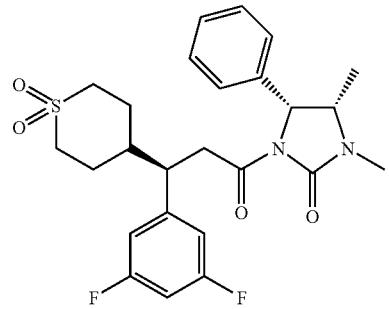

To a solution of (4S,5R)-1-[(3R)-3-(3,5-difluorophenyl)-3-(tetrahydro-2H-thiopyran-4-yl)propanoyl]-3,4-dimethyl-5-phenylimidazolidin-2-one (712 mg) in dichloromethane (60 ml) was added in one portion meta-chloroperoxybenzoic acid (1.53 g, 70% strength). The resulting mixture was stirred at room temperature for 18 hours. The mixture was partitioned between 2N NaOH and dichloromethane. The organic extracts were dried (MgSO$_4$) and evaporated to a gum which was purified by silica chromatography eluting with a gradient of MeOH/dichloromethane (0-2%); to give the title compound as a solid (622 mg). NMR CDCl$_3$ 0.8 (d, 3H), 1.7 (m, 2H), 1.9 (m, 2H), 2.15 (m, 1H), 2.85 (s, 3H), 2.8-3.2 (m, 6H), 3.75 (m, 1H), 3.9 (m, 1H), 5.2 (d, 1H), 6.6 (m, 3H), 6.9 (m, 2H), 7.2 (m, 3H). MS 491 (M+H).

Step 3: Preparation of (3R)-3-(3,5-difluorophenyl)-3-(1,1-dioxidotetrahydro-2H-thiopyran-4-yl)propan-1-ol

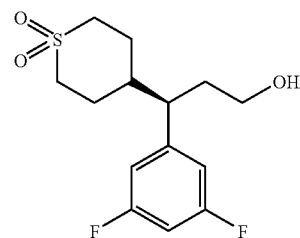

To a solution of (4S,5R)-1-[(3R)-3-(3,5-difluorophenyl)-3-(1,1-dioxidotetrahydro-2H-thiopyran-4-yl)propanoyl]-3,4-dimethyl-5-phenylimidazolidin-2-one (618 mg) in anhydrous THF (15 ml) was added lithium borohydride (1.3 ml of 2M solution in THF). The resulting mixture was heated to 60° C. for 2 hours. The mixture was cooled and quenched with saturated ammonium chloride solution. The mixture was extracted with ethyl acetate (3×50 ml). The organic extracts were dried (MgSO$_4$) and evaporated to a solid to give the title compound, which was used without further purification.

Step 4: Preparation of (3R)-3-(3,5-difluorophenyl)-3-(1,1-dioxidotetrahydro-2H-thiopyran-4-yl)propanal

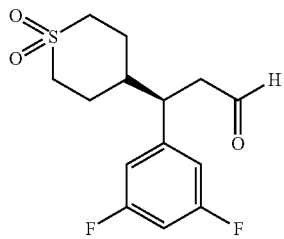

To a solution of (3R)-3-(3,5-difluorophenyl)-3-(1,1-dioxidotetrahydro-2H-thiopyran-4-yl)propan-1-ol (1.26 g) in dichloromethane (10 ml) was added Dess-Martin periodinane (588 mg) in one portion. The resulting mixture was stirred at room temperature for 2 hours. The mixture was partitioned between 1N NaOH solution and dichloromethane. The organics were dried and evaporated to give the title compound as an oil, which was subsequently used without further purification.

Method W

Preparation of 1-(4-methylpiperidin-4-yl)-5-(methylsulfonyl)-1H-benzimidazole

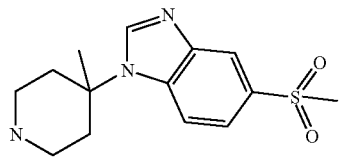

Step 1: Preparation of tert-butyl 4 amino-4-methylpiperidine-1-carboxylate

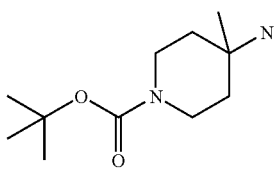

To a solution of 1-(tert-butoxycarbonyl)-4-methylpiperidine-4-carboxylic acid (3.5 g) in anhydrous toluene (50 ml) was added diphenylphosphorylazide (3.72 ml) followed by triethylamine (2.4 ml) and the resulting mixture was heated to 100° C. for 90 minutes. The mixture was cooled, quenched with saturated sodium bicarbonate (20 ml). The organic layer was separated, dried and evaporated to dryness. The crude product was dissolved in tetrahydrofuran (50 ml) to which was added potassium trimethylsilanolate (4.1 g). The resulting mixture was stirred at room temperature for 48 hours. The reaction mixture was filtered, evaporated to 10 ml and poured directly onto an SCX-Silica bond elut. The product was eluted with 0.7M ammonia solution in methanol to give the title compound as an oil (2.83 g);

M+H 159 (-tert-butyl); NMR (CDCl$_3$) 1.2(s, 3H), 1.4(m, 4H) 1.5 (s, 9H), 3.4(m, 4H):

Step 2: Using tert-butyl 4 amino-4-methylpiperidine-1-carboxylate as starting material and following the procedure outlined in Method C, Step 1 there is obtained tert-butyl 4-methyl-4-{[4-(methylsulfonyl)-2-nitrophenyl]amino}piperidine-1-carboxylate, M–H 412.

Using tert-butyl 4-methyl-4-{[4-(methylsulfonyl)-2-nitrophenyl]amino}piperidine-1-carboxylate as starting material and following the procedure outlined in Method C, Step 2 but replacing trimethyl orthoacetate with trimethyl orthoformate, there is obtained tert-butyl 4-methyl-4-[5-(methylsulfonyl)-1H-benzimidazol-1-yl]piperidine-1-carboxylate.

Using tert-butyl 4-methyl-4-[5-(methylsulfonyl)-1H-benzimidazol-1-yl]piperidine-1-carboxylate as starting material and following the procedure outlined in Method C, Step 3 there is obtained the title compound, M+H 294.

Method X

Preparation of 2,2-difluoroacetohydrazide

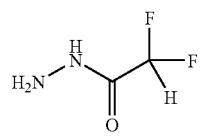

To a solution of hydrazine hydrate (5 ml) in ethanol (10 ml) was added ethyl difluoroacetate (2.62 g) dropwise and the mixture was stirred at room temperature for 3 hours. The mixture was then heated at 80° C. for 1 hour and allowed to cool to room temperature. The mixture was concentrated under reduced pressure to provide 2,2-difluoroacetohydrazide (1.6 g) as a colourless oil.

NMR DMSO 5.9 (dt, 1H), 6.0-6.5 (m, 3H).
M+ 110.

Method Y

Preparation of {4-[(3-exo)-8-azabicyclo[3.2.1]oct-3-yl]-5-methyl-4H-1,2,4-triazol-3-yl}methanol

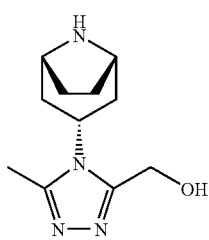

Step 1: Preparation of 2-(benzyloxy)acetohydrazide

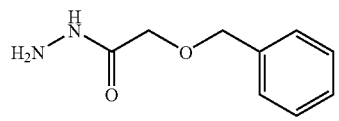

To a solution of hydrazine hydrate (10 ml) in ethanol (100 ml) at 0° C. was added a solution of (benzyloxy)acetyl chloride (6.4 ml) in THF (40 ml) by syringe pump over 30 minutes. The reaction mixture was allowed to warm to room temperature and stirred for 18 hours. The ethanol was removed under reduced pressure and the remaining aqueous mixture extracted with dichloromethane (3×100 ml). The combined organic extracts were washed with aqueous $K_2CO_3$ (100 ml) then brine (100 ml) and dried ($MgSO_4$). Concentration under reduced pressure gave 2-(benzyloxy)acetohydrazide as a colourless oil that crystallized on standing (5.5 g).

NMR $CDCl_3$ 3.73 (d, 2H), 4.08 (s, 2H), 4.58 (s, 2H), 7.35 (m, 5H), 7.65 (s, 1H).

M+Na 203.

Step 2: Preparation of (3-exo)-8-benzyl-3-{3-[(benzyloxy)methyl]-5-methyl-4H-1,2,4-triazol-4-yl}-8-azabicyclo[3.2.1]octane.

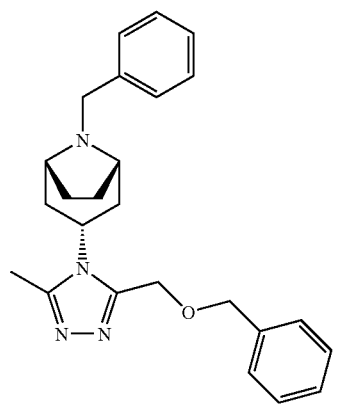

To a solution of N-[(3-exo)-8-benzyl-8-azabicyclo[3.2.1]oct-3-yl]acetamide (1.0 g) in chloroform (30 ml) at 0° C. under an argon atmosphere was added anhydrous pyridine (2 ml) then $POCl_3$ (1.2 ml) dropwise. The mixture was allowed to warm to room temperature and stirred for three hours. The mixture was concentrated under reduced pressure and azeotroped with toluene (×3). The resulting oil was dissolved in chloroform (50 ml) and 2-(benzyloxy)acetohydrazide (1.0 g) was added. This mixture was refluxed for 18 hours and the cooled reaction mixture was washed with aqueous sodium bicarbonate then dried ($MgSO_4$). Concentration under reduced pressure gave an oil that was then stirred in a mixture of THF/2M HCl (1:1 vol, 30 ml) for 18 hours. This mixture was concentrated under reduced pressure then a saturated solution of potassium carbonate (50 ml) was added. The resulting aqueous mixture was extracted with dichloromethane and the combined organic extracts were dried ($MgSO_4$) and concentrated under reduced pressure to a dark oil. Flash chromatography eluting with dichloromethane then 20% methanol in dichloromethane gave (3-exo)-8-benzyl-3-{3-[(benzyloxy)methyl]-5-methyl-4H-1,2,4-triazol-4-yl}-8-azabicyclo[3.2.1]octane as an oil (200 mg).

NMR $CDCl_3$: 1.65 (m, 4H), 2.12 (m, 2H), 2.30 (t, 2H), 3.30 (m, 2H), 3.59 (s, 2H), 4.55 (s, 2H), 4.6 (m, 1H), 4.75 (s, 2H), 7.35 (m, 10H).

M+H 403.

Step 3: Preparation of {4-[(3-exo)-8-azabicyclo[3.2.1]oct-3-yl]-5-methyl-4H-1,2,4-triazol-3-yl}methanol

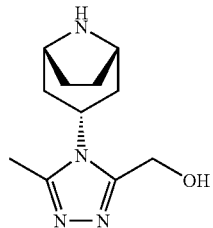

A suspension of (3-exo)-8-benzyl-3-{3-[(benzyloxy)methyl]-5-methyl-4H-1,2,4-triazol-4-yl}-8-azabicyclo[3.2.1]octane (80 mg), ammonium formate (120 mg) and 20% palladium hydroxide on carbon (30 mg) in ethanol (20 ml) was refluxed for 5 hours. The cooled reaction mixture was filtered through a pad of Celite® and the filtrate concentrated under reduced pressure to give {4-[(3-exo)-8-azabicyclo[3.2.1]oct-3-yl]-5-methyl-4H-1,2,4-triazol-3-yl}methanol (33 mg) as a white solid.

NMR $CD_3OD$: 1.9 (m, 6H), 2.25 (td, 2H), 2.55 (s, 3H), 3.70 (m, 2H), 4.75 (s, 2H), 4.77 (m, 1H).

M+H 223.05

Method Z

Preparation of 1-(4-piperidin-4-yl-4H-1,2,4-triazol-3-yl)ethanone

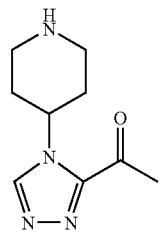

Step 1: Preparation of 1-benzyl-4-(4H-1,2,4-triazol-4-yl)piperidine

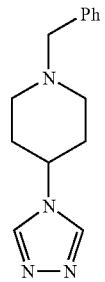

To a solution of 1-benzylpiperidin-4-amine (1 g) in dimethylformamide (100 ml) was added N'-[(1E)-(dimethylamino)methylene]-N,N-dimethylhydrazonoformamide dihydrochloride (1.24 g) and the mixture was refluxed for 18 hours. The reaction mixture was concentrated under reduced pressure and the residue partitioned between ethyl acetate and aqueous potassium carbonate. The organic extracts were washed with brine then dried (MgSO₄). Concentration under reduced pressure gave the crude product as an oil. Flash chromatography eluting with dichloromethane then 10% methanol in dichloromethane gave 1-benzyl-4-(4H-1,2,4-triazol-4-yl)piperidine (260 mg) as an oil.

NMR CDCl₃: 2.1 (m, 8H), 3.05 (d, 2H), 3.55 (s, 2H), 4.05 (m, 1H), 7.30 (m, 5H), 8.25 (s, 2H).

M+Na 265.

Step 2: Preparation of 1-[4-(1-benzylpiperidin-4-yl)-4H-1,2,4-triazol-3-yl]ethanone

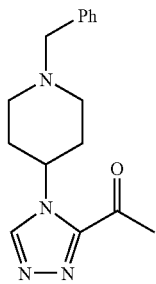

A solution of 1-benzyl-4-(4H-1,2,4-triazol-4-yl)piperidine (200 mg) in acetic anhydride (20 ml) was refluxed for 18 hours. The reaction mixture was concentrated under reduced pressure to a thick oil. Flash chromatography eluting with dischloromethane then 5% methanol in dichloromethane gave 1-[4-(1-benzylpiperidin-4-yl)-4H-1,2,4-triazol-3-yl]ethanone as a colourless oil (60 mg).

NMR (CDCl₃): 1.90 (m, 2H), 2.10 (m, 2H), 2.20 (m, 2H), 3.05 (m, 2H), 4.90 (m, 1H), 7.30 (m, 5H), 8.40 (s, 1H).

M–H 283.

Step 3: Preparation of 1-(4-piperidin-4-yl-4H-1,2,4-triazol-3-yl)ethanone

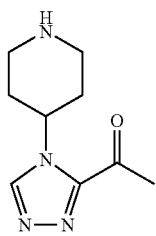

A suspension of the triazole (60 mg), ammonium formate (120 mg) and 20% palladium hydroxide on carbon (20 mg) in ethanol (20 ml) was refluxed for 2 hours. The reaction mixture was filtered through a plug of Celite® and the filtrate concentrated under reduced pressure to give 1-(4-piperidin-4-yl-4H-1,2,4-triazol-3-yl)ethanone as a clear oil (30 mg).

NMR CDCl₃ 1.80 (qd, 2H), 2.05 (m, 2H), 2.15 (m, 2H), 2.80 (s, 3H), 3.30 (d, 2H), 5.0 (m, 1H), 8.42 (s, 1H).

M+H 195.

EXAMPLE 29

The ability of compounds to inhibit the binding of MIP-1α was assessed by an in vitro radioligand binding assay. Membranes were prepared from Chinese hamster ovary cells which expressed the recombinant human CCR5 receptor. These membranes were incubated with 0.1 nM iodinated MIP-1α, scintillation proximity beads and various concentrations of the compounds of the invention in 96-well plates. The amount of iodinated MIP-1α bound to the receptor was determined by scintillation counting. Competition curves were obtained for compounds and the concentration of compound which displaced 50% of bound iodinated MIP-1α was calculated (IC₅₀). Certain compounds of formula (I) have an IC₅₀ of less than 50 μM.

Results from this test for certain compounds of the invention are presented in Table XII. In Table XII the results are presented as Pic50 values. A Pic50 value is the negative log (to base 10) of the IC₅₀ result, so an IC50 of 1 μM (that is 1×10⁻⁶M) gives a Pic50 of 6. If a compound was tested more than once then the data below is an average of the probative tests results.

TABLE XII

| Table No. | Compound No. | pIC₅₀ |
| --- | --- | --- |
| I | 1 | 6.6 |
| I | 8 | 7.4 |
| I | 11 | 8.8 |
| II | 1 | 7.5 |
| II | 5 | 9.3 |
| II | 18 | 7.3 |
| III | 1 | 7.2 |
| IV | 1 | 8.1 |

SCHEME 1

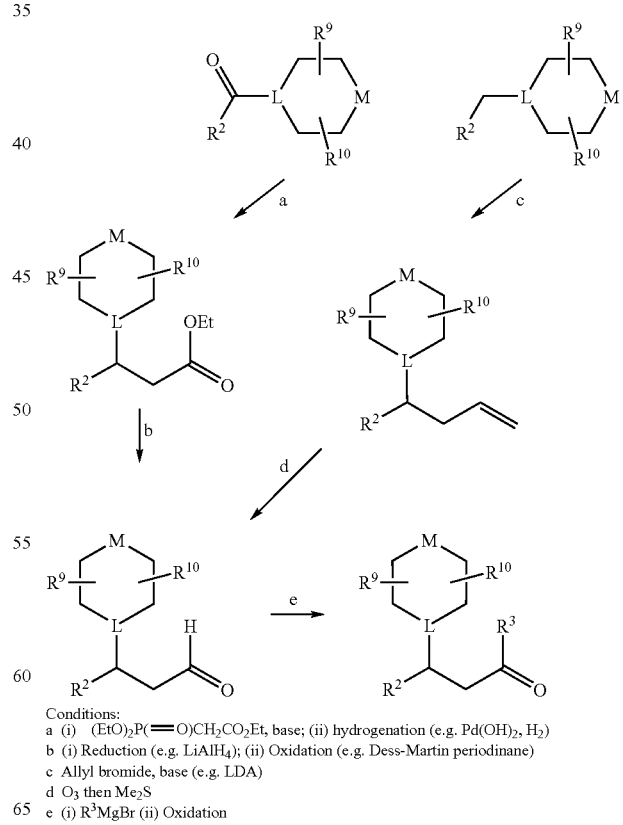

Conditions:
a (i) (EtO)₂P(═O)CH₂CO₂Et, base; (ii) hydrogenation (e.g. Pd(OH)₂, H₂)
b (i) Reduction (e.g. LiAlH₄); (ii) Oxidation (e.g. Dess-Martin periodinane)
c Allyl bromide, base (e.g. LDA)
d O₃ then Me₂S
e (i) R³MgBr (ii) Oxidation

SCHEME 2

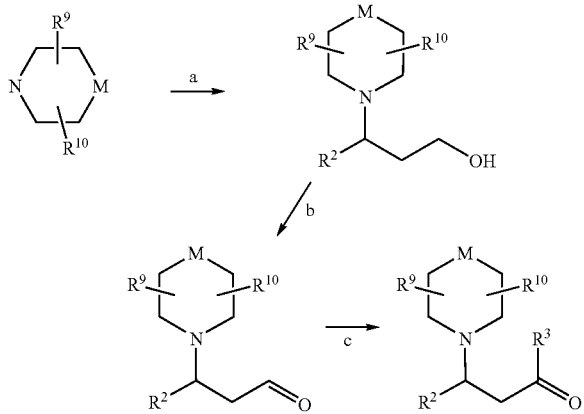

Conditions:
a R²CH(Cl)CH₂CH₂OH, base
b Oxidation (e.g., Dess-Martin periodinane)
c (i) R³MgBr (ii) Oxidation

The invention claimed is:

1. A compound of formula (I):

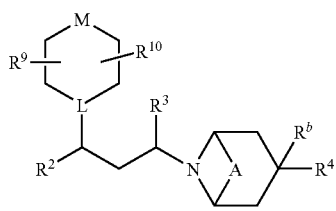

wherein:
A is absent and the bonds attached thereto are absent;
L is CH or N;
M is $NR^1$;
$R^1$ is hydrogen, $C_{1-6}$ alkyl [optionally substituted by phenyl {which itself optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}], phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}, heteroaryl {optionally substituted by halo, $C_{1-4}$ alkyl, $C_{1-4}$ alkoxy, cyano, nitro, $CF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}, $S(O)_2R^5$, $S(O)_2NR^6R^7$, $C(O)R^8$, $C(O)_2(C_{1-6}$ alkyl), $C(O)_2(phenyl(C_{1-2}$ alkyl)) or $C(O)NHR^{11}$;
$R^2$ is phenyl (optionally substituted by halo, CN or $C_{1-4}$ haloalkyl), thienyl or halothienyl;
$R^3$ is hydrogen or methyl;
$R^b$ is hydrogen or $C_{1-3}$ alkyl;
$R^4$ is 1,2,4-triazolyl, thiazolyl, 1,2,4-oxadiazolyl, piperidinyl, benzimidazolyl, 1,3-dihydro-2H-benzimidazolyl, benzotriazolyl, or an imidazopyridinyl, each of which is unsubstituted or substituted by one or two of the same or different $C_{1-6}$ alkyl, $C_{3-6}$ cycloalkyl, $CF_3$, $CHF_2$, OH (which may tautomerise to the keto form), oxo (which may tautomerise to the hydroxy form), $C_{1-4}$ alkyl substituted by $S(O)_2(C_{1-4}$ alkyl), ($C_{1-4}$ alkyl)C(O), ($C_{1-4}$ haloalkyl)C(O), ($C_{1-4}$ alkoxy)C(O), $C(O)NH_2$, $C(O)NH$ ($C_{1-4}$ alkyl), $C(O)NH(phenyl(C_{1-2}$ alkyl)) or phenyl ($C_{1-2}$ alkyl); wherein the phenyl of the foregoing phenyl ($C_{1-2}$ alkyl) groups is optionally substituted by halo, $C_{1-4}$ alkyl, $C_{1-4}$ alkoxy, cyano or $S(O)_2(C_{1-4}$ alkyl);
$R^5$ is $C_{1-6}$ alkyl [optionally substituted by halo, $C_{1-4}$ alkoxy, phenyl {which itself optionally substituted by halo, $C_{1-4}$ alkyl, $C_{1-4}$ alkoxy, cyano, nitro, $CF_3$, $OCF_3$, ($C_{1-4}$ alkyl) C(O)NH, $S(O)_2NH_2$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}], $C_{3-7}$ cycloalkyl (optionally substituted by halo or $C_{1-6}$ alkyl), pyranyl, phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}, heteroaryl {optionally substituted by halo, $C_{1-4}$ alkyl, $C_{1-4}$ alkoxy, cyano, nitro, $CF_3$, ($C_{1-4}$ alkyl)C (O)NH, $S(O)_2NH_2$, $C_{1-4}$ alkylthio, $S(O)(C_{1-4}$ alkyl) or $S(O)_2(C_{1-4}$ alkyl)} or a 5- or 6-membered nitrogen containing heterocyclic ring {optionally substituted by $S(O)_2(C_{1-4}$ alkyl) or $C(O)(C_{1-4}$ alkyl)};
$R^8$ and $R^{11}$ are, independently, hydrogen, $C_{1-6}$ alkyl [optionally substituted by halo, $C_{1-4}$ alkoxy, phenyl {which itself optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2$ ($C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}], $C_{3-7}$ cycloalkyl (optionally substituted by halo or $C_{1-6}$ alkyl), pyranyl, phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2$ ($C_{1-4}$ alkyl)}, heteroaryl {optionally substituted by halo, $C_{1-4}$ alkyl, $C_{1-4}$ alkoxy, cyano, nitro, $CF_3$, ($C_{1-4}$ alkyl)C (O)NH, $S(O)_2NH_2$, $C_{1-4}$ alkylthio, $S(O)(C_{1-4}$ alkyl) or $S(O)_2(C_{1-4}$ alkyl)} or a 5- or 6-membered nitrogen containing heterocyclic ring {optionally substituted by $S(O)_2(C_{1-4}$ alkyl) or $C(O)(C_{1-4}$ alkyl)};
$R^6$ and $R^7$ are, independently, hydrogen or $C_{1-4}$ alkyl; or together $R^6$ and $R^7$ join to form a 5- or 6-membered ring which is optionally substituted with $C_{1-4}$ alkyl or phenyl (wherein the phenyl ring is optionally substituted by halo, cyano, nitro, hydroxy, $C_{1-4}$ alkyl, $C_{1-4}$ alkoxy, $S(O)_mC_{1-4}$ alkyl, $S(O)_2NH_2$, $S(O)_2NH(C_{1-4}$ alkyl), $S(O)_2N(C_{1-4}$ alkyl)$_2$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)$ $NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$);
$R^9$ and $R^{10}$ are, independently, hydrogen or $C_{1-6}$ alkyl;
or a pharmaceutically acceptable salt thereof.

2. A compound of formula (I) as claimed in claim 1 wherein L is CH.

3. A compound of formula (I) as claimed in claim 1 wherein $R^1$ is $C_{1-6}$ alkyl, phenyl {optionally substituted by halo, $C_{1-4}$ alkyl, $C_{1-4}$ alkoxy, cyano, nitro, $CF_3$, $OCF_3$, ($C_{1-4}$ alkyl)C(O) NH, $S(O)_2NH_2$, $C_{1-4}$alkylthio, $S(O)(C_{1-4}$ alkyl) or $S(O)_2(C_{1-4}$ alkyl)}, $S(O)_2R^5$ or $C(O)R^8$; wherein $R^5$ and $R^8$ are $C_{1-6}$ alkyl, $CF_3$, $C_{3-7}$ cycloalkyl (optionally substituted by halo or $C_{1-6}$ alkyl), phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)} or a 5- or 6-membered nitrogen containing heterocyclic ring {optionally substituted by $S(O)_2(C_{1-4}$ alkyl) or $C(O)$ ($C_{1-4}$ alkyl)}.

4. A compound of formula (I) as claimed in claim 1 wherein $R^2$ is phenyl optionally substituted by fluoro, chloro or $CF_3$.

5. A compound of formula (I) as claimed in claim 1 wherein $R^3$ is hydrogen.

6. A compound of formula (I) as claimed in claim 1 claims wherein $R^9$ is hydrogen.

7. A compound of formula (I) as claimed in claim 1 wherein $R^{10}$ is hydrogen.

8. A compound of formula (I) as claimed in claim 1 wherein $R^b$ is hydrogen.

9. A process for preparing a compound as claimed in claim 1, the process comprising reductive amination of a compound of formula (II):

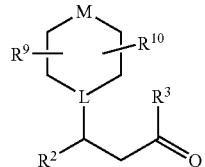

(II)

with a compound of formula (III):

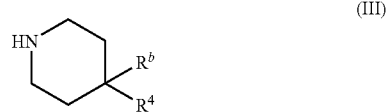

(III)

in the presence of $NaBH(OAc)_3$ (wherein Ac is $C(O)CH_3$) and acetic acid, in a suitable solvent, at room temperature.

10. A pharmaceutical composition which comprises a compound as claimed in any one of claims 1, 2 and 3-8, or a pharmaceutically acceptable salt thereof, and a pharmaceutically acceptable adjuvant, diluent or carrier.

* * * * *

UNITED STATES PATENT AND TRADEMARK OFFICE
CERTIFICATE OF CORRECTION

| | | |
|---|---|---|
| PATENT NO. | : 7,615,555 B2 | Page 1 of 1 |
| APPLICATION NO. | : 11/587330 | |
| DATED | : November 10, 2009 | |
| INVENTOR(S) | : Faull et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this

Twenty-eighth Day of September, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,615,555 B2 | Page 1 of 1 |
| APPLICATION NO. | : 11/587330 | |
| DATED | : November 10, 2009 | |
| INVENTOR(S) | : Faull et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this

Nineteenth Day of October, 2010

David J. Kappos
*Director of the United States Patent and Trademark Office*